US011116531B2

(12) United States Patent
Asher et al.

(10) Patent No.: US 11,116,531 B2
(45) Date of Patent: *Sep. 14, 2021

(54) SURGICAL INSTRUMENT WITH REMOVABLE CLAMP ARM ASSEMBLY

(71) Applicant: Ethicon LLC, Guaynabo, PR (US)

(72) Inventors: Ryan M. Asher, Cincinnati, OH (US); Chad P. Boudreaux, Cincinnati, OH (US); Joseph Dennis, Cincinnati, OH (US); Wei Guo, Shanghai (CN); Bryce L. Heitman, Cincinnati, OH (US); James A. McCrea, Los Gatos, CA (US); Patrick J. Minnelli, Harrison, OH (US); Yachuan Yu, Shanghai (CN); Monica L. Zeckel, Zionsville, IN (US); Junhua Zhu, Shanghai (CN)

(73) Assignee: Cilag GmbH International, Zug (CH)

( * ) Notice: Subject to any disclaimer, the term of this patent is extended or adjusted under 35 U.S.C. 154(b) by 108 days.

This patent is subject to a terminal disclaimer.

(21) Appl. No.: 15/798,680

(22) Filed: Oct. 31, 2017

(65) Prior Publication Data

US 2018/0132883 A1 May 17, 2018

Related U.S. Application Data

(60) Provisional application No. 62/519,482, filed on Jun. 14, 2017, provisional application No. 62/508,720, filed on May 19, 2017, provisional application No. 62/422,698, filed on Nov. 16, 2016.

(51) Int. Cl.
*A61B 17/32* (2006.01)
*A61B 17/3201* (2006.01)
(Continued)

(52) U.S. Cl.
CPC ...... *A61B 17/2804* (2013.01); *A61B 18/1442* (2013.01); *A61B 18/1206* (2013.01);
(Continued)

(58) Field of Classification Search
CPC .... A61B 17/320068; A61B 17/320092; A61B 17/2804; A61B 2017/320094; A61B 2017/0046; A61B 2017/00464
See application file for complete search history.

(56) References Cited

U.S. PATENT DOCUMENTS 5,322,055 A * 6/1994 Davison ......... A61B 17/320068
601/2
5,873,873 A 2/1999 Smith et al.
(Continued)

FOREIGN PATENT DOCUMENTS

JP 2004-033565 A 2/2004
JP 2005-176905 A 7/2005
(Continued)

OTHER PUBLICATIONS

U.S. Appl. No. 15/284,819.
(Continued)

*Primary Examiner* — Todd J Scherbel
(74) *Attorney, Agent, or Firm* — Frost Brown Todd LLC

(57) ABSTRACT

A surgical instrument has a first modular assembly and a second modular assembly. The first modular assembly has a body, an ultrasonic waveguide, an ultrasonic blade connected to a distal end of the ultrasonic waveguide, and a coupling member that movably couples with the body. The second modular assembly has a clamp arm assembly with a first pivot coupling, a clamp pad assembly with a second pivot coupling, and a distal outer sheath that selectively couples to the body of the first modular assembly via the coupling member. The distal outer sheath has an interior surface that houses a portion of the ultrasonic waveguide, and this interior surface also houses the first pivot coupling and the second pivot coupling.

20 Claims, 44 Drawing Sheets

(51) Int. Cl.
*A61B 17/28* (2006.01)
*A61B 18/14* (2006.01)
*A61B 18/00* (2006.01)
*A61B 90/00* (2016.01)
*A61B 17/00* (2006.01)
*A61B 18/12* (2006.01)

(52) U.S. Cl.
CPC ............. *A61B 2017/0046* (2013.01); *A61B 2017/00106* (2013.01); *A61B 2017/00424* (2013.01); *A61B 2017/00477* (2013.01); *A61B 2017/00876* (2013.01); *A61B 2017/2825* (2013.01); *A61B 2017/2845* (2013.01); *A61B 2017/320074* (2017.08); *A61B 2017/320082* (2017.08); *A61B 2017/320084* (2013.01); *A61B 2017/320088* (2013.01); *A61B 2017/320093* (2017.08); *A61B 2017/320094* (2017.08); *A61B 2017/320095* (2017.08); *A61B 2018/0063* (2013.01); *A61B 2018/0094* (2013.01); *A61B 2018/00642* (2013.01); *A61B 2018/00666* (2013.01); *A61B 2018/00672* (2013.01); *A61B 2018/00755* (2013.01); *A61B 2018/00875* (2013.01); *A61B 2018/00916* (2013.01); *A61B 2018/00958* (2013.01); *A61B 2018/00994* (2013.01); *A61B 2090/034* (2016.02); *A61B 2090/065* (2016.02); *A61B 2090/0811* (2016.02); *A61B 2090/0813* (2016.02)

(56) References Cited

U.S. PATENT DOCUMENTS

| | | | |
|---|---|---|---|
| 5,935,144 | A | 8/1999 | Estabrook |
| 5,980,510 | A | 11/1999 | Tsonton et al. |
| 6,129,735 | A | 10/2000 | Okada et al. |
| 6,139,561 | A * | 10/2000 | Shibata .......... A61B 17/320092 606/169 |
| 6,325,811 | B1 | 12/2001 | Messerly |
| 6,773,444 | B2 | 8/2004 | Messerly |
| 6,783,524 | B2 | 8/2004 | Anderson et al. |
| 7,563,269 | B2 | 7/2009 | Hashiguchi |
| 8,048,074 | B2 | 11/2011 | Masuda |
| 8,461,744 | B2 | 6/2013 | Wiener et al. |
| 8,591,536 | B2 | 11/2013 | Robertson |
| 8,623,027 | B2 | 1/2014 | Price et al. |
| 8,768,435 | B2 | 7/2014 | Andrus et al. |
| 8,905,935 | B2 | 12/2014 | Akagane |
| 8,926,610 | B2 | 1/2015 | Hafner et al. |
| 8,986,302 | B2 | 3/2015 | Aldridge et al. |
| 9,023,071 | B2 | 5/2015 | Miller et al. |
| 9,050,120 | B2 | 6/2015 | Swarup et al. |
| 9,072,523 | B2 | 7/2015 | Houser et al. |
| 9,084,878 | B2 | 7/2015 | Kawaguchi et al. |
| 9,095,367 | B2 | 8/2015 | Olson et al. |
| 9,326,787 | B2 | 5/2016 | Sanai et al. |
| 9,351,753 | B2 | 5/2016 | Balanev et al. |
| 9,381,058 | B2 | 7/2016 | Houser et al. |
| 9,393,037 | B2 | 7/2016 | Olson et al. |
| 9,510,891 | B2 | 12/2016 | Allen, IV et al. |
| 9,566,084 | B2 | 2/2017 | Katsumata |
| 9,572,622 | B2 | 2/2017 | Shelton, IV et al. |
| 9,901,360 | B2 | 2/2018 | Neurohr et al. |
| 9,949,785 | B2 | 4/2018 | Price et al. |
| 10,543,383 | B2 | 1/2020 | Kase |
| 10,568,682 | B2 | 2/2020 | Dycus et al. |
| 10,736,648 | B2 * | 8/2020 | Denzinger .......... A61B 17/2804 |
| 2004/0193199 | A1 * | 9/2004 | Hashiguchi .... A61B 17/320092 606/169 |
| 2006/0079874 | A1 | 4/2006 | Faller et al. |
| 2007/0191713 | A1 | 8/2007 | Eichmann et al. |
| 2007/0282333 | A1 | 12/2007 | Fortson et al. |
| 2008/0200940 | A1 | 8/2008 | Eichmann et al. |
| 2012/0116265 | A1 | 5/2012 | Houser et al. |
| 2014/0135804 | A1 | 5/2014 | Weisenburgh, II et al. |
| 2014/0221994 | A1 | 8/2014 | Reschke |
| 2015/0080924 | A1 | 3/2015 | Stulen et al. |
| 2015/0080925 | A1 | 3/2015 | Schulte et al. |
| 2015/0148835 | A1 | 5/2015 | Faller et al. |
| 2015/0265305 | A1 * | 9/2015 | Stulen .................. A61B 17/285 606/169 |
| 2016/0030076 | A1 | 2/2016 | Faller et al. |
| 2016/0074061 | A1 * | 3/2016 | Neurohr ......... A61B 17/320092 606/169 |
| 2016/0175001 | A1 | 6/2016 | Hibner et al. |
| 2017/0105754 | A1 | 4/2017 | Boudreaux et al. |
| 2017/0105755 | A1 | 4/2017 | Boudreaux et al. |
| 2017/0105788 | A1 | 4/2017 | Boudreaux |
| 2018/0132884 | A1 | 5/2018 | Denzinger et al. |
| 2018/0132887 | A1 | 5/2018 | Asher et al. |
| 2018/0132888 | A1 | 5/2018 | Asher et al. |
| 2018/0132926 | A1 | 5/2018 | Asher et al. |
| 2018/0256245 | A1 | 9/2018 | Price et al. |

FOREIGN PATENT DOCUMENTS

| | | |
|---|---|---|
| JP | 2005-253674 A | 9/2005 |
| WO | WO 2011/008672 A2 | 1/2011 |
| WO | WO 2016/015233 A1 | 2/2016 |

OTHER PUBLICATIONS

U.S. Appl. No. 15/284,837.
U.S. Appl. No. 15/284,855.
U.S. Appl. No. 15/798,902.
U.S. Appl. No. 15/798,703, filed Oct. 31, 2017.
U.S. Appl. No. 15/798,720, filed Oct. 31, 2017.
U.S. Appl. No. 15/798,835, filed Oct. 31, 2017.
U.S. Appl. No. 15/798,902, filed Oct. 31, 2017.
U.S. Appl. No. 61/410,603, filed Nov. 5, 2010.
U.S. Appl. No. 62/363,411, filed Jul. 18, 2016.
U.S. Appl. No. 62/422,698, filed Nov. 16, 2016.
U.S. Appl. No. 62/508,720, filed May 19, 2017.
U.S. Appl. No. 62/519,482, filed Jun. 14, 2017.
International Search Report and Written Opinion dated Jan. 30, 2018 for PCT/US2017/061995, 11 pgs.
International Search Report and Written Opinion dated Jun. 20, 2018 for PCT/US2017/062010, 16 pgs.
International Search Report and Written Opinion dated Apr. 13, 2018 for PCT/US2017/062016, 17 pgs.
International Search Report and Written Opinion dated Feb. 1, 2018 for PCT/US2017/062023, 13 pgs.
International Search Report and Written Opinion dated Apr. 3, 2018 for PCT/US2017/062025, 18 pgs.
U.S. Appl. No. 15/798,703.
U.S. Appl. No. 15/798,720.
U.S. Appl. No. 15/798,835.
U.S. Pat. No. 10,736,648.
European Examination Report dated Jun. 5, 2020 for Application No. EP 17812121.6, 4 pgs.
European Examination Report dated Jun. 5, 2020 for Application No. EP 17851837.9, 3 pgs.
European Examination Report dated Jun. 5, 2020 for Application No. EP 17811769.3, 3 pgs.
European Search Report, Extended, and Written Opinion dated Aug. 7, 2020 for Application No. EP 20163273.4, 7 pgs.
U.S. Patent Pub. No. 2018/0132887.
U.S. Patent Pub. No. 2018/0132888.
U.S. Patent Pub. No. 2018/0132926.
U.S. Patent Pub. No. 2018-0132884.

* cited by examiner

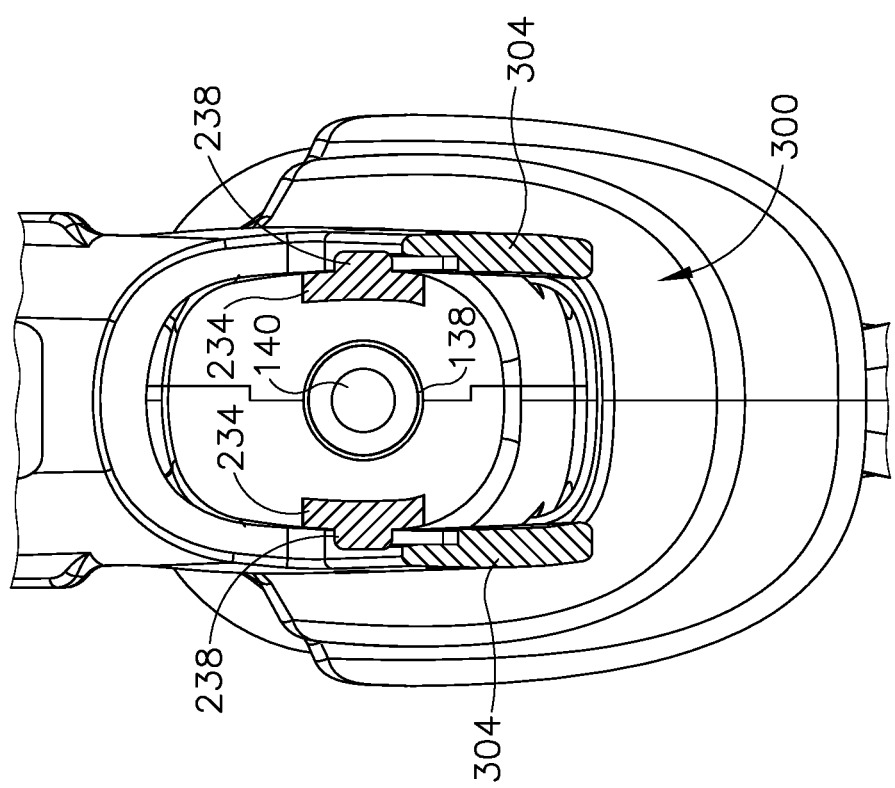

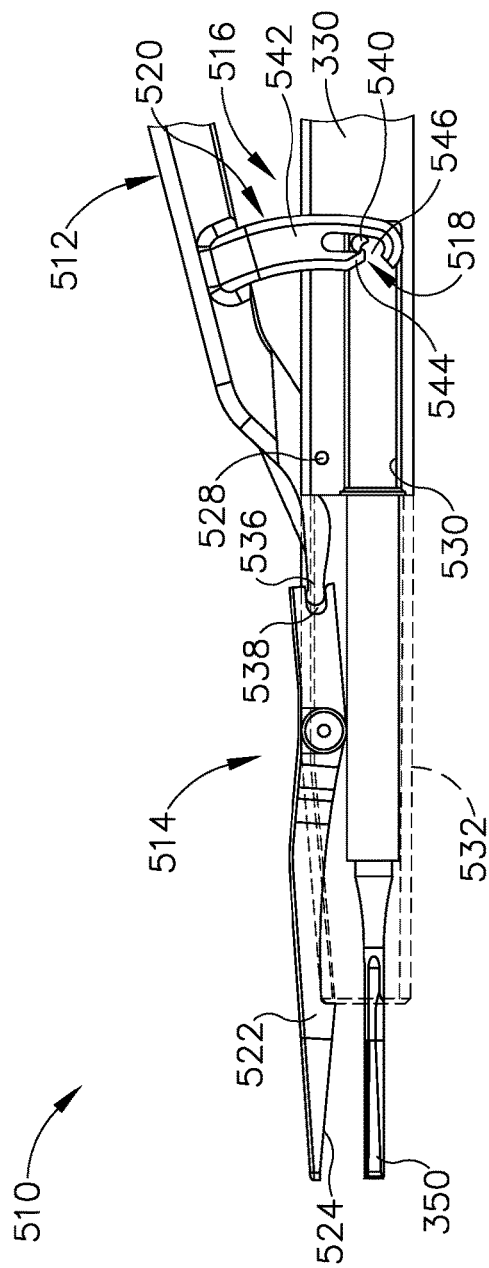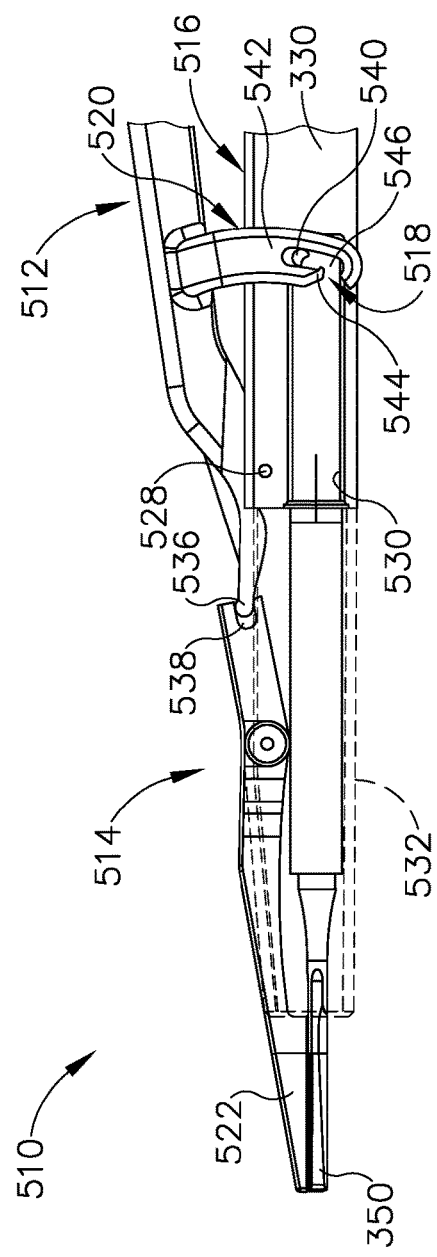

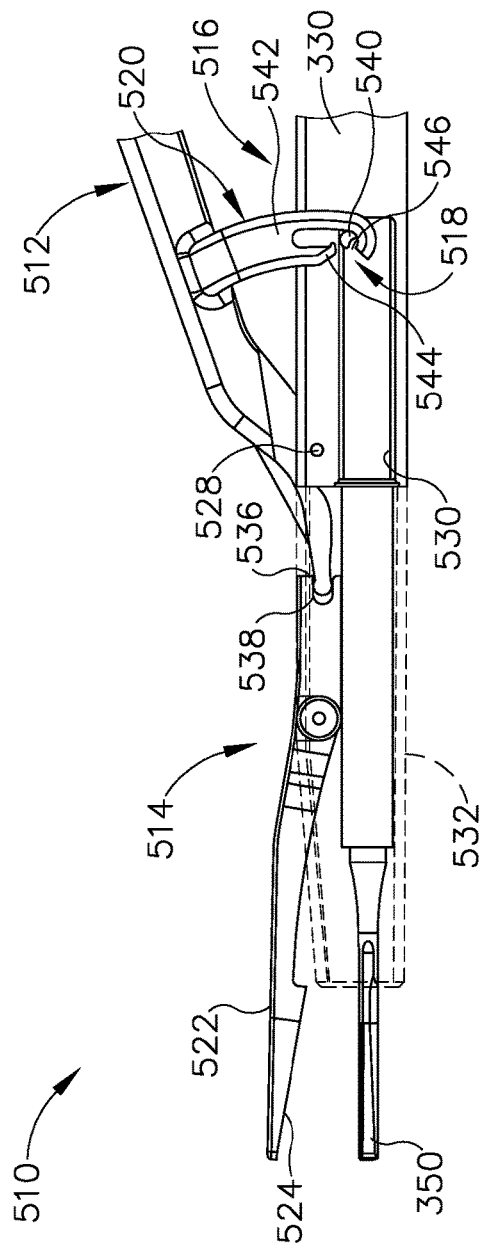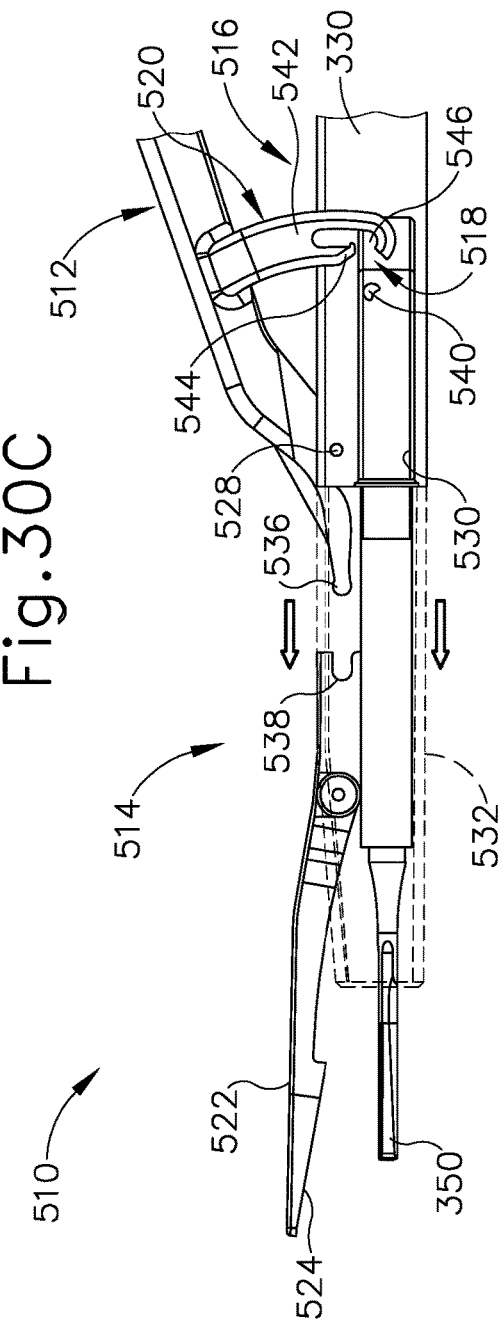

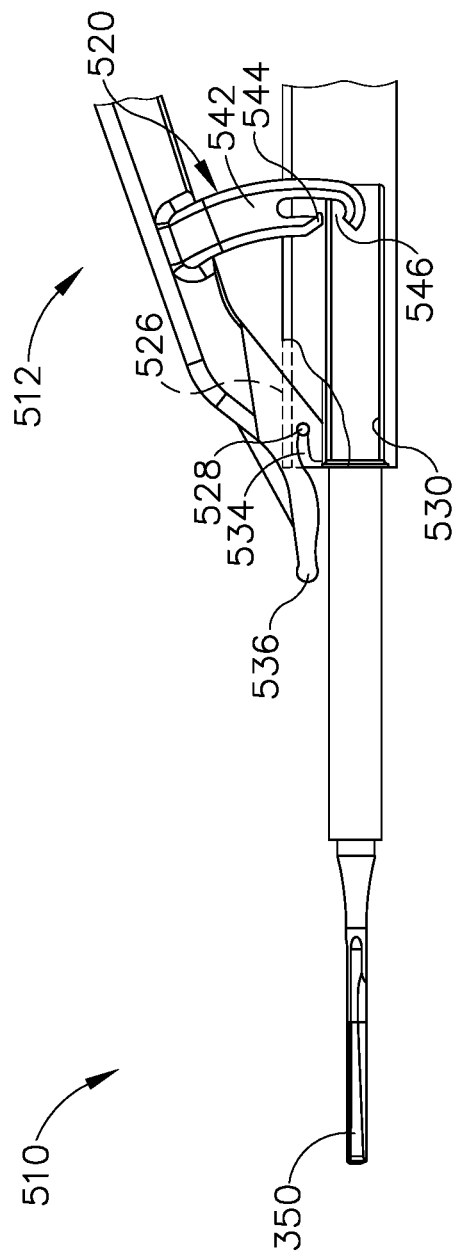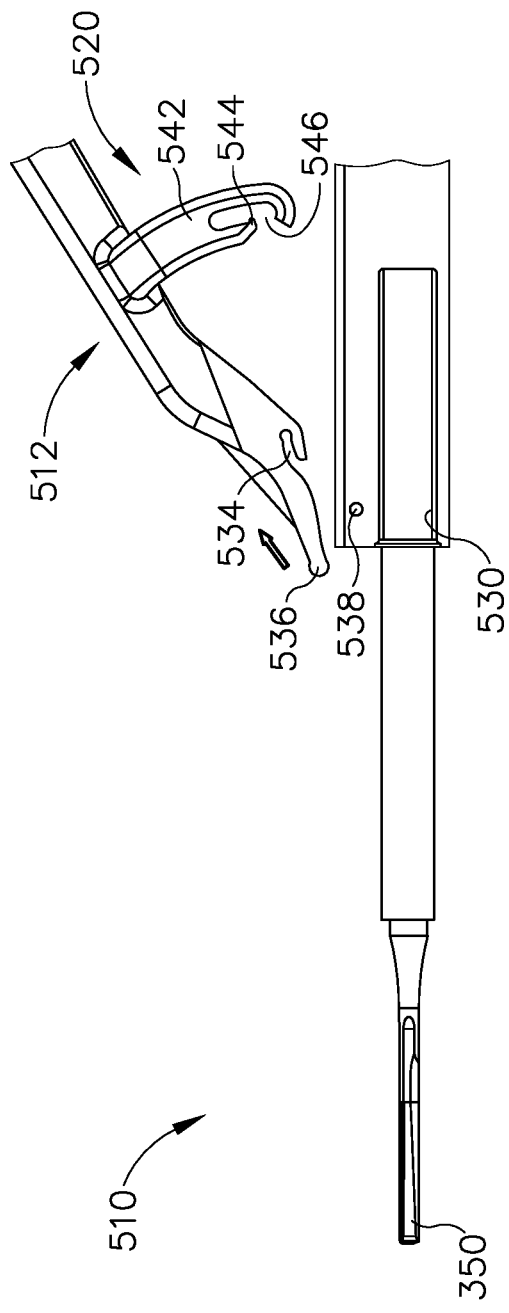

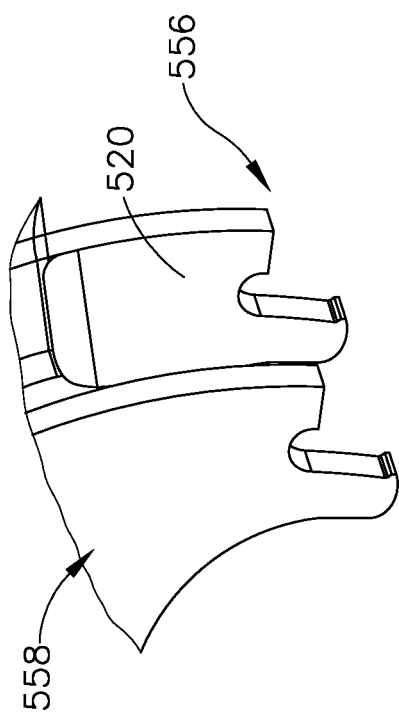
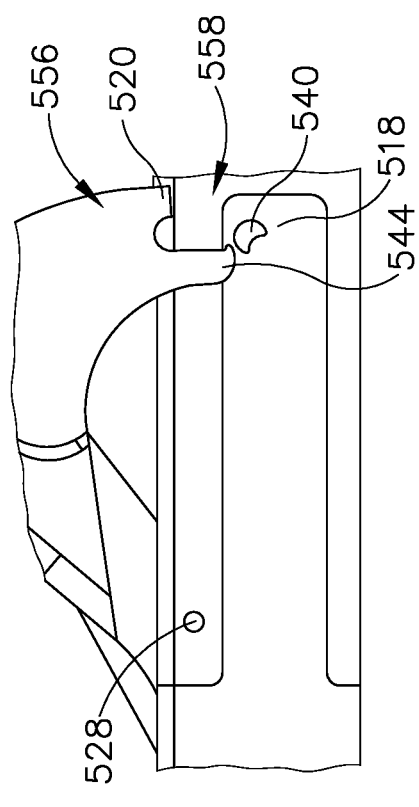
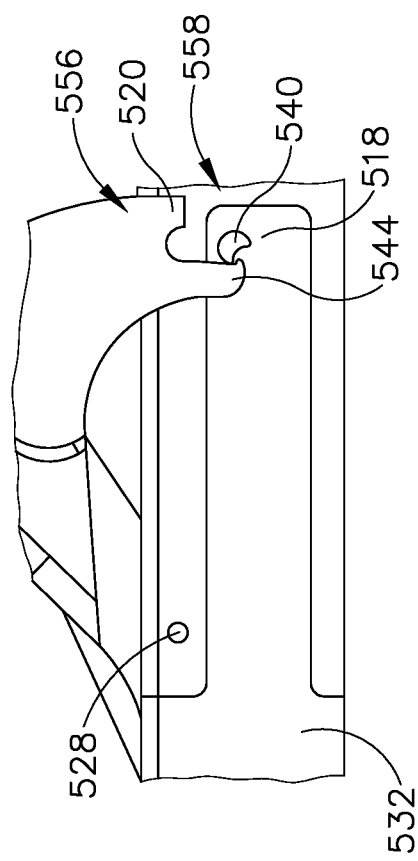
Fig.31
Fig.32A
Fig.32B

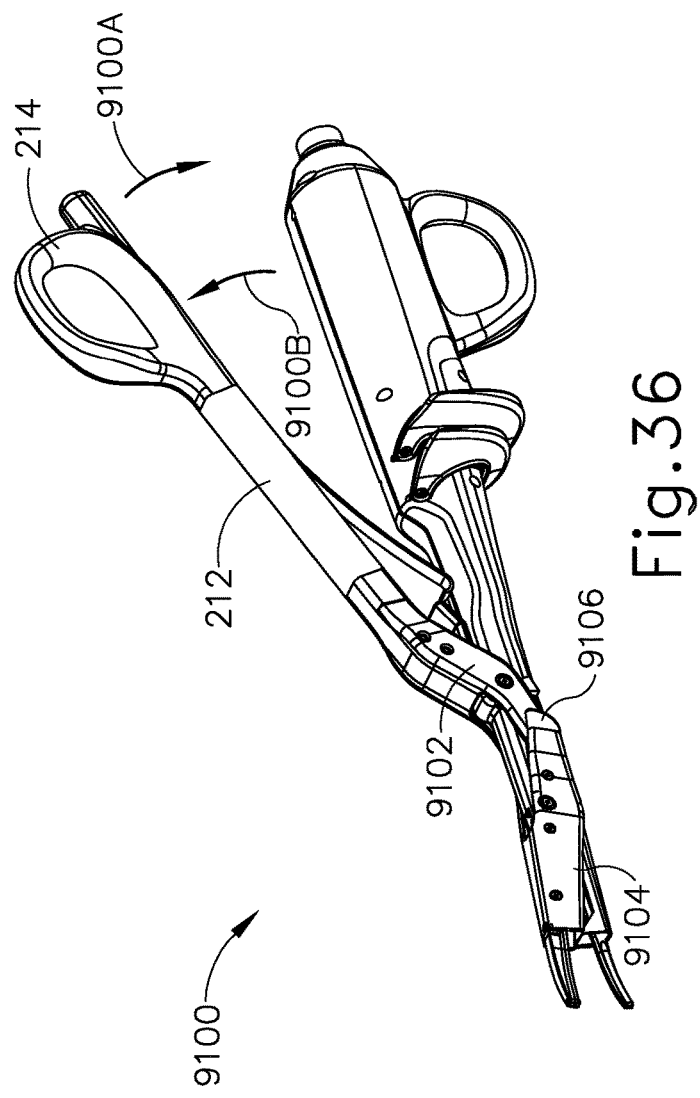
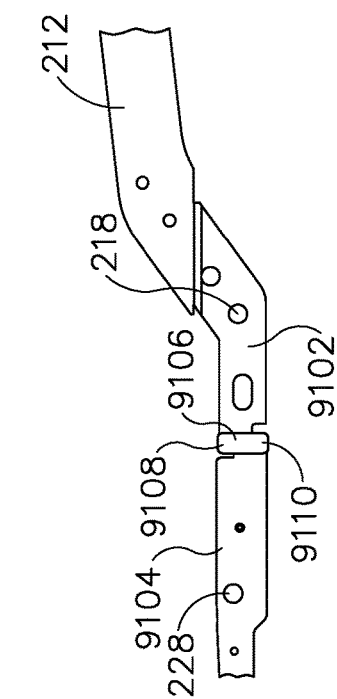
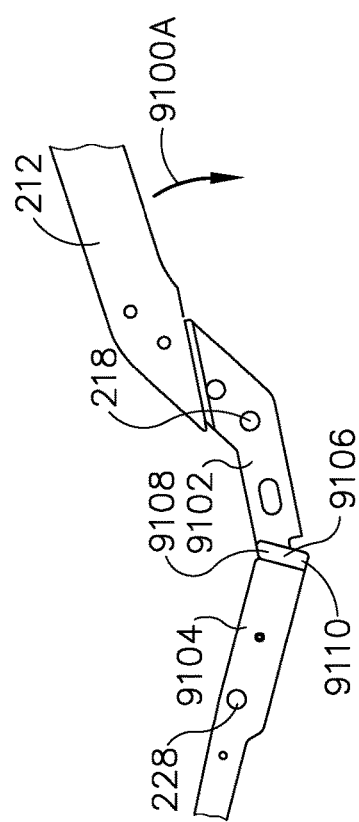
Fig.36
Fig.37
Fig.38

SURGICAL INSTRUMENT WITH REMOVABLE CLAMP ARM ASSEMBLY

PRIORITY

This application claims priority to: (1) U.S. Provisional Patent Application Ser. No. 62/422,698, filed Nov. 16, 2016, entitled "Ultrasonic Surgical Shears with Contained Compound Lever Clamp Arm Actuator," the disclosure of which is incorporated by reference herein; (2) U.S. Provisional Patent Application Ser. No. 62/508,720, filed May 19, 2017, entitled "Ultrasonic and Electrosurgical Instrument with Replaceable End Effector Features," the disclosure of which is incorporated by reference herein; and (3) U.S. Provisional Patent Application Ser. No. 62/519,482, filed Jun. 14, 2017, entitled "Ultrasonic and Electrosurgical Instrument with Removable Features," the disclosure of which is incorporated by reference herein.

BACKGROUND

A variety of surgical instruments include an end effector having a blade element that vibrates at ultrasonic frequencies to cut and/or seal tissue (e.g., by denaturing proteins in tissue cells). These instruments include piezoelectric elements that convert electrical power into ultrasonic vibrations, which are communicated along an acoustic waveguide to the blade element. The precision of cutting and coagulation may be controlled by the surgeon's technique and adjusting the power level, blade edge, tissue traction and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; and U.S. Pat. No. 6,783,524, entitled "Robotic Surgical Tool with Ultrasound Cauterizing and Cutting Instrument," issued Aug. 31, 2004, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; U.S. Pat. No. 8,623,027, entitled "Ergonomic Surgical Instruments," issued Jan. 7, 2014, the disclosure of which is incorporated by reference herein; U.S. Pat. No. 9,023,071, entitled "Ultrasonic Device for Fingertip Control," issued May 5, 2015, the disclosure of which is incorporated by reference herein; and U.S. Pat. No. 8,461,744, entitled "Rotating Transducer Mount for Ultrasonic Surgical Instruments," issued Jun. 11, 2013, the disclosure of which is incorporated by reference herein; and U.S. Pat. No. 8,591,536, entitled "Ultrasonic Surgical Instrument Blades," issued Nov. 26, 2013, the disclosure of which is incorporated by reference herein.

Some of ultrasonic surgical instruments may include a cordless transducer such as that disclosed in U.S. Pat. No. 9,381,058, entitled "Recharge System for Medical Devices," issued Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. Pat. No. 9,393,037, entitled "Surgical Instruments with Articulating Shafts," issued Jul. 19, 2016, the disclosure of which is incorporated by reference herein; and U.S. Pat. No. 9,095,367, entitled "Flexible Harmonic Waveguides/Blades for Surgical Instruments," issued Aug. 4, 2015 the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 15A depicts a cross-sectional front view of the second modular assembly of FIG. 8 inserted over the shaft assembly of FIG. 5, taken along line 15A-15A of FIG. 14B;

FIG. 30A depicts an enlarged side view of the surgical instrument of FIG. 24 in the open configuration having various components hidden for clarity;

FIG. 30B depicts the enlarged side view of the surgical instrument similar to FIG. 30A, but with the surgical instrument in the closed configuration;

FIG. 30C depicts the enlarged side view of the surgical instrument similar to FIG. 30B, but with the surgical instrument in a release configuration;

FIG. 30D depicts the enlarged side view of the surgical instrument similar to FIG. 30C, but with an end effector of the surgical instrument being removed from the handle assembly of the surgical instrument;

FIG. 30E depicts the enlarged side view of the surgical instrument similar to FIG. 30D, but with the end effector of the surgical instrument removed from the handle assembly of the surgical instrument;

FIG. 30F depicts the enlarged side view of the surgical instrument similar to FIG. 30E, but with the clamp arm actuator of the surgical instrument being removed from the handle assembly of the surgical instrument;

FIG. 31 depicts an enlarged side view of a second modular alignment release coupling with the clamp arm actuator for the surgical instrument of FIG. 24;

FIG. 32A depicts an enlarged side view of the modular alignment release coupling of FIG. 31 with the clamp arm actuator and the end effector for the surgical instrument of FIG. 24 in an open configuration;

FIG. 32B depicts the enlarged side view of the modular alignment release coupling similar to FIG. 32A, but with the surgical instrument in a release configuration;

FIG. 36 depicts a perspective view of a fourth exemplary surgical instrument, similar to the surgical instrument of FIG. 1A;

FIG. 37 depicts a side elevational view of an exemplary clamp arm of the surgical instrument of FIG. 36 indirectly coupled to an exemplary actuation arm of the surgical instrument of FIG. 36 with an exemplary link in the first position;

FIG. 38 depicts a view similar to FIG. 37, with the link in a second position;

Figure 1A:
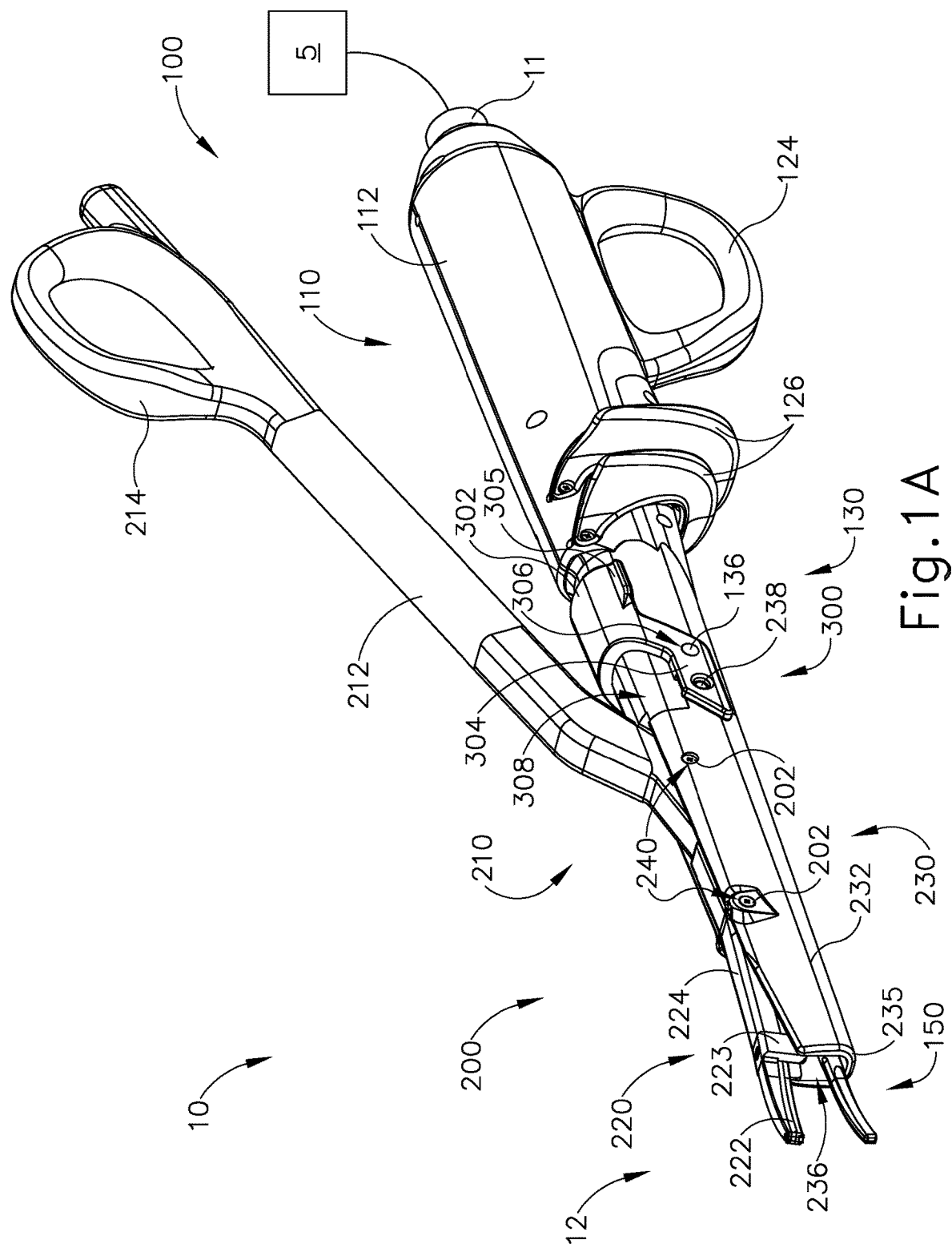
FIG. 1A depicts a perspective view of a first exemplary surgical instrument, with an end effector of the instrument in an open configuration.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "lateral," "transverse," "bottom," and "top" are relative terms to provide additional clarity to the figure descriptions provided below. The terms "upper," "lower," "lateral," "transverse," "bottom," and "top" are thus not intended to unnecessarily limit the invention described herein.

I. First Exemplary Ultrasonic Surgical Instrument for Open Surgical Procedures

FIGS. 1A-2 and FIGS. 13A-13C illustrate a first exemplary ultrasonic surgical instrument (10). At least part of instrument (10) may be constructed and operable in accordance with at least some of the teachings of U.S. Pat. Nos. 5,322,055; 5,873,873; 5,980,510; 6,325,811; 6,773,444; 6,783,524; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pat. Nos. 8,623,027; 9,023,071; 8,461,744; 9,381,058; U.S. Pub. No. 2012/0116265, now abandoned; U.S. Pat. Nos. 9,393,037; 9,095,367; U.S. Pat. App. No. 61/410,603; and/or U.S. Pub. No. 2015/0080924, issued as U.S. Pat. No. 10/172,636 on Jan. 8, 2019. The disclosures of each of the foregoing patents, publications, and applications are incorporated by reference herein. In addition, or in the alternative, at least part of instrument (10) may be constructed and operable in accordance with at least some of the teachings of U.S. Pub. No. 2017/0105755, entitled "Surgical Instrument with Dual Mode End Effector and Compound Lever with Detents," published Apr. 20, 2017, issued as U.S. Pat. No. 11,020,200 on Jun. 1, 2021, the disclosure of which is incorporated by reference herein; and/or U.S. Pat. App. No. 62/363,411, entitled "Surgical Instrument with Dual Mode End Effector," filed Jul. 18, 2016, the disclosure of which is incorporated by reference herein.

As described in greater detail below, instrument (10) is operable to cut tissue and seal or weld tissue (e.g., a blood vessel, etc.) substantially simultaneously. It should also be understood that instrument (10) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instrument (10) may have various structural and functional similarities with the devices taught in any of the other references that are cited and incorporated by reference herein.

Figure 1B:
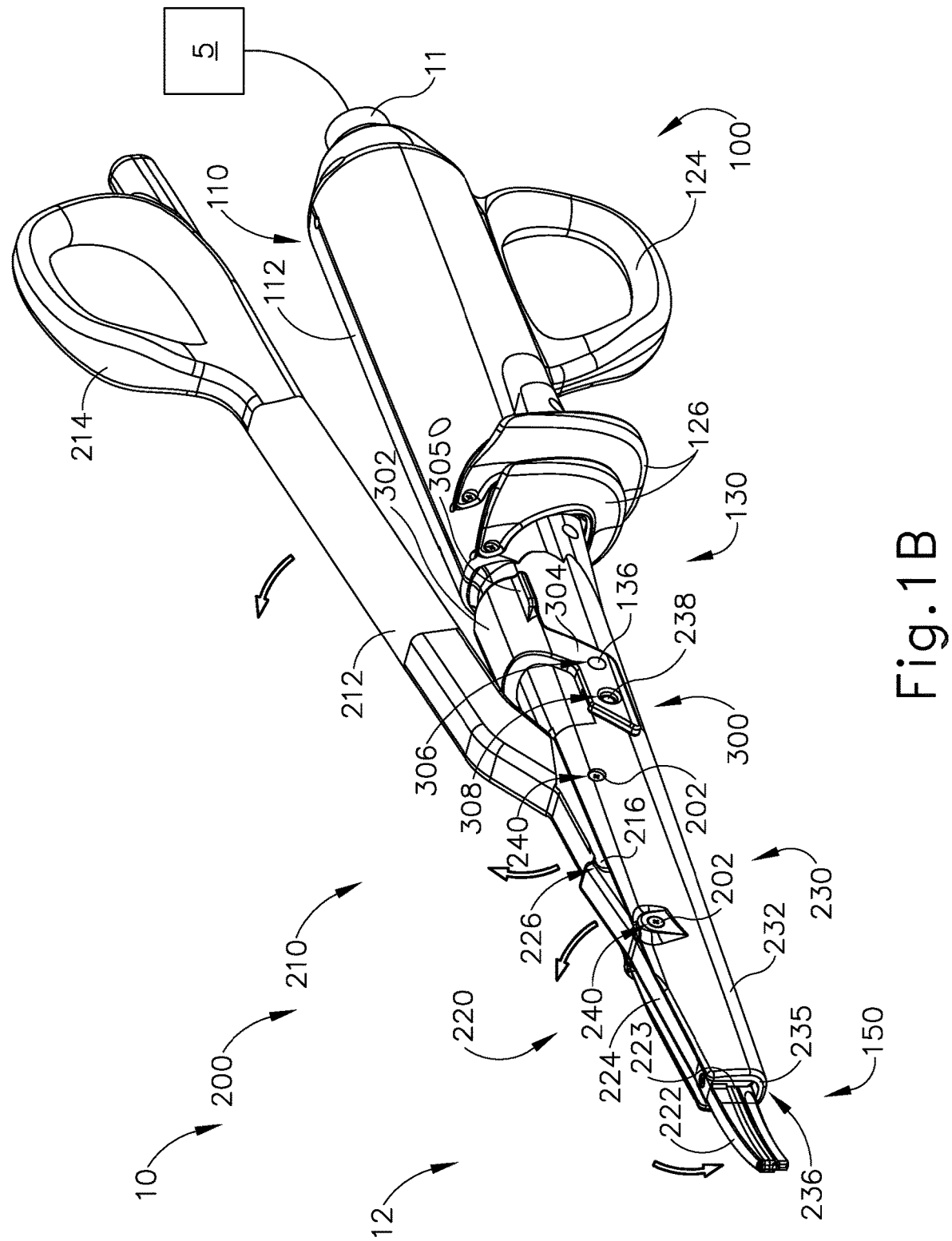
FIG. 1B depicts a perspective view of the instrument of FIG. 1A, with the end effector in a closed configuration.
Figure 2:
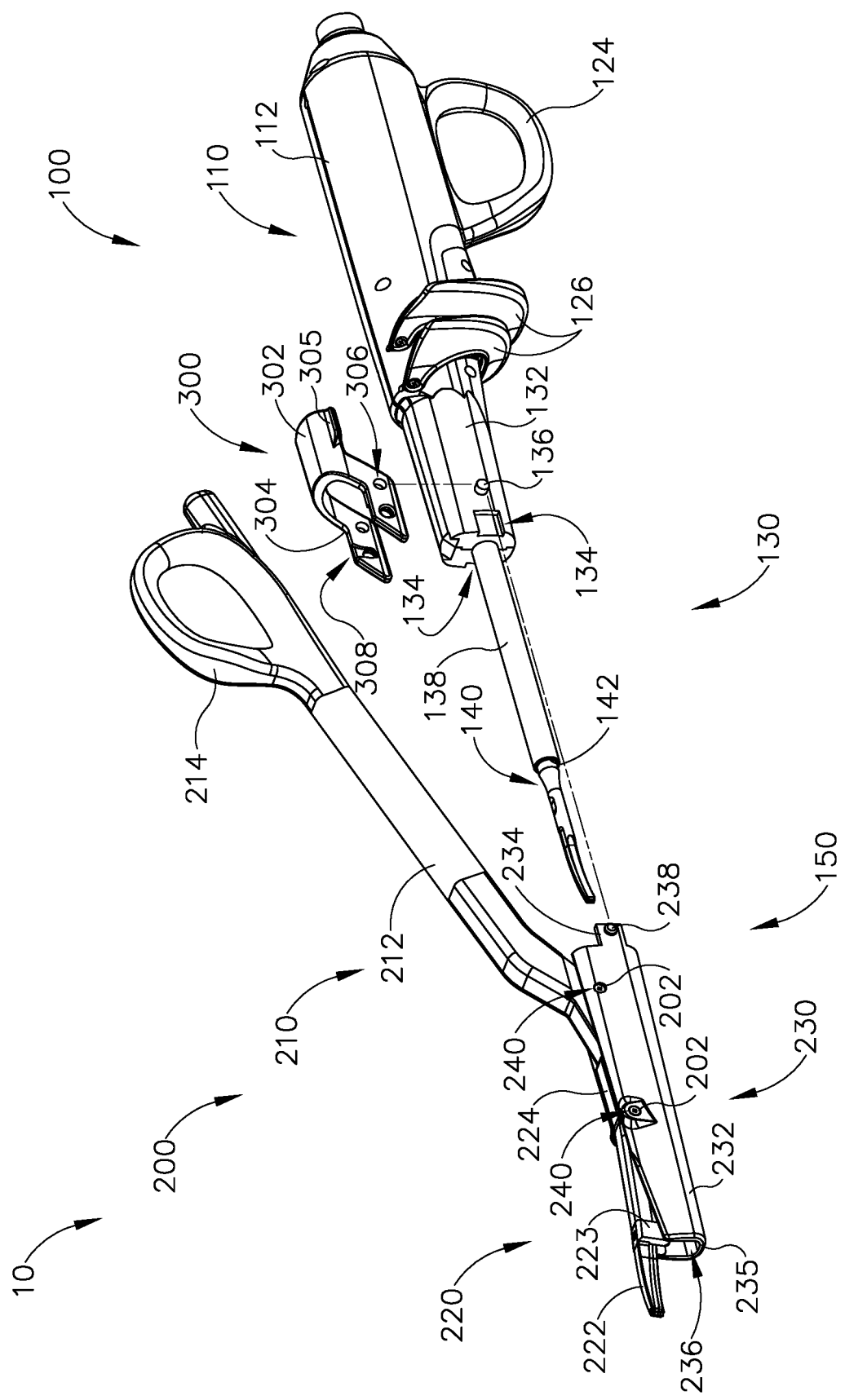
FIG. 2 depicts an exploded perspective view of the instrument of FIG. 1A.
Figure 3:
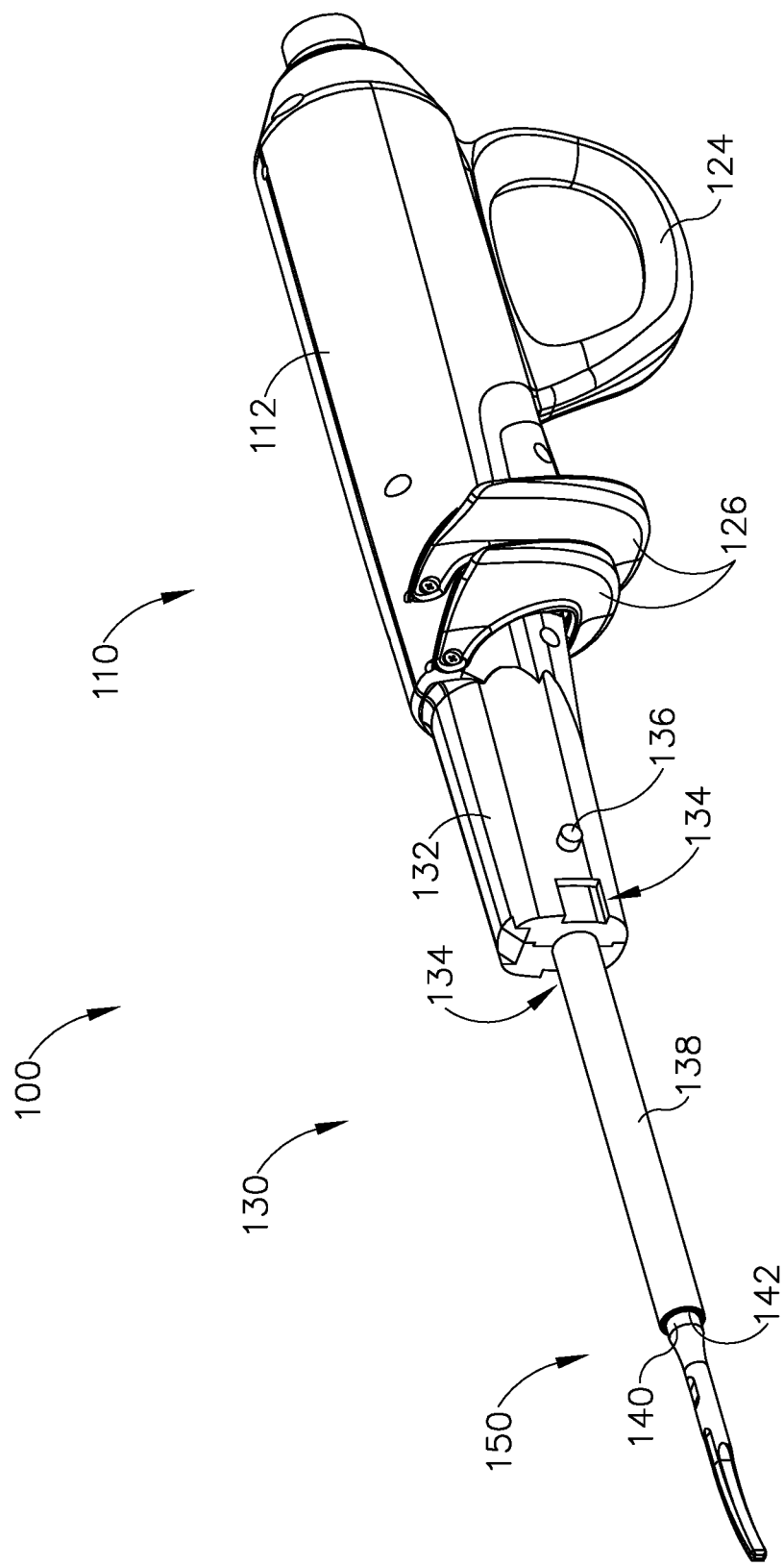
FIG. 3 depicts a perspective view of a first modular assembly of the instrument of FIG. 1A.

Instrument (10) in the present example includes a first modular assembly (100), a second modular assembly (200), and a coupling member (300). As will be described in greater detail below, coupling member (300) may selectively attach first modular assembly (100) with second modular assembly (200) in order to form instrument (10) with an end effector (12). As best seen in FIGS. 1A-1B, end effector (12) comprises an ultrasonic blade (150) and a clamp pad (222) of a clamp pad assembly (220).

Figure 16A:
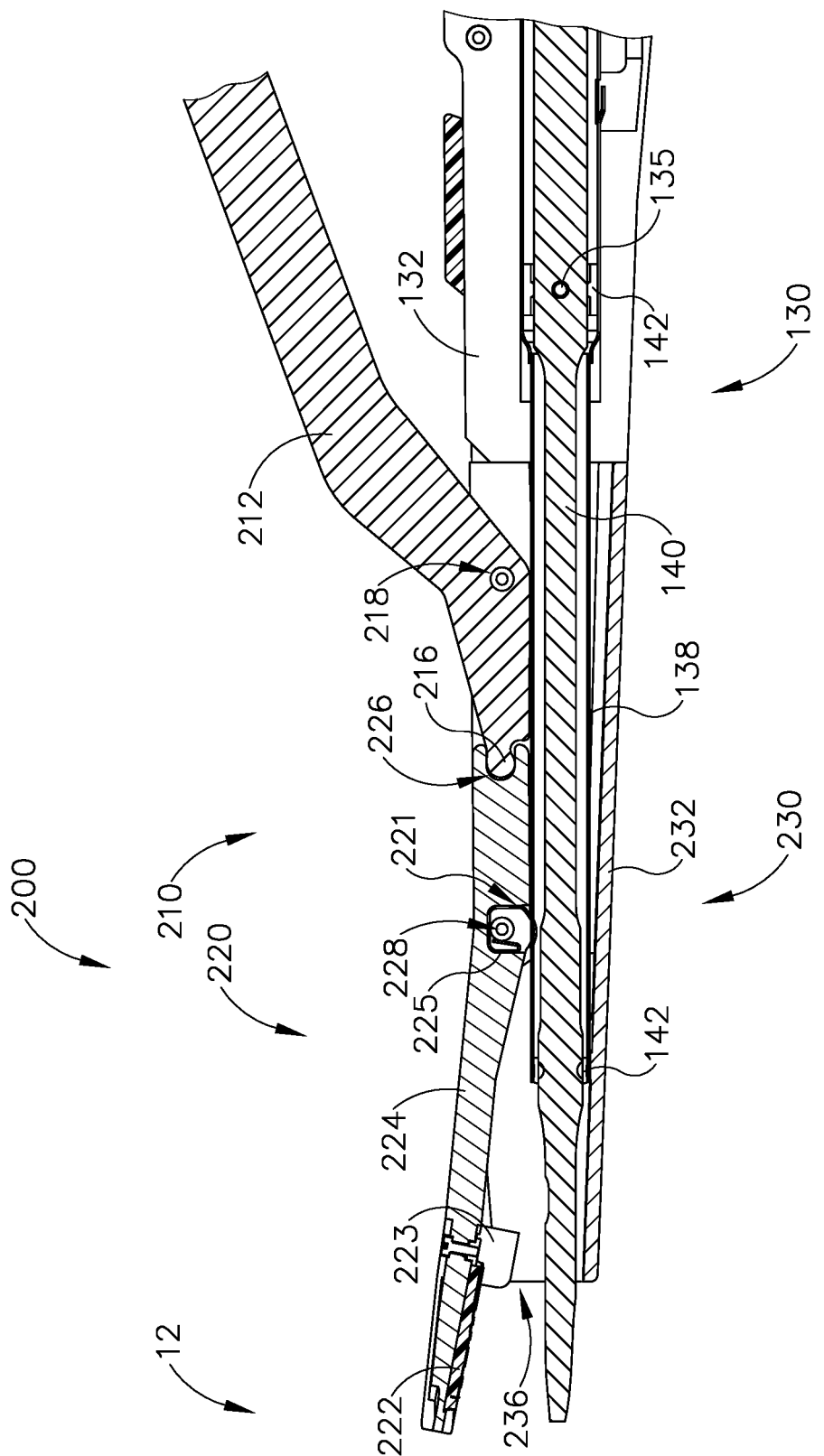
FIG. 16A depicts a cross-sectional side view of the second modular assembly of FIG. 8 coupled with the shaft assembly of FIG. 5, where the end effector is in an open configuration.
Figure 16B:
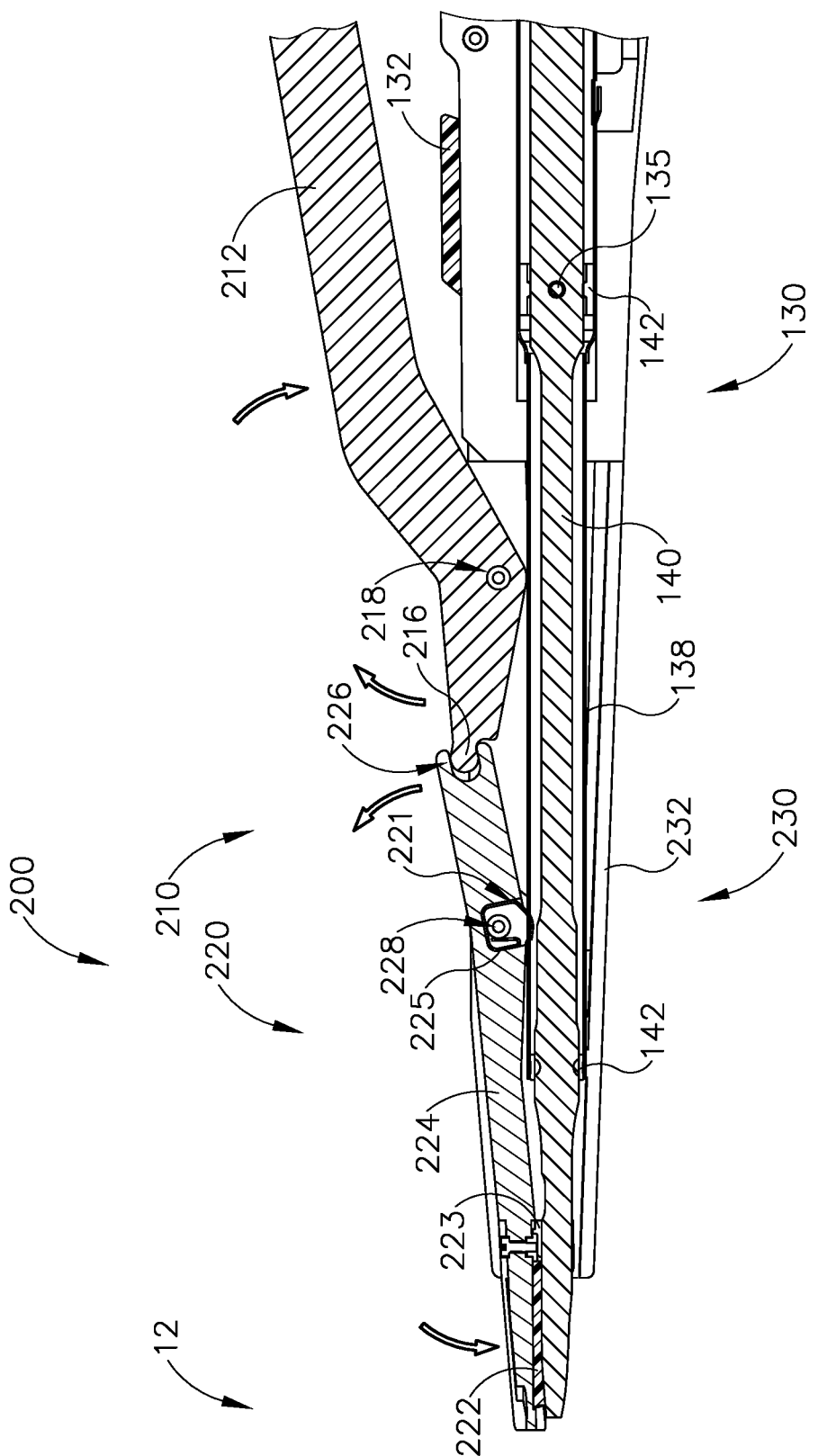
FIG. 16B depicts a cross-sectional side view of the second modular assembly of FIG. 8 coupled with the shaft assembly of FIG. 5, where the end effector is in a closed configuration.

Additionally, as will be described in greater detail below, selected portions of second modular assembly (200) may actuate relative to first modular assembly (100), when properly attached with each other, in order to actuate end effector (12) from an open configuration (FIGS. 1A and 16A), to a closed configuration (FIGS. 1B and 16B). The ability to selectively attach and detach second modular assembly (200) with first modular assembly (100) may provide additional benefits of reusability of either modular assembly (100, 200). For instance, different kinds of first modular assemblies (100) may be used with second modular assembly (200) to provide different kinds of surgical instruments. Similarly, different kinds of second modular assemblies (200) may be used with first modular assembly (100) to provide different kinds of surgical instruments. Additionally, moving components of second modular assembly (200) may be housed within static components of second modular assembly (200), which may provide additional advantages, some of which are described below while others will be apparent to one having ordinary skill in the art in view of the teachings herein.

First modular assembly (100) includes a handle assembly (110), a shaft assembly (130) extending distally from handle assembly (110), and an ultrasonic blade (150) extending distally from shaft assembly (130). Handle assembly (110) includes a body (112), a finger grip ring (124), a pair of buttons (126) distal to finger grip ring (124), and an ultrasonic transducer assembly (30) housed within body (112).

Shaft assembly (130) includes a proximal outer sheath (132) extending distally from body (112), a tube (138) extending distally from proximal outer sheath (132), and a waveguide (140) extending within and through both proximal outer sheath (132) and tube (138). Proximal outer sheath (132) includes a pair of protrusions (136). Additionally, proximal outer sheath (132) defines a pair of recesses (134). As will be described in greater detail below, recesses (134) are dimensioned to mate with a portion of distal outer sheath (230) while protrusions (136) are configured to pivotally couple proximal outer sheath (132) with coupling member (300). Both recesses (134) and protrusions (136) may help couple first modular assembly (100) with coupling member (300).

Proximal outer sheath (132) may be fixed relative to body (112), while tube (138) may be fixed relative to proximal outer sheath (132). As will be described in greater detail below, waveguide (140) may attach to transducer assembly (30) and be supported by portions proximal outer sheath (132) and tube (138). Ultrasonic blade (150) may be unitarily connected to waveguide (140), and also extend distally from waveguide (140). As will be described in greater detail below, waveguide (140) is operable to connect to ultrasonic transducer assembly (30) in order to provide acoustic communication between ultrasonic blade (150) and transducer assembly (30).

Figure 4:
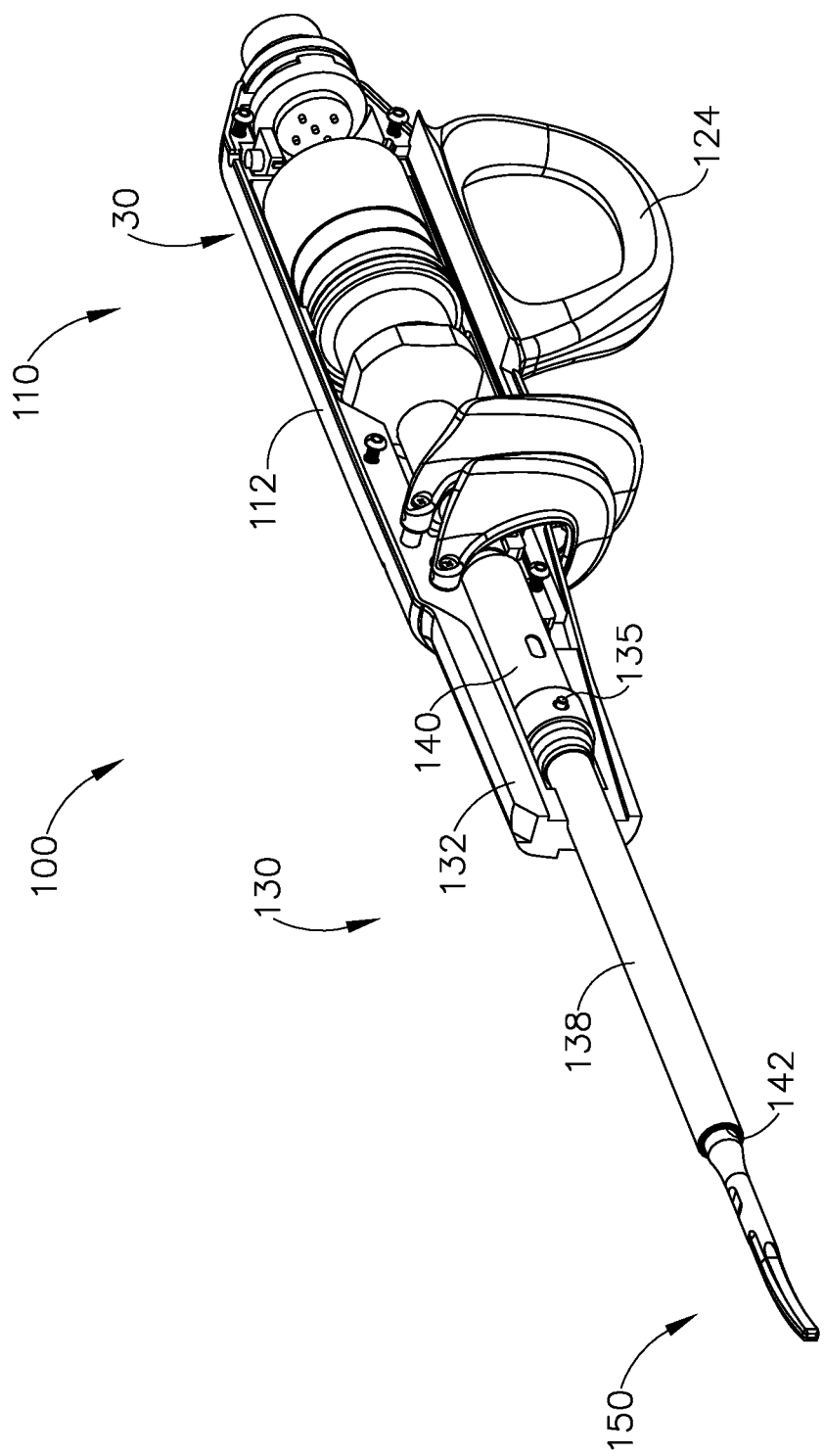
FIG. 4 depicts a perspective view of the first modular assembly of FIG. 3, with selected portions purposefully omitted for clarity.
Figure 5:
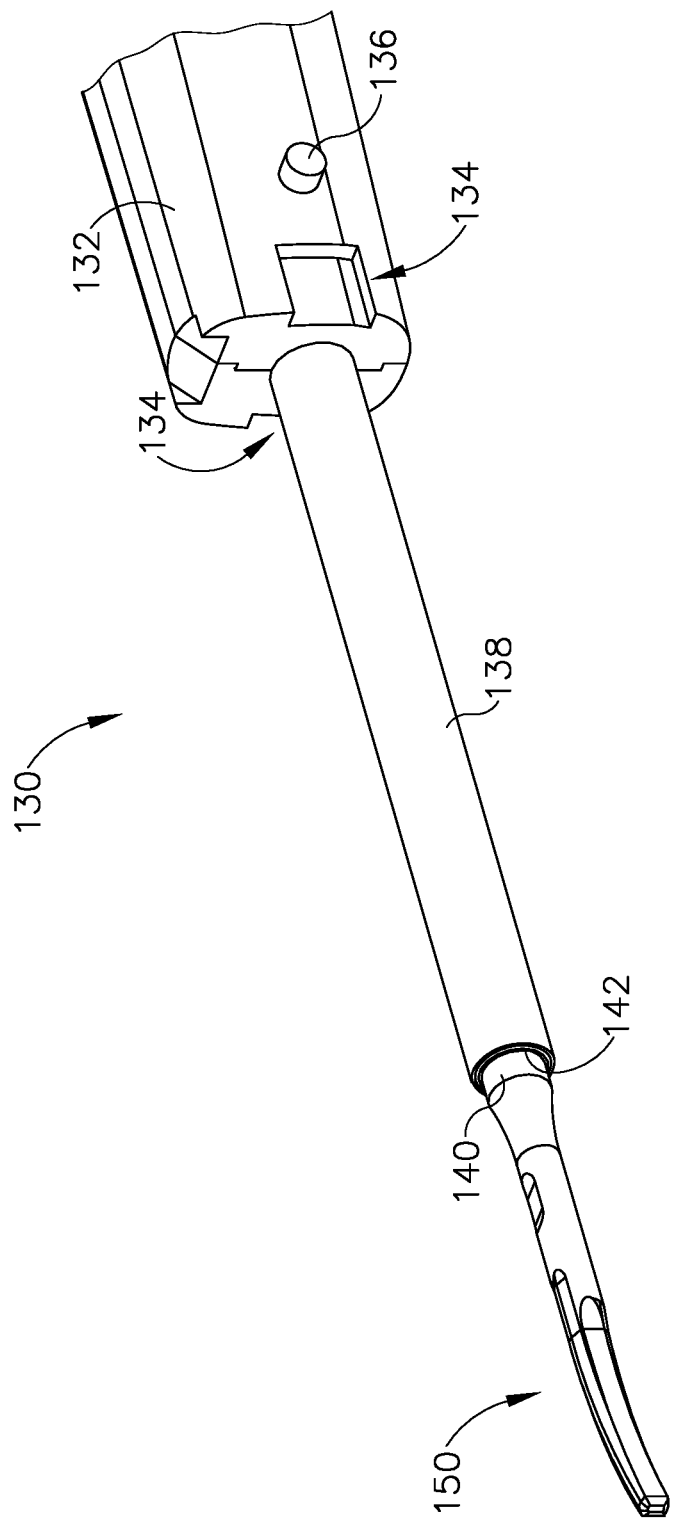
FIG. 5 depicts a perspective view of a shaft assembly and a blade assembly of the first modular assembly of FIG. 3.
Figure 6:
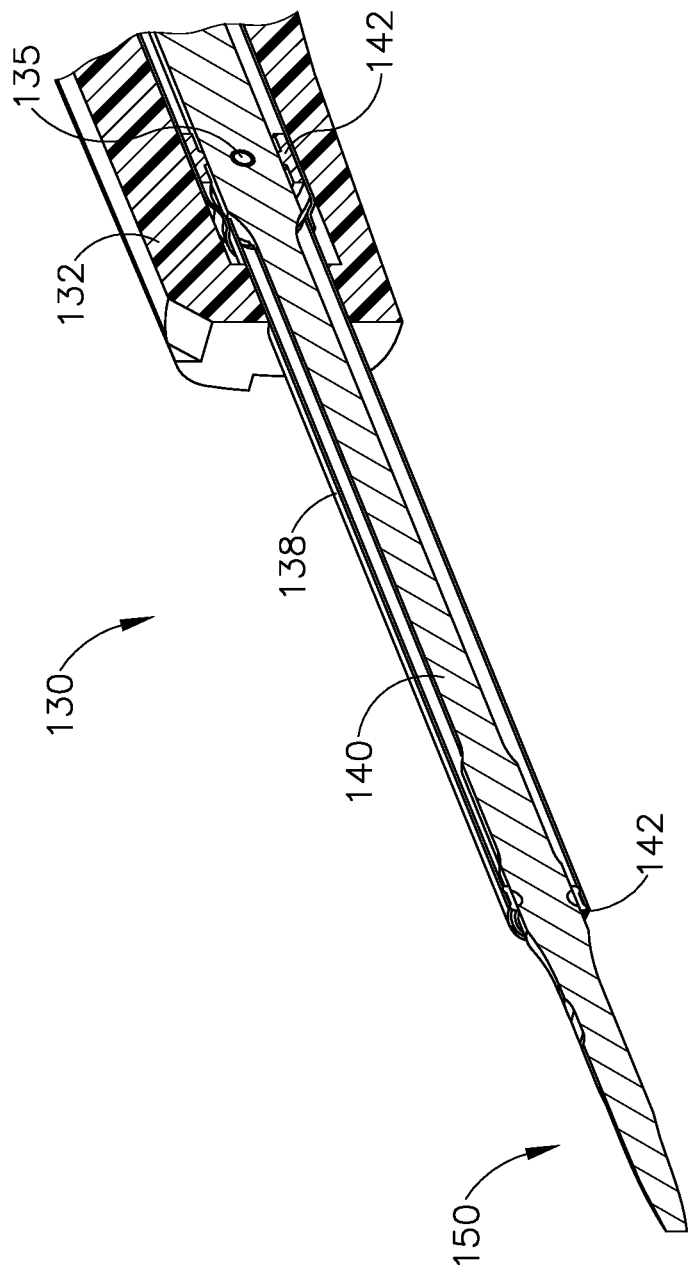
FIG. 6 depicts a cross-sectional perspective view of the shaft assembly and blade assembly of FIG. 5.

Referring to FIG. 4, ultrasonic transducer assembly (30) is housed within body (112) of handle assembly (110). As seen in FIGS. 1A-1B, transducer assembly (30) is coupled with a generator (5) via a plug (11). Transducer assembly (30) receives electrical power from generator (5) and converts that power into ultrasonic vibrations through piezoelectric principles. Generator (5) may include a power source and control module that is configured to provide a power profile to transducer assembly (30) that is particularly suited for the generation of ultrasonic vibrations through transducer assembly (30). Generator (5) may also be configured to provide a power profile that enables end effector (12) to apply RF electrosurgical energy to tissue.

By way of example only, generator (5) may comprise a GEN 300 sold by Ethicon Endo-Surgery, Inc. of Cincinnati, Ohio. In addition or in the alternative, generator (not shown) may be constructed in accordance with at least some of the teachings of U.S. Pat. No. 8,986,302, entitled "Surgical Generator for Ultrasonic and Electrosurgical Devices," issued Mar. 24, 2015, the disclosure of which is incorporated by reference herein. It should also be understood that at least some of the functionality of generator (5) may be integrated into handle assembly (110), and that handle assembly (110) may even include a battery or other on-board power source such that plug (11) is omitted. Still other suitable forms that generator (5) may take, as well as various features and operabilities that generator (5) may provide, will be apparent to those of ordinary skill in the art in view of the teachings herein.

Ultrasonic vibrations that are generated by transducer assembly (30) are communicated along acoustic waveguide (140) when properly coupled. Waveguide (140) is mechanically and acoustically coupled with transducer assembly (30). Waveguide (140) extends through shaft assembly (130) to reach ultrasonic blade (150). Waveguide (140) may be secured to proximal outer sheath (132) and/or body (112) via a pin (135) extending through waveguide (140) and proximal outer sheath (132). Pin (135) may help ensure waveguide (140) remains longitudinally and rotationally fixed relative to the rest of shaft assembly (130) when waveguide (140) is in a deactivated state (i.e. not vibrating ultrasonically).

Additionally, waveguide (140) may be supported by tube (138) via seals (142) located between an interior of tube (138) and an exterior of waveguide (140). Seals (142) may also prevent unwanted matter and fluid from entering portions of tube (138) housing waveguide (140). Pin (135) and seals (142) are located at positions along the length of waveguide (140) corresponding to nodes associated with resonant ultrasonic vibrations communicated through waveguide (140). Therefore, contact between waveguide (140) and pin (135), as well as contact between waveguide (140) and seals (142) may not affect ultrasonic vibrations communicated through waveguide (154).

When ultrasonic blade (150) is in an activated state (i.e., vibrating ultrasonically), ultrasonic blade (150) is operable to effectively cut through and seal tissue, particularly when the tissue is being clamped between clamp pad (222) and ultrasonic blade (150). It should be understood that waveguide (140) may be configured to amplify mechanical vibrations transmitted through waveguide (140). Furthermore, waveguide (140) may include features operable to control the gain of the longitudinal vibrations along waveguide (140) and/or features to tune waveguide (140) to the resonant frequency of the system.

In the present example, the distal end of ultrasonic blade (150) is located at a position corresponding to an anti-node associated with resonant ultrasonic vibrations communicated through waveguide (140), in order to tune the acoustic assembly to a preferred resonant frequency $f_o$ when the acoustic assembly is not loaded by tissue. When transducer assembly (30) is energized, the distal end of ultrasonic blade (150) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (30) of the present example is activated, these mechanical oscillations are transmitted through the waveguide to (140) reach ultrasonic blade (150), thereby providing oscillation of ultrasonic blade (150) at the resonant ultrasonic frequency. Thus, when tissue is secured between ultrasonic blade (150) and clamp pad (222), the ultrasonic oscillation of ultrasonic blade (150) may simultaneously sever the tissue and denature the proteins in adjacent tissue cells, thereby providing a coagulative effect with relatively little thermal spread.

In some versions, an electrical current may also be provided through ultrasonic blade (150) and/or clamp pad (222) to also seal the tissue. It should therefore be understood that instrument (10) may also be configured to provide radiofrequency (RF) energy to a surgical site via end effector (12). By way of example only, an operator may rely mainly on the use of ultrasonic energy from blade (150) to sever tissue that is captured between ultrasonic blade (150) and clamp pad (222). The operator may further rely on the use of RF energy from end effector (12) to seal the severed tissue. Of course, it will be understood that the ultrasonic energy from blade (150) may seal tissue to some degree, such that the RF energy from end effector (12) may supplement the sealing that would already be provided from the ultrasonic energy. It will also be understood that there may be instances where the operator may wish to simply use end effector (12) to only apply RF energy to tissue, without also applying ultrasonic energy to tissue. As will be appreciated from the description herein, some versions of instrument (10) are capable of providing all of the above noted kinds of functionality. Various ways in which instrument (10) may be configured and operable to provide both ultrasonic and RF electrosurgical modes of operation are described in various references cited herein; while other ways in which instrument (10) may be configured and operable to provide both ultrasonic and RF electrosurgical modes of operation will be apparent to those of ordinary skill in the art in view of the teachings herein.

An operator may activate buttons (126) to selectively activate transducer assembly (30) to thereby activate ultrasonic blade (150). In the present example, two buttons (126) are provided. In some versions, one button (126) is provided for activating ultrasonic blade (150) at a first power profile (e.g., a first frequency and/or first amplitude) and another button (126) is provided for activating ultrasonic blade (150) at a second power profile (e.g., a second frequency and/or second amplitude). In some other versions, one button (126) is provided for activating ultrasonic blade (150) with ultrasonic energy, and the other button (126) is provided for activating end effector (12) with RF energy. In some other versions, one button (126) is operable to activate ultrasonic blade (150) with ultrasonic energy while simultaneously activating end effector (12) with RF energy; while the other button (126) is only operable to activate ultrasonic blade (150) with ultrasonic energy. In some other versions, at least one button (126) is operable to initially activate ultrasonic blade (150) with ultrasonic energy, then based on one or more other conditions (e.g., time, measured impedance, etc.) while button (126) remains activated, eventually activating end effector (12) with RF energy while still activating ultrasonic blade (150) with ultrasonic energy. In some other versions, at least one button (126) is operable to initially activate ultrasonic blade (150) with ultrasonic energy, then based on one or more other conditions (e.g., time, measured impedance, etc.) while button (126) remains activated, eventually activating end effector (12) with RF energy while ceasing activation of ultrasonic blade (150) with ultrasonic energy. In some other versions, at least one button (126) is operable to initially activate end effector (12) with RF energy, then based on one or more other conditions (e.g., time, measured impedance, etc.) while button (126) remains activated, eventually activating ultrasonic blade (150) with ultrasonic energy while ceasing activation of end effector (12) with RF energy.

It should be understood that any other suitable number of buttons and/or otherwise selectable power levels and/or power modalities may be provided. For instance, a foot pedal may be provided to selectively activate transducer assembly (30).

Buttons (126) of the present example are positioned such that an operator may readily fully operate instrument (10) with a single hand. For instance, when first and second modular assemblies (100, 200) are coupled, the operator may position their thumb in thumb grip ring (214), position their ring finger in finger grip ring (124), position their middle finger about body (112), and manipulate buttons (126) using their index finger. Of course, any other suitable techniques may be used to grip and operate instrument (10); and buttons (126) may be located at any other suitable positions.

Figure 7:
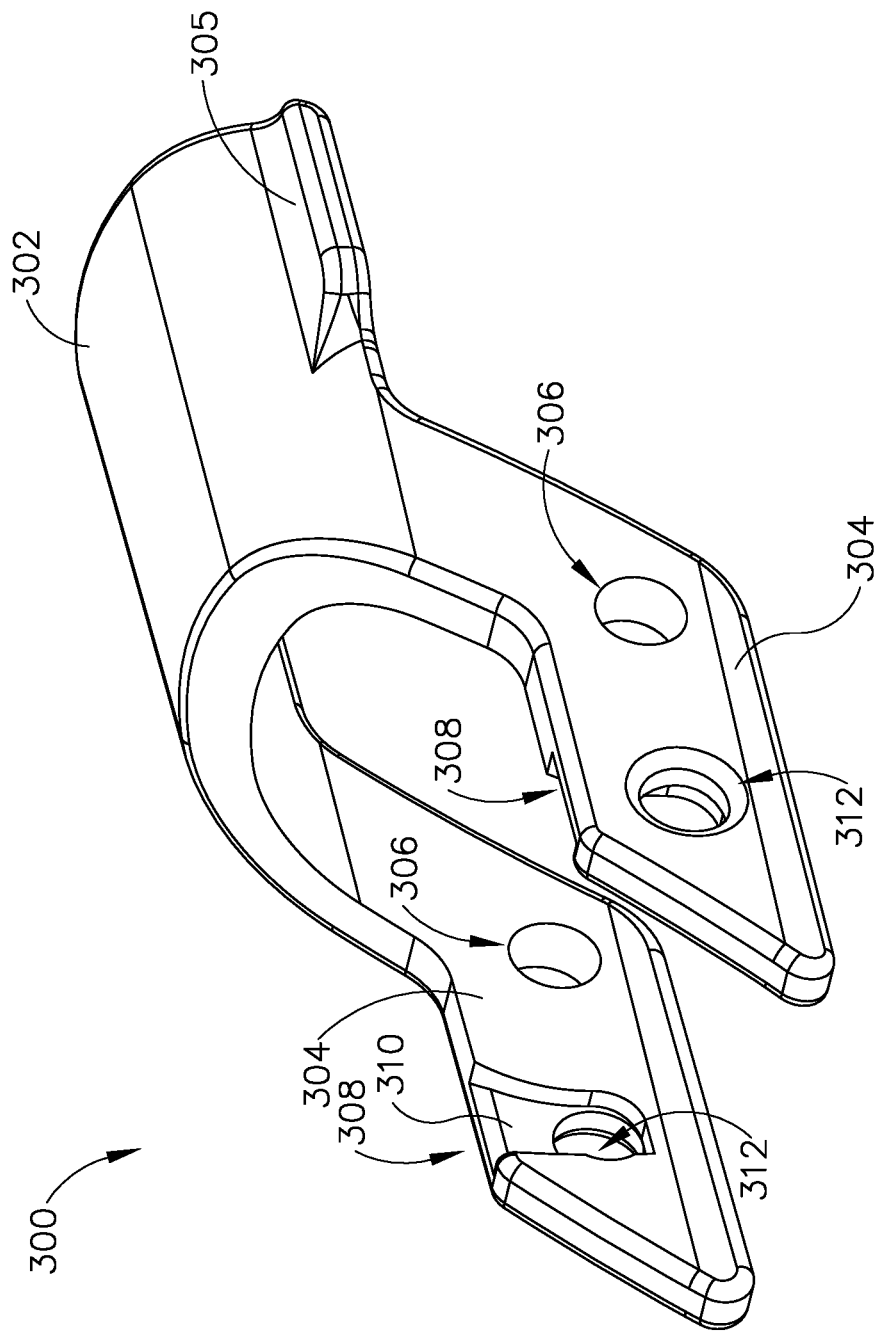
FIG. 7 depicts a perspective view of a coupling member of the instrument of FIG. 1A.
Figure 8:
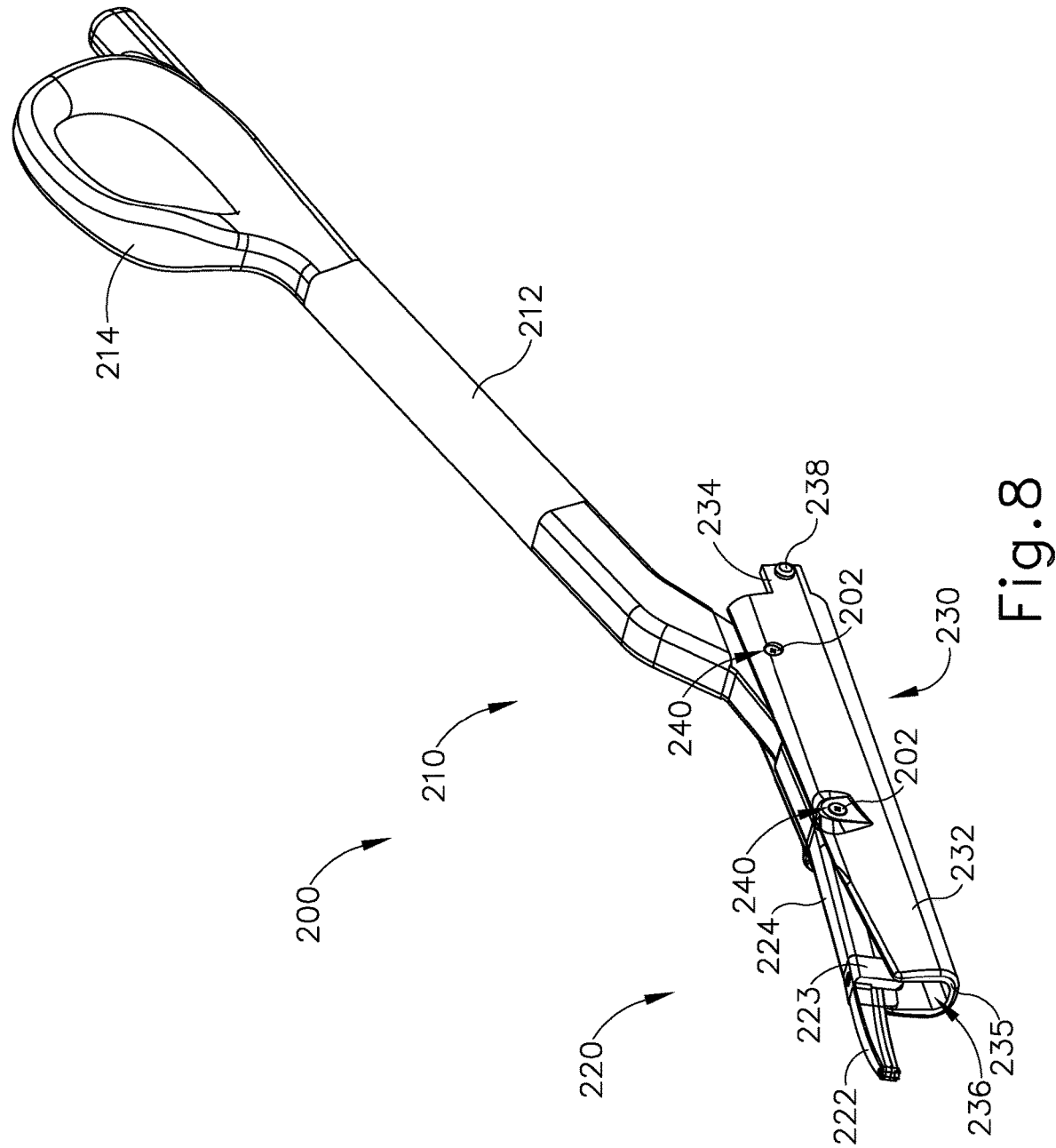
FIG. 8 depicts a perspective view of a second modular assembly of the instrument of FIG. 1A.
Figure 9:
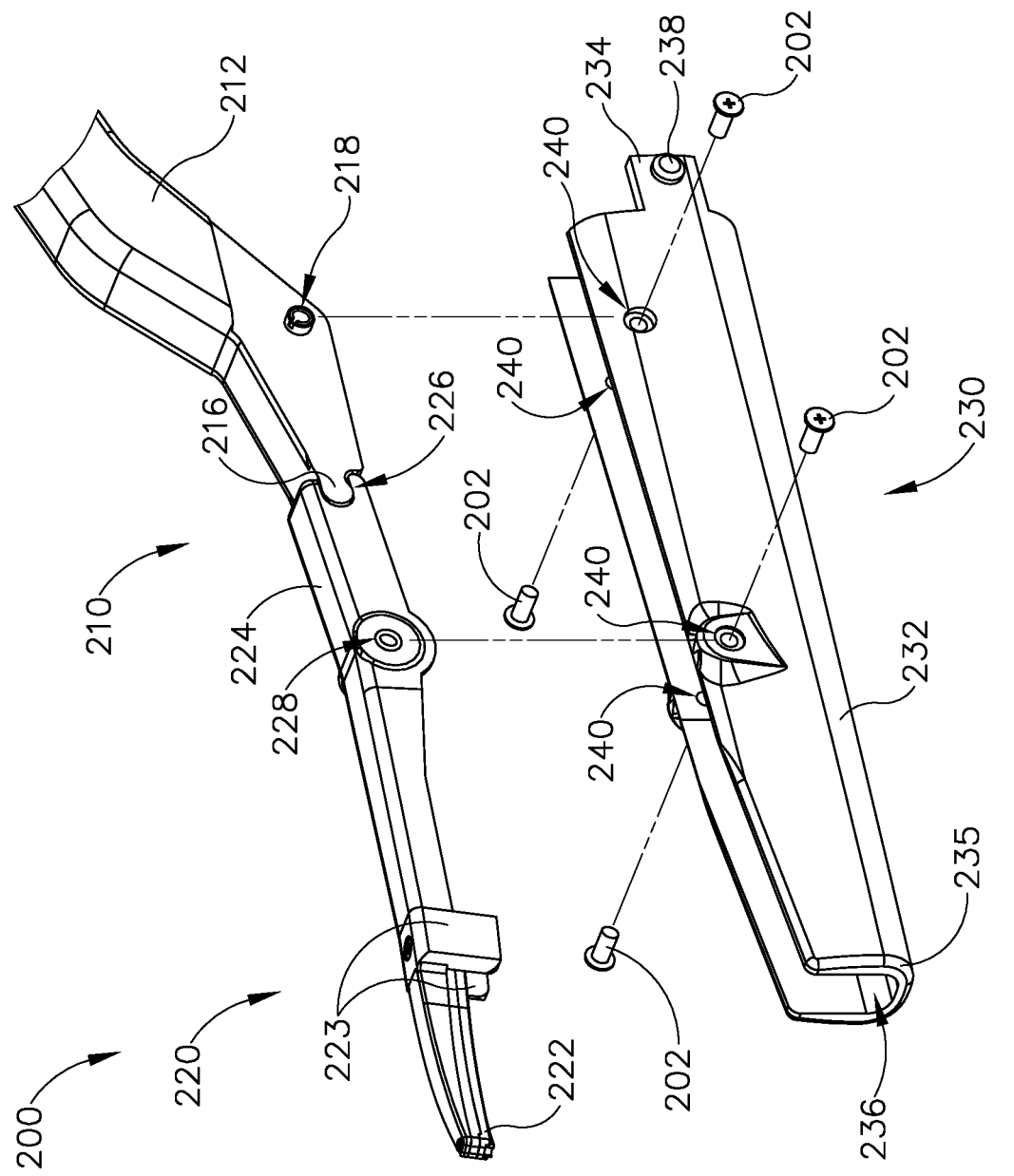
FIG. 9 depicts an exploded perspective view of the second modular assembly of FIG. 8.
Figure 10:
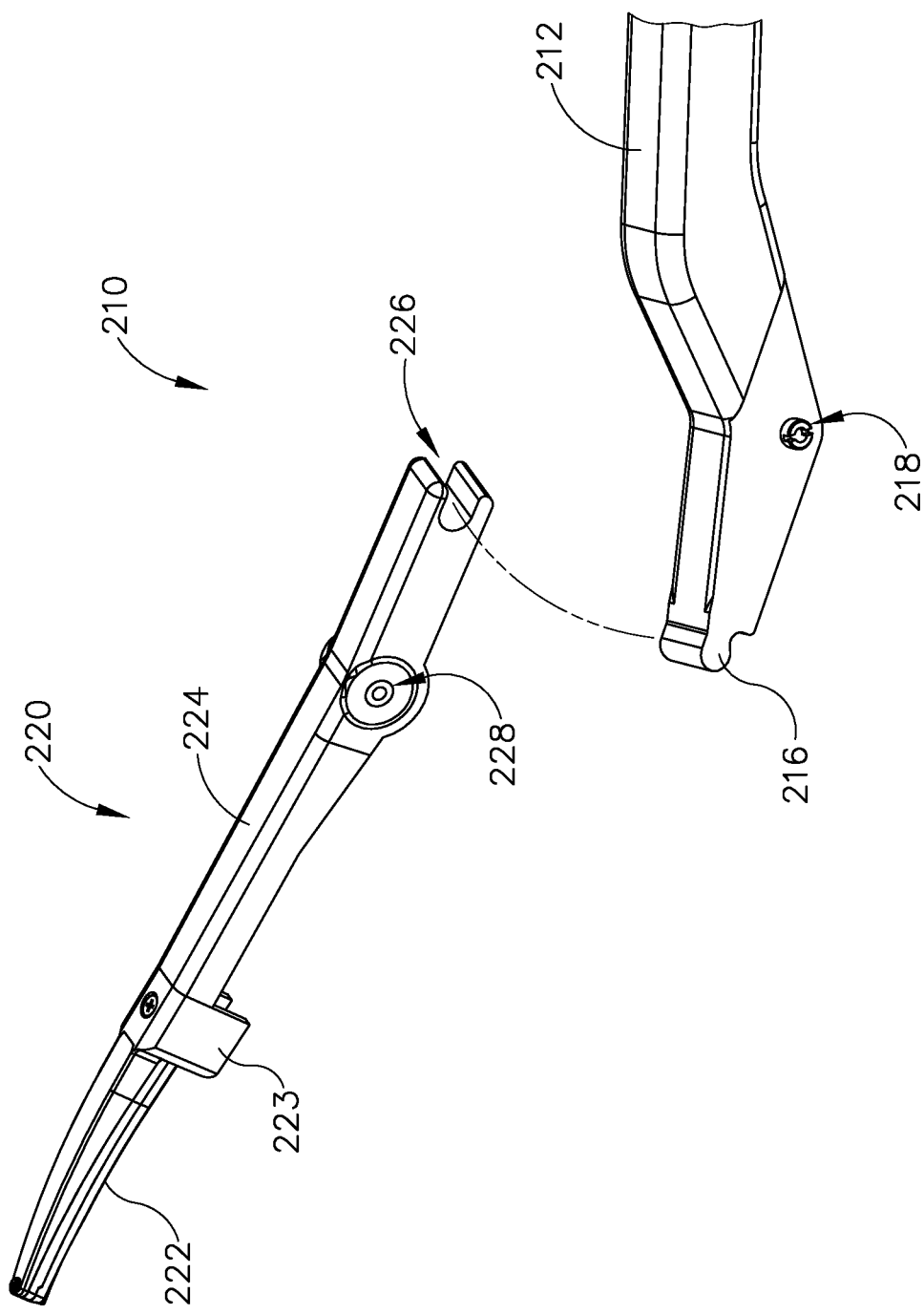
FIG. 10 depicts an exploded perspective view of a clamp arm assembly and a clamp pad assembly of the second modular assembly of FIG. 8.
Figure 11:
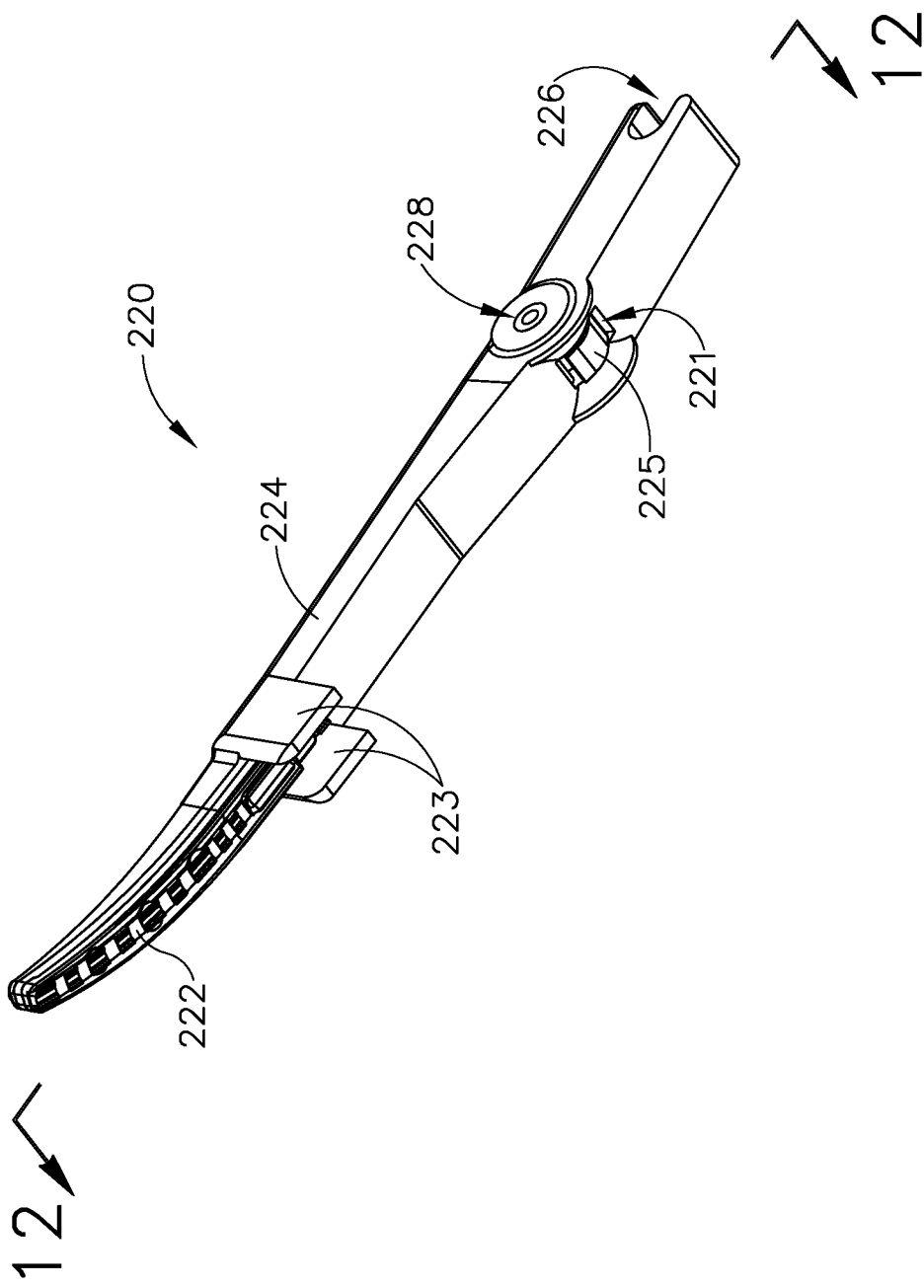
FIG. 11 depicts a perspective view of the clamp arm assembly of FIG. 10.
Figure 12:
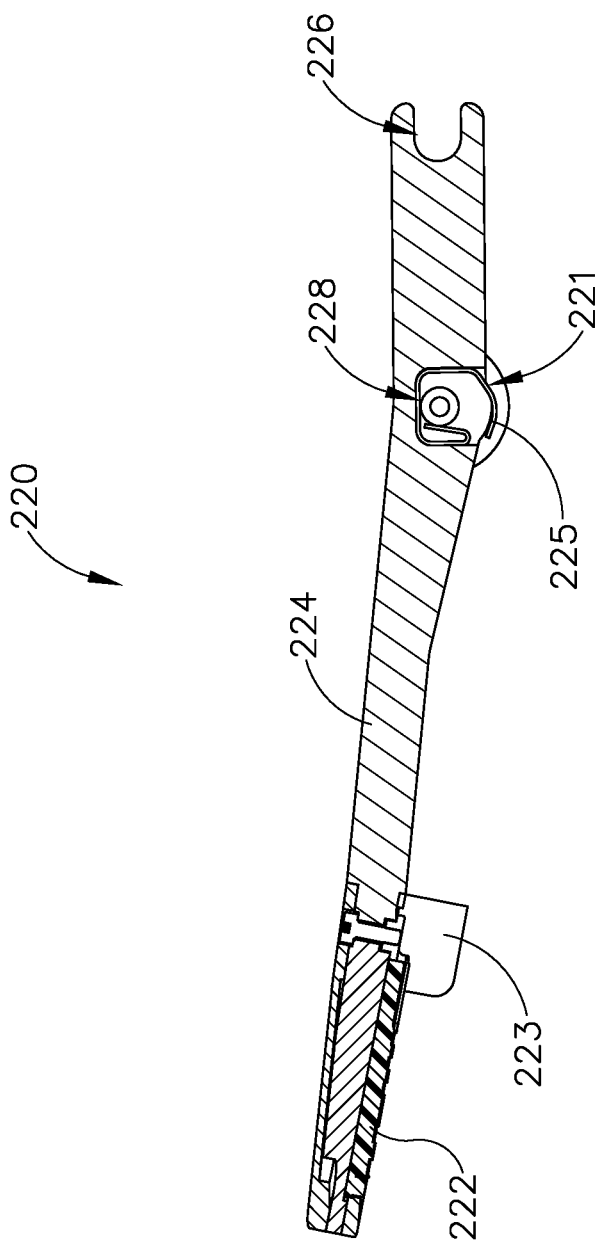
FIG. 12 depicts a cross-sectional side view of the clamp arm assembly of FIG. 10, taken along line 12-12 of FIG. 11.

As mentioned above, and as will be described below, coupling member (300) is configured to selectively couple first modular assembly (100) with second modular assembly (200). As best seen in FIG. 7, coupling member (300) comprises a body (302), a pair of resilient arms (304) extending from body (302), and a pair of grips (305) extending from body (302). Resilient arms (304) each define a respective pivot bore (306) and locking assembly (308). Resilient arms (304) are spaced apart from each other in order to receive proximal outer sheath (132) and to snap-fit pivot bores (306) with respective protrusions (136). Therefore, as shown between FIGS. 13B-13C and 14B-14C, coupling member (300) is configured to pivotally connect with proximal outer sheath (132) via pivot bores (306) and protrusions (136). While in the current example, coupling member (300) and proximal outer sheath (132) are pivotally coupled via snap-fitting, any other type of suitable connection may be used as would be apparent to one having ordinary skill in the art in view of the teachings herein. For example, protrusions (136) may be extendable relative to proximal outer sheath (132) in order to pivotally couple with pivot bore (306) of coupling member (300). Grips (305) may be positioned on body (302) such that an operator may easily rotate coupling member (300) relative to outer sheath (132) via grips (305).

Each locking assembly (308) includes an interior contact wall (310) facing toward each other and a coupling recess (312). As will be described in greater detail below, locking assembly (308) is configured to rotate about pivot bore (306) and protrusions (136) in order to selectively couple with portions of second modular assembly (200).

While coupling member (300) in the current example is used to connect first modular assembly (100) with second modular assembly (200), it should be understood that coupling member (300) may be incorporated into any suitable type of modular assembly that would be apparent to one having ordinary skill in the art in view of the teachings herein. For example, coupling assembly (300) may be modified to couple different modular clamp arm assemblies with first modular assembly (100) where the different modular clamp arm assemblies include clamp arm assemblies such as those taught in U.S. Pub. No. 2017/0105788, entitled "Surgical Instrument with Dual Mode End Effector and Modular Clamp Arm Assembly," published Apr. 20, 2017, issued as U.S. Pat. No. 10,893,914 on Jan. 19, 2021, the disclosure of which is incorporated by reference herein. Thus, one modular clamp arm assembly that may be coupled with first modular assembly (100) may provide pivotal motion of a clamp arm at one side of ultrasonic blade (150) while the other modular clamp arm assembly that may be coupled with first modular assembly (100) may provide pivotal motion of a clamp arm at the other side of ultrasonic blade (150). Other suitable kinds of clamp arm assemblies that may be used to provide different kinds of second modular assemblies (200) will be apparent to those of ordinary skill in the art in view of the teachings herein.

Second modular assembly (200) includes a clamp arm assembly (210), a clamp pad assembly (220), and a distal outer sheath (230). As will be described in greater detail below, distal outer sheath (230) is configured to couple with both coupling member (300) and proximal outer sheath (132) in order to selectively couple first modular assembly (100) with second modular assembly (200). It other words, when properly coupled, proximal outer sheath (132) and distal outer sheath (230) may be fixed relative to one another. As will also be described in greater detail below, clamp arm assembly (210) and clamp pad assembly (220) are both pivotally coupled with distal outer sheath (230). Additionally, clamp arm assembly (210) and clamp pad assembly (220) are dimensioned to mesh with each other such that rotation of one assembly (210, 220) relative to distal outer sheath (230) causes rotation of the other assembly (210, 220) relative to distal outer sheath (230). In other words, clamp arm assembly (210) and clamp pad assembly (220) are capable of rotating each other relative to distal outer sheath (230).

Distal outer sheath (230) includes a U-shaped body (232) extending from a distal face (235) and terminating in a pair of proximally presented projections (234). Proximally presented projections (234) each include a lateral protrusion (238) extending away from U-shaped body (232). U-shaped body (232) defines a longitudinal pathway (236) and a plurality of bores (240). U-shaped body (232) and longitudinal pathway (236) are dimensioned to receive tube (138) and to rotationally house a portion of clamp arm assembly (210) and clamp pad assembly (220). In particular, as best shown between FIGS. 13A-13B, U-shaped body (232) may be inserted over ultrasonic blade (150) and tube (138) such that tube (138) will rest under clamp arm assembly (210) and clamp pad assembly (220). Tube (138) may protect waveguide (140) such that clamp arm assembly (210) and clamp pad assembly (220) do not contact adjacent portions of waveguide (140).

Figure 13A:
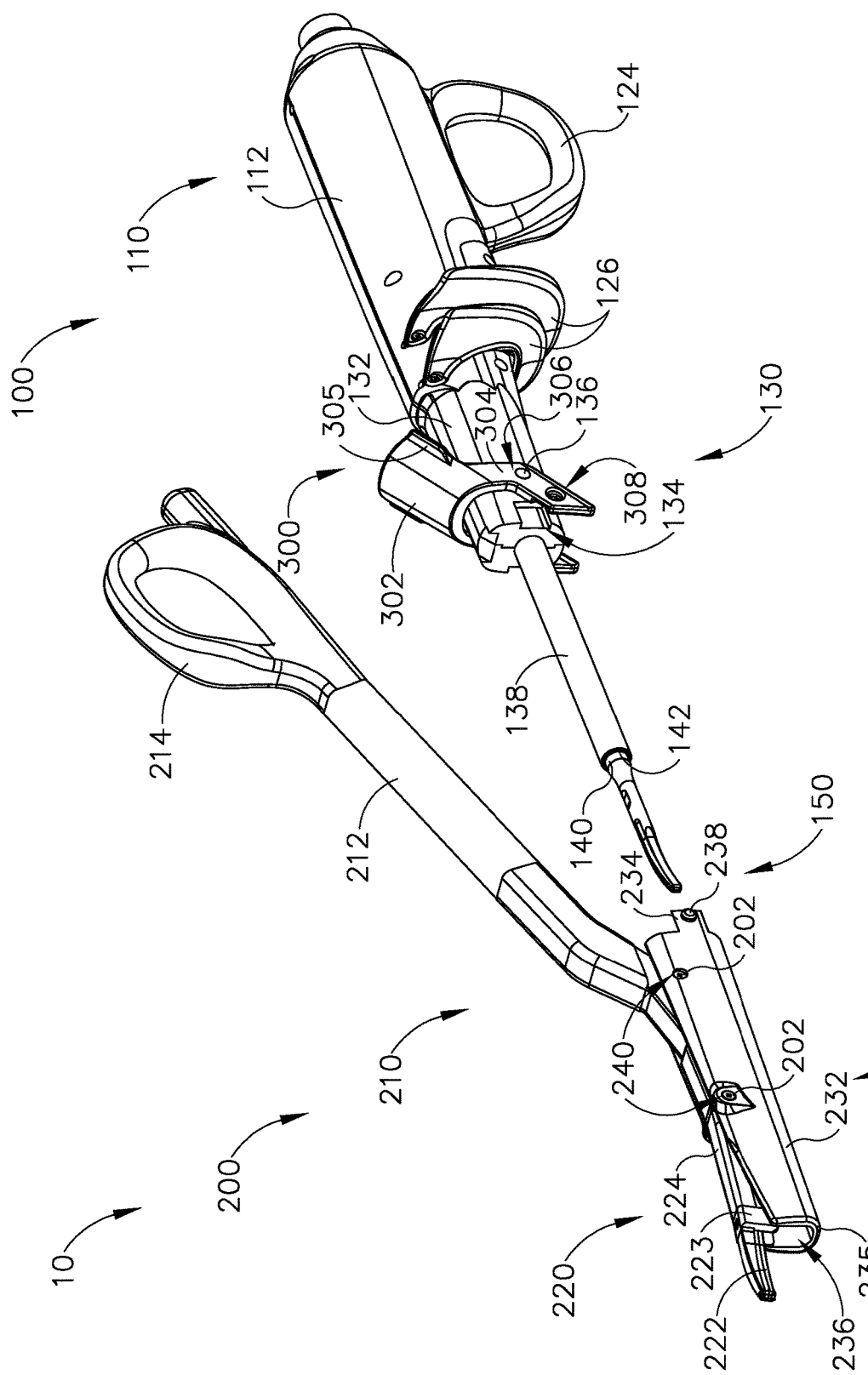
FIG. 13A depicts a perspective view of the second modular assembly of FIG. 8 aligned with the shaft assembly of FIG. 5 in order to couple the modular assemblies together.
Figure 13B:
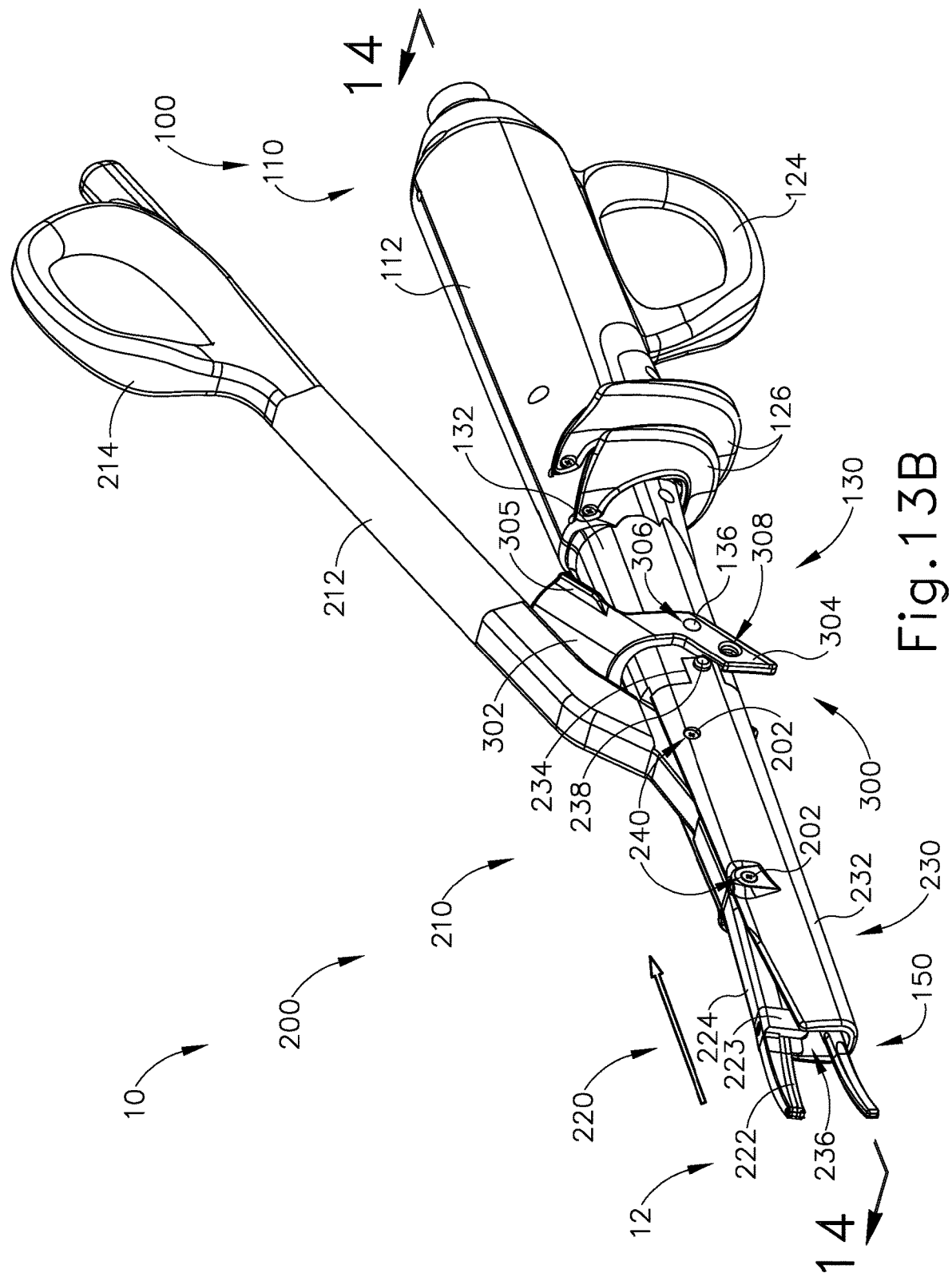
FIG. 13B depicts a perspective view of the second modular assembly of FIG. 8 inserted over the shaft assembly of FIG. 5.
Figure 14A:
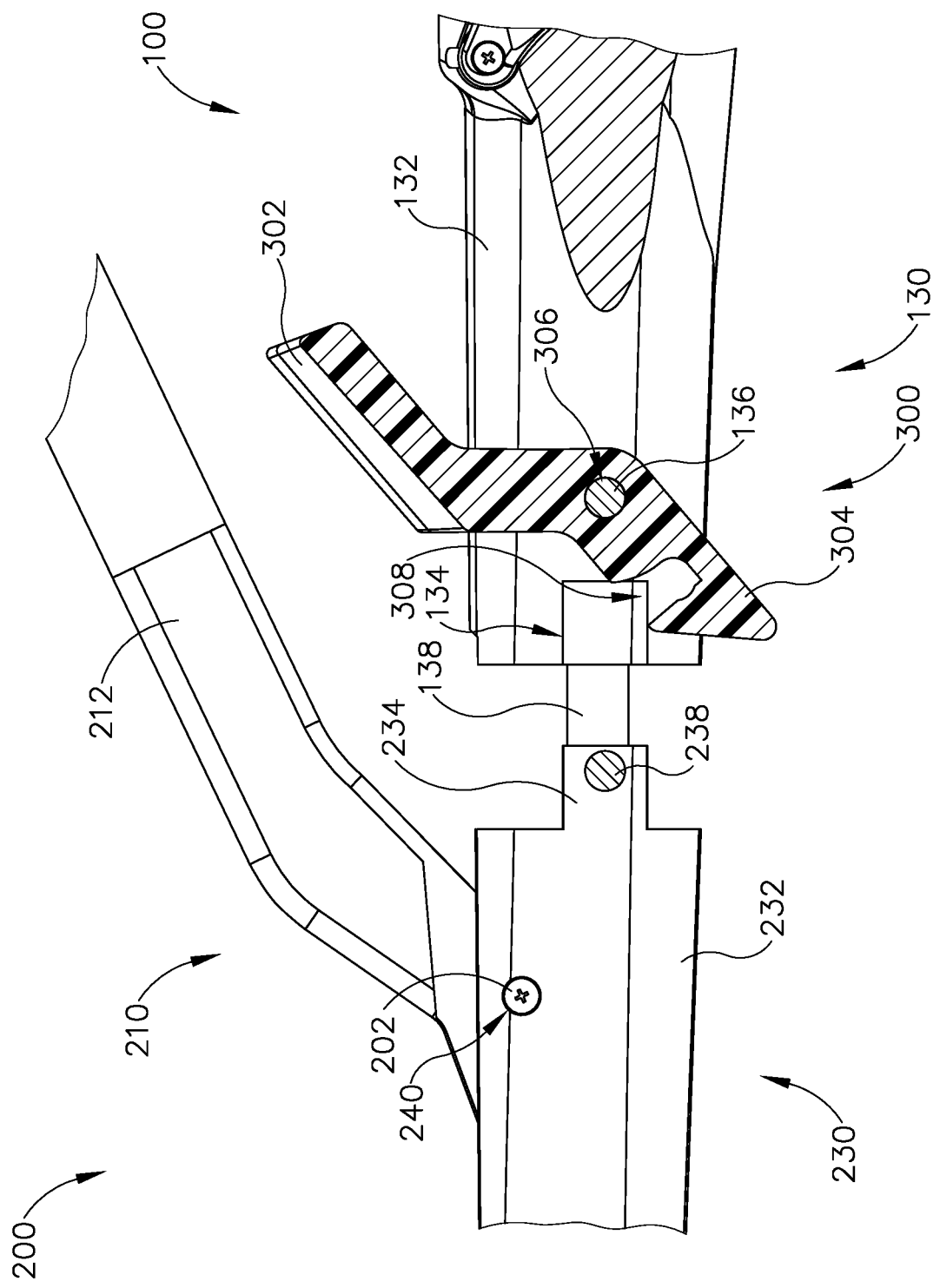
FIG. 14A depicts a cross-sectional side view of the second modular assembly of FIG. 8 partially inserted over the shaft assembly of FIG. 5, taken along line 14-14 of FIG. 13B.
Figure 14B:
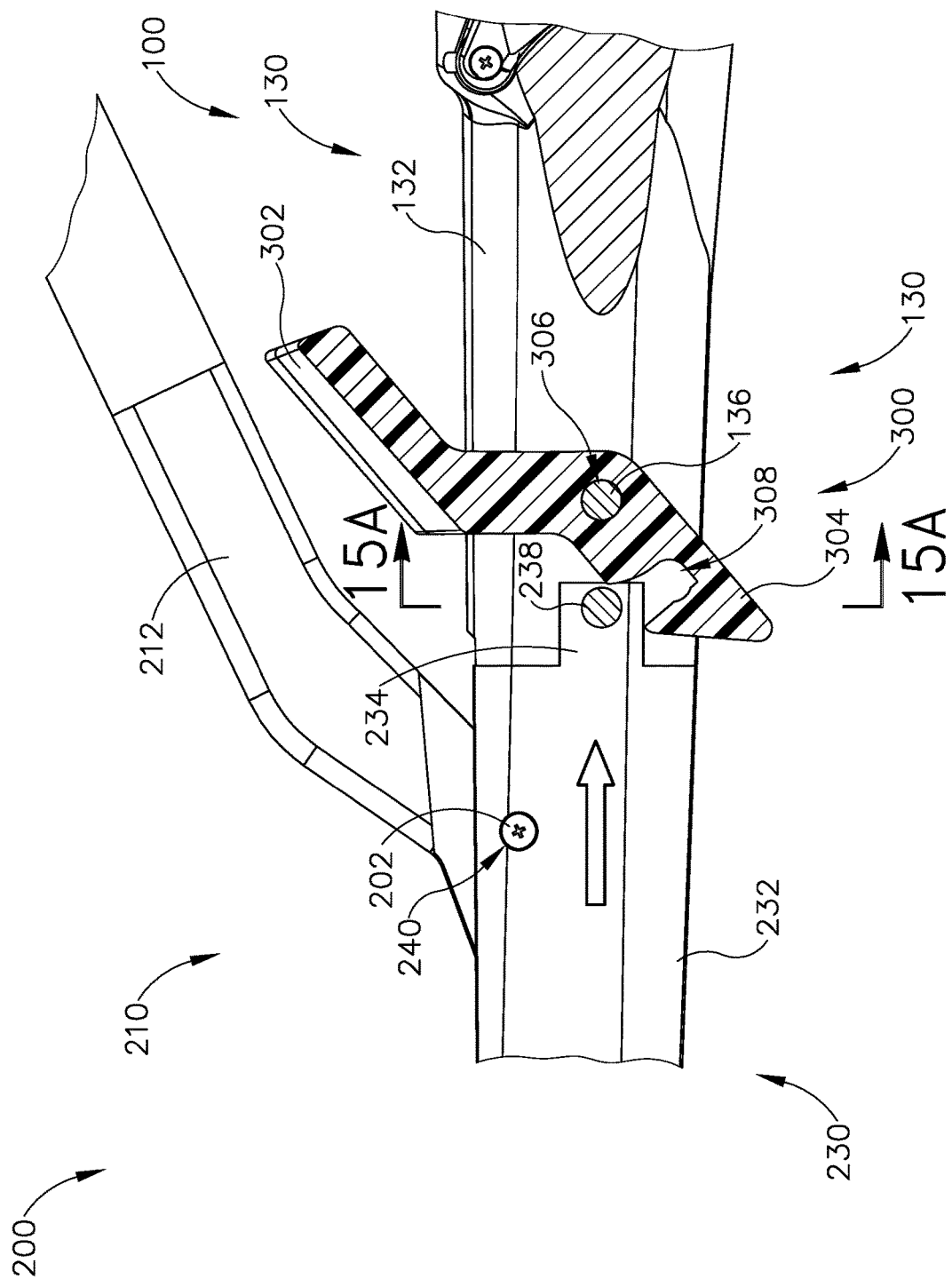
FIG. 14B depicts a cross-sectional side view of the second modular assembly of FIG. 8 further inserted over the shaft assembly of FIG. 5, taken along line 14-14 of FIG. 13B.

As shown between FIGS. 13A-13B and between FIGS. 14A-14B, proximally presented projections (234) are configured to be inserted into recesses (134) defined by proximal outer sheath (132). When proximally presented projections (234) are inserted into recesses (134), distal outer sheath (230) may not rotate relative to proximal outer sheath (132) about a longitudinal axis defined by tube (138). Therefore, proximally presented projections (234) may mate with recesses (134) in order to rotationally fix distal outer sheath (230) relative to proximal outer sheath (132).

Figure 13C:
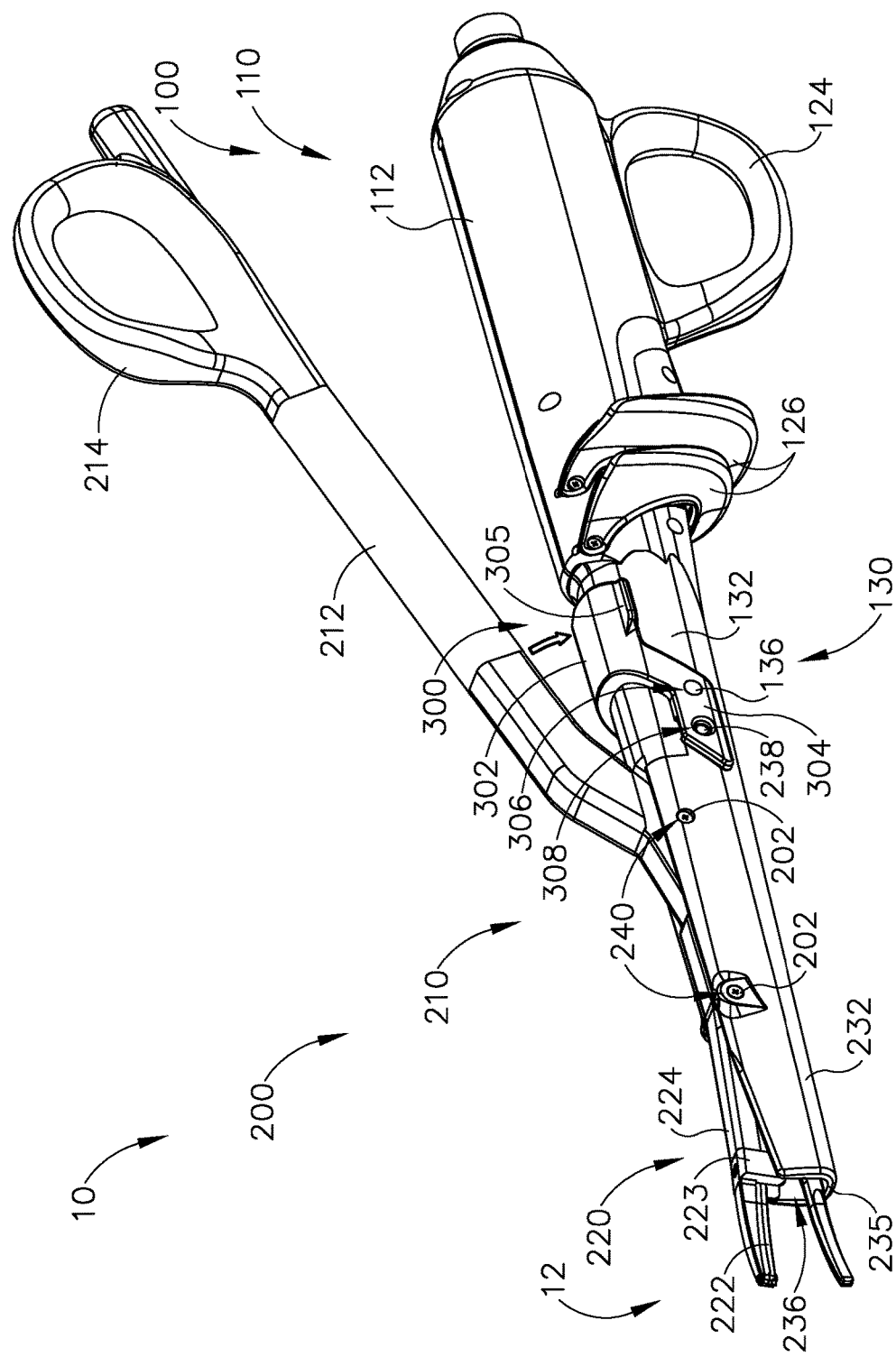
FIG. 13C depicts a perspective view of the second modular assembly of FIG. 8 coupled with the shaft assembly of FIG. 5 via the coupling member of FIG. 7.
Figure 14C:
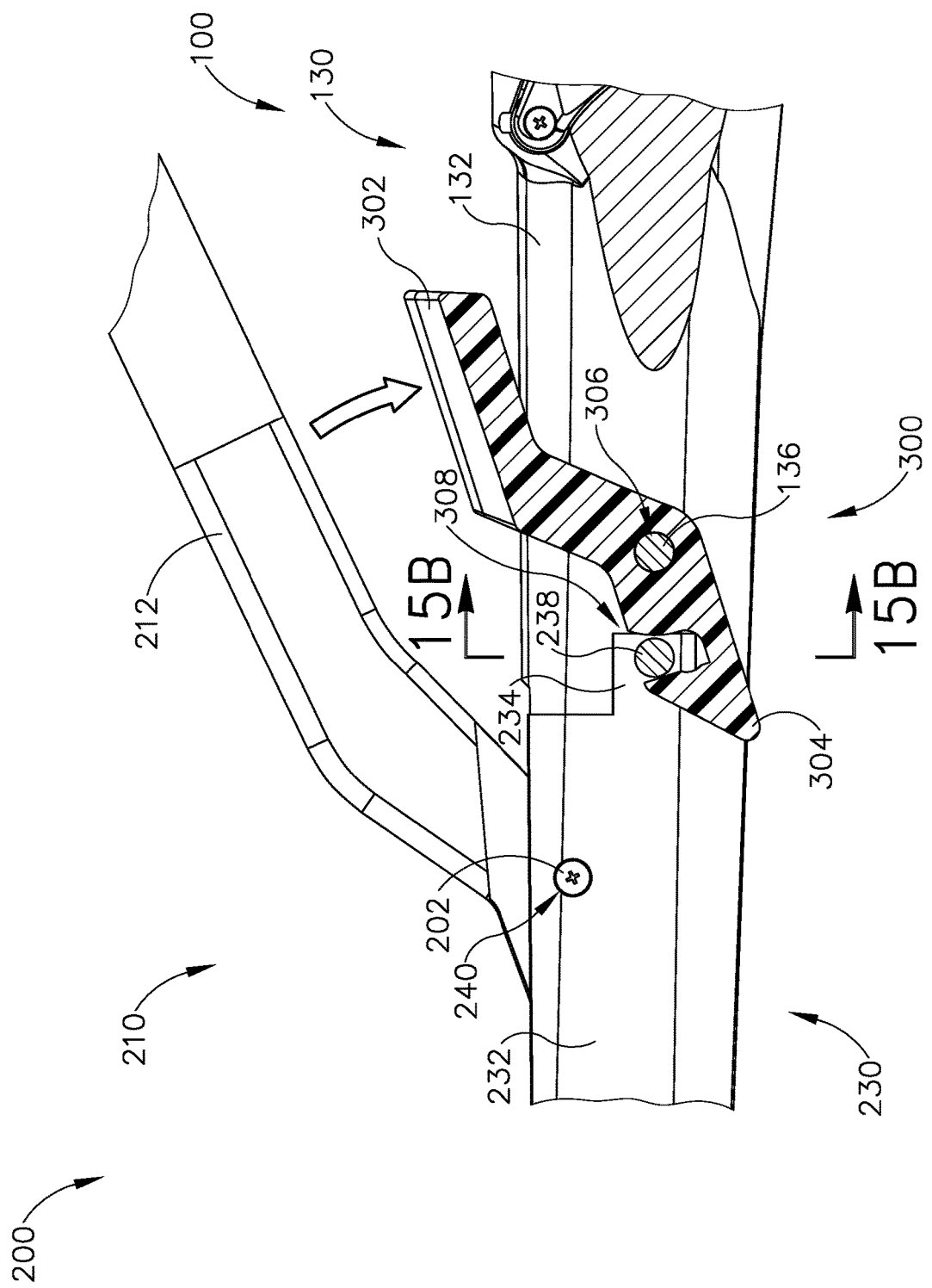
FIG. 14C depicts a cross-sectional side view of the second modular assembly of FIG. 8 inserted over the shaft assembly of FIG. 5 while the coupling member of FIG. 7 is rotated toward a configuration to couple the shaft assembly with the second modular assembly, taken along line 14-14 of FIG. 13B.
Figure 14D:
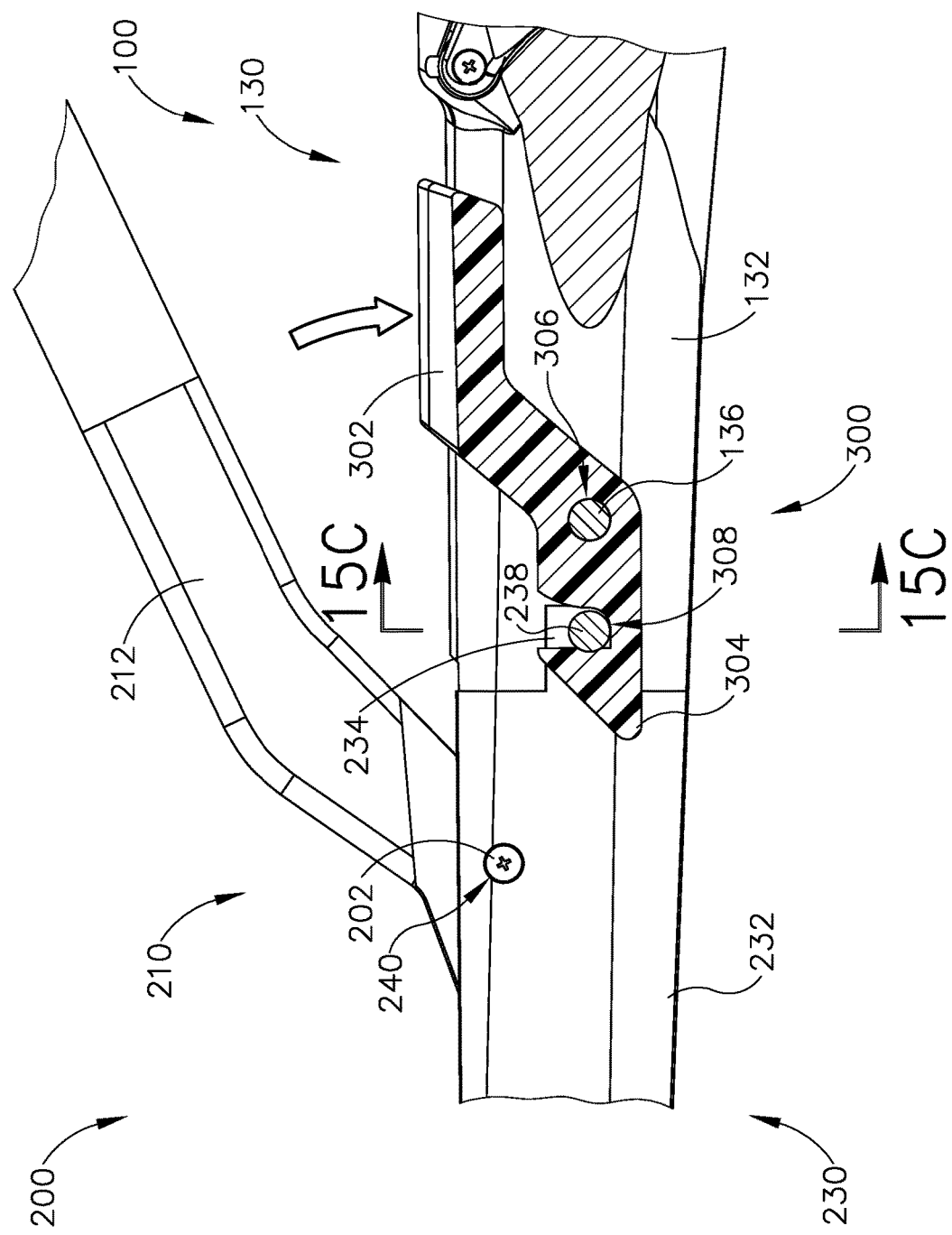
FIG. 14D depicts a cross-sectional side view of the coupling member of FIG. 7 connecting the second modular assembly of FIG. 8 and the shaft assembly of FIG. 5, taken along line 14-14 of FIG. 13B.
Figure 15B:
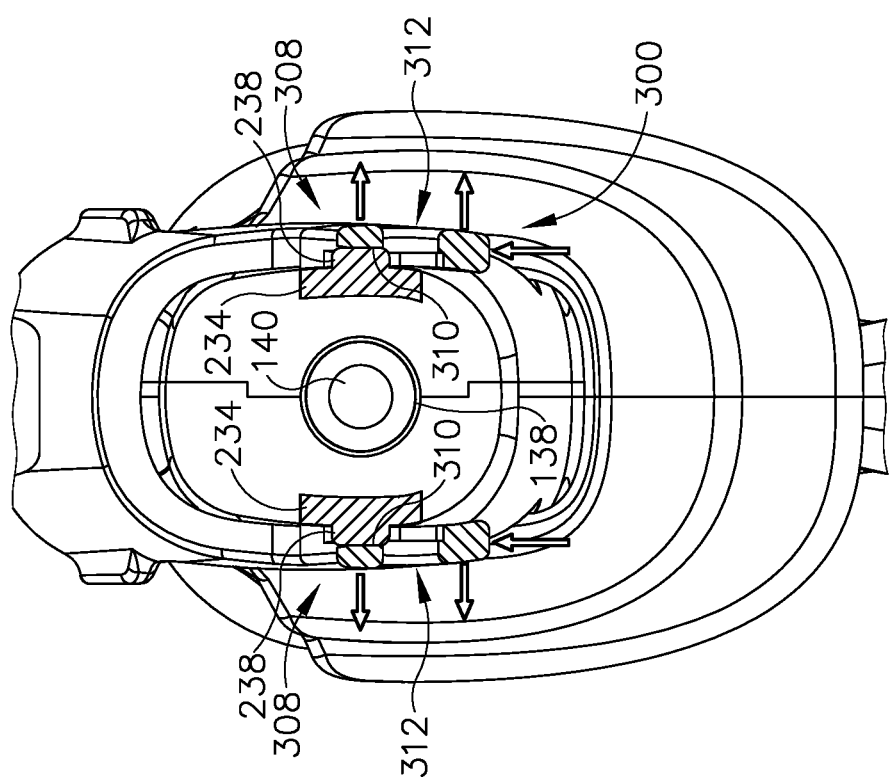
FIG. 15B depicts of cross-sectional front view of the second modular assembly of FIG. 8 inserted over the shaft assembly of FIG. 5 while the coupling member of FIG. 7 is rotated toward a configuration to couple the shaft assembly with the second modular assembly, taken along line 15B-15B of FIG. 14C.
Figure 15C:
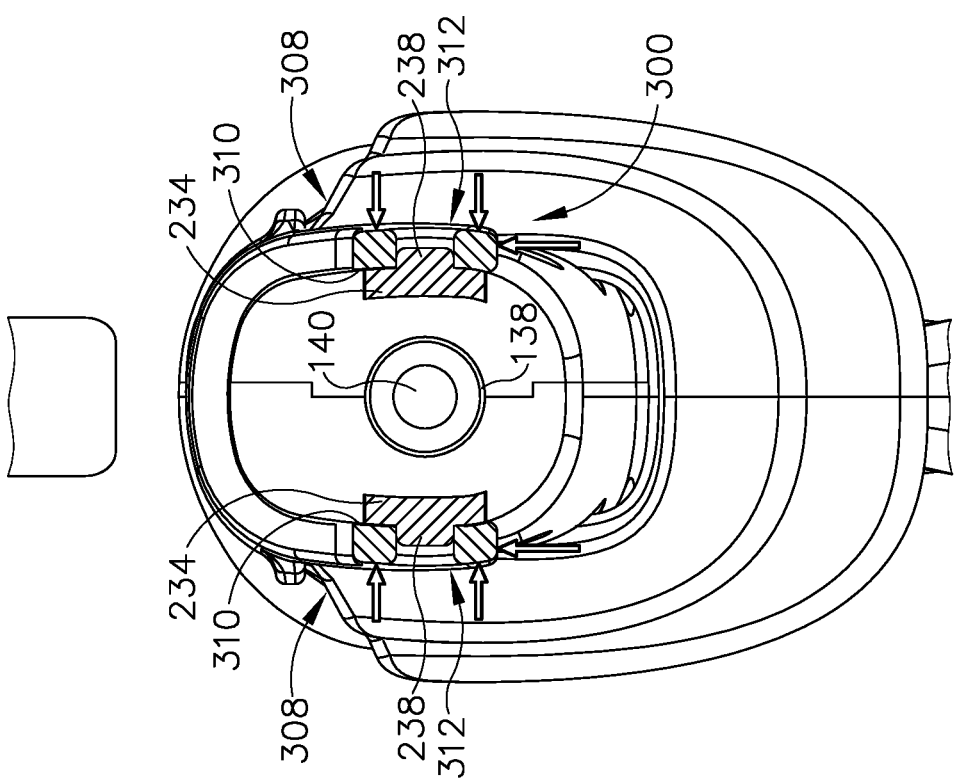
FIG. 15C depicts a cross-sectional front view of the coupling member of FIG. 7 connecting the second modular assembly of FIG. 8 and the shaft assembly of FIG. 5, taken along line 15C-15C of FIG. 14D.

As shown between FIGS. 13B-13C, between FIGS. 14B-14D, and between FIGS. 15A-15C, once distal outer sheath (230) is rotationally fixed relative to proximal outer sheath (132), an operator may rotate coupling member (300) such that locking assembly (308) snap-fits with lateral protrusions (238). In particular, an operator may rotate coupling member (300) about protrusion (136) such that lateral protrusions (238) cam against contact walls (310) of resilient arms (304). As a result, as best seen in FIG. 15B, contact between contact walls (310) and lateral protrusions (238) flex resilient arms (304) outwardly away from proximally presented projections (234). An operator may further rotate coupling member (300) about protrusions (136) such that lateral protrusions (238) no longer abut against contact wall (310), as shown in FIGS. 13C, 14C, and 15C. The resilient nature of resilient arms (304) allows resilient arms (304) to return to a relaxed position such that lateral protrusions (238) rest within coupling recess (312) of locking assembly (308). With locking assembly (308) of coupling member (300) fully attached, and shown in FIGS. 13C, 14D, and 15C, distal outer sheath (230) is longitudinally fixed relative to proximal outer sheath (132), thereby coupling first modular assembly (100) with second modular assembly (200).

If an operator wishes to decouple first modular assembly (100) with second modular assembly (200), an operator may grasp grips (305) to rotate coupling member (300) in the opposite direction about protrusions (136) in order to flex resilient arms (304) to pop out lateral protrusions (238) from coupling recess (312).

As mentioned above, clamp arm assembly (210) and clamp pad assembly (220) are both pivotally coupled with distal outer sheath (230) such that rotation of one assembly (210, 220) relative to distal outer sheath (230) causes rotation of the other assembly (210, 220) relative to distal outer sheath (230).

Clamp arm assembly (210) includes an elongated arm (212), a thumb grip ring (214), a camming protrusion (216), and a pivot coupling (218). Thumb grip ring (214) and elongated arm (212) together provide a scissor grip type configuration in combination with body (112) and finger grip ring (124). Pivot coupling (218) pivotally couples clamp arm assembly (210) with distal outer sheath (230) via pins (202). As will be described in greater detail below, camming protrusion (216) interacts with clamp pad assembly (220) in order to rotate clamp pad assembly (220) in response to rotation of clamp arm assembly (210).

Clamp pad assembly (220) includes a clamp pad (222) facing ultrasonic blade (150), a pair of tissue stops (223) located adjacent to ultrasonic blade (150) and proximal to clamp pad (222), an arm (224) defining both a camming recess (226) and a spring recess (221), a pivot coupling (228), and a leaf spring (225) housed within spring recess (221). In some versions, clamp pad assembly (220) further includes one or more electrodes that is/are operable to apply RF electrosurgical energy to tissue. Various references herein provide examples of how a clamp pad assembly may incorporate one or more electrodes that is/are operable to apply RF electrosurgical energy to tissue, while other examples of how clamp pad assembly (220) may incorporate one or more electrodes that is/are operable to apply RF electrosurgical energy to tissue will be apparent to those of ordinary skill in the art in view of the teachings herein.

In the current example, tissue stops (223) longitudinally align with distal face (235) when end effector (12) is in the closed position. Tissue stops (223) and distal face (235) may cooperate to consistently and simply prevent tissue from inadvertently reaching a proximal position within end effector (12) where ultrasonic energy from blade (150) may not adequately sever or seal the tissue. In providing such prevention, tissue stop (223) may eliminate the need for an operator to visualize proximal region of end effector (12) in order to determine whether the tissue has reached an undesirably proximal position within end effector (12).

Camming protrusion (216) is dimensioned to rotate within camming recess (226) while also contacting camming recess (226). Camming protrusion (216) and camming recess (226) are positioned within distal outer sheath (230) such that both are located between pivot couplings (218, 228) while clamp arm assembly (210) and clamp pad assembly (220) are pivotally coupled to distal outer sheath (230). Therefore, as shown between FIGS. 1A-1B and 16A-16B, when an operator rotates elongated arm (212) about pivot coupling (218) toward distal outer sheath (230), camming protrusion (216) rotates away from distal outer sheath (230) about pivot coupling (218). Because camming protrusion (216) is housed within camming recess (226), upward movement of camming protrusion (216) about pivot coupling (218) causes upward movement of camming recess (226) about pivot coupling (228). Upward movement of camming recess (226) about pivot coupling (228) rotates arm (224) such that clamp pad (222) rotates toward ultrasonic blade (150). Therefore, closure of elongated arm (212) of clamp arm assembly (210) toward handle assembly (110)

leads to closure of clamp pad (222) toward ultrasonic blade (150). It should therefore be understood that when first modular assembly (100) and second modular assembly (200) are connected, an operator may squeeze thumb grip ring (214) toward body (112) to thereby clamp tissue between clamp pad assembly (220) and ultrasonic blade (150) to compress tissue against ultrasonic blade (150). When ultrasonic blade (150) is activated during such compression, clamp pad assembly (220) and ultrasonic blade (150) cooperate to transect and/or seal the compressed tissue.

As mentioned above, leaf spring (225) is housed within spring recess (221). As best seen in FIGS. 16A-16B, leaf spring (225) is dimensioned such that a portion of leaf spring (225) extends out of spring recess (221) to make contact against tube (138) in order to provide electrical continuity between the one or more RF electrodes of end effector (12) and the source of electrical power. It should be understood that leaf spring (225) maintains this electrical continuity throughout the range of motion of clamp pad assembly (220). It should also be understood that any other suitable kinds of features may be used to provide electrical continuity between the one or more RF electrodes of end effector (12) and the source of electrical power.

In some versions, one or more resilient members are used to bias clamp pad assembly (220) toward the open position shown in FIGS. 1A and 16A. Of course, any other suitable kind of resilient member may be used as would be apparent to one having ordinary skill in the art in view of the teachings herein, such as a torsion spring. Alternatively, clamp pad assembly (220) need not necessarily be biased toward the open position.

Pivot couplings (218, 228) of clamp arm assembly (210) and clamp pad assembly (220) being located within longitudinal pathway (236) of distal outer sheath (230) may provide certain desirable advantages as compared to clamp arm assembly (210) and clamp pad assembly (220) pivotally coupling with an exterior of distal outer sheath (230). For instance, there may be a reduced chance of inadvertently pinching tissue due to rotation of clamp arm assembly (210) and clamp pad assembly (220) with pivot couplings (218, 228) being housed within U-shaped body (232). In other words, U-shaped body (232) may protect tissue from being inadvertently pinched by rotation of clamp arm assembly (210) and clamp pad assembly (220) relative to distal outer sheath (230). Additionally, the width of second modular assembly (200) may be reduced due to pivot couplings (218, 228) being housed within longitudinal pathway (236) of distal outer sheath (230). It may also be easier to fabricate desired components due to the simplified shapes of clamp arm assembly (210) and clamp pad assembly (220). A reduction of tolerance stack may also be an advantage to storing pivot couplings (218, 228) within the interior of distal outer sheath (230).

The foregoing components and operabilities of instrument (10) are merely illustrative. Instrument (10) may be configured in numerous other ways as will be apparent to those of ordinary skill in the art in view of the teachings herein. By way of example only, at least part of instrument (10) may be constructed and/or operable in accordance with at least some of the teachings of any of the following, the disclosures of which are all incorporated by reference herein: U.S. Pat. Nos. 5,322,055; 5,873,873; 5,980,510; 6,325,811; 6,783,524; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pat. Nos. 9,023,071; 8,461, 744; 9,381,058; U.S. Pub. No. 2012/0116265, now abandoned; U.S. Pat. Nos. 9,393,037; 9,095,367; and/or U.S. Pub. No. 2015/0080925, entitled "Alignment Features for Ultrasonic Surgical Instrument," published Mar. 19, 2015, now abandoned, the disclosure of which is incorporated by reference herein.

Figure 17:
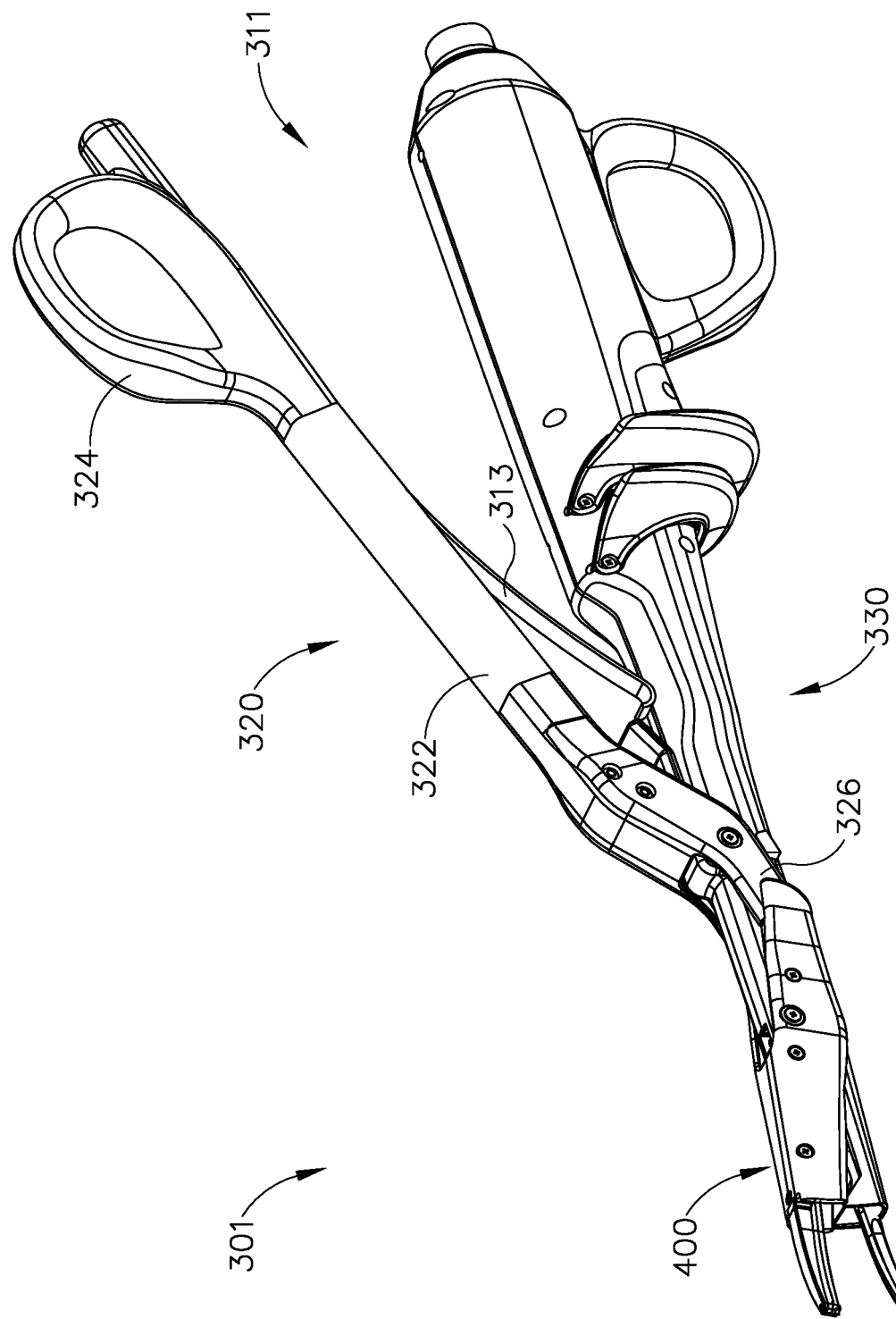
FIG. 17 depicts a perspective view of a second exemplary surgical instrument, with an end effector of the instrument in an open configuration.
Figure 18:
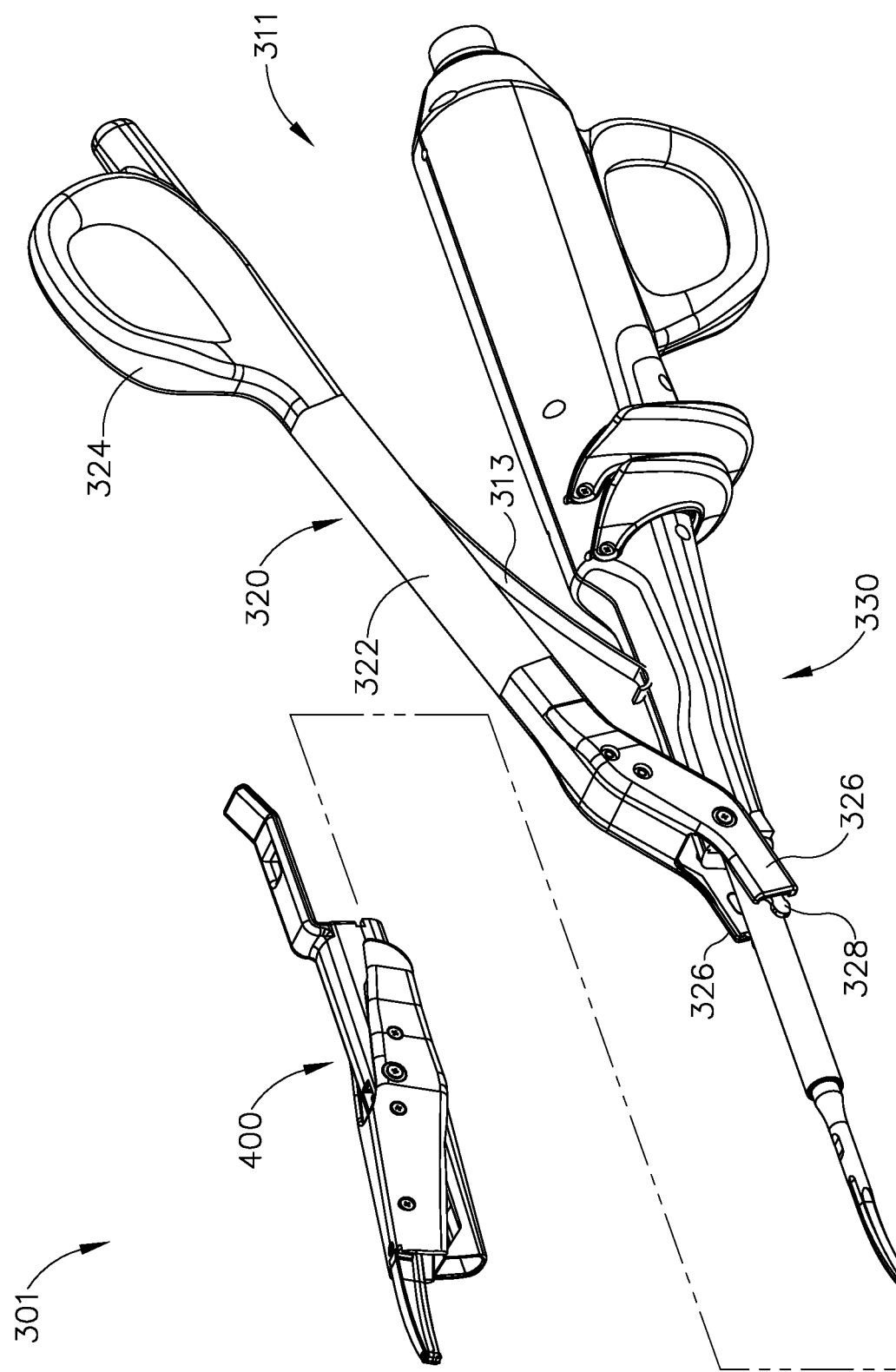
FIG. 18 depicts a partially exploded perspective view of the instrument of FIG. 17.

II. Second Exemplary Ultrasonic Surgical Instrument for Open Surgical Procedures FIGS. 17-18 show a second exemplary ultrasonic surgical instrument (301). Except as otherwise described below, instrument (301) of this example may be constructed and operable just like instrument (10) described above. Certain details of instrument (301) will therefore be omitted from the following description, it being understood that such details are already provided above in the description of instrument (10).

Instrument (301) of the present example comprises a handle assembly (311), a clamp arm actuator (320), a shaft assembly (330), and a clamp arm assembly (400). Handle assembly (311) of this example is configured and operable just like handle assembly (110) described above, such that details of handle assembly (311) will not be reiterated here.

Figure 19:
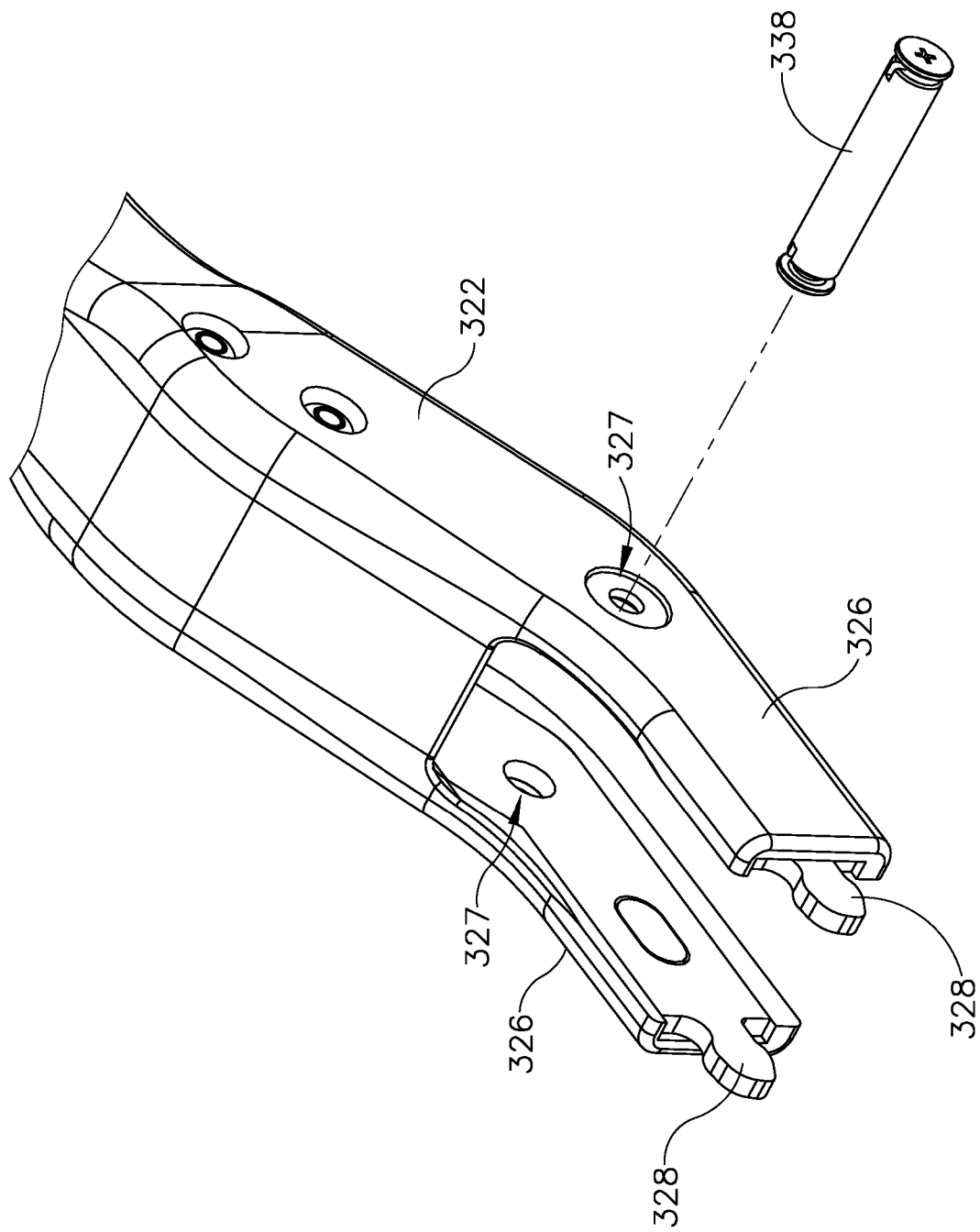
FIG. 19 depicts a partial perspective view of the distal end of a clamp arm actuator of the instrument of FIG. 17.

Clamp arm actuator (320) is pivotably coupled with shaft assembly (330). In the present example, clamp arm actuator (320) is not removable from shaft assembly (330). Clamp arm actuator (320) of the present example comprises a shaft (322). A thumb ring (324) is positioned at the proximal end of shaft (322). As best seen in FIGS. 18-19, pair of projections (326) extend distally from shaft (322). Projections (326) are laterally spaced apart from each other and extend parallel to each other. As best seen in FIG. 19, the distal end of each projection (326) includes a camming protrusion (328). Camming protrusions (328) are configured to cooperate with clamp arm assembly (400), in a manner similar to camming protrusions (216), as will be described below. As also best seen in FIG. 19, projections (326) also define a pair of pin openings (327), which are configured to receive pin (338). Pin (338) provides a pivotable coupling between clamp arm actuator (320) and shaft assembly (330).

Figure 20:
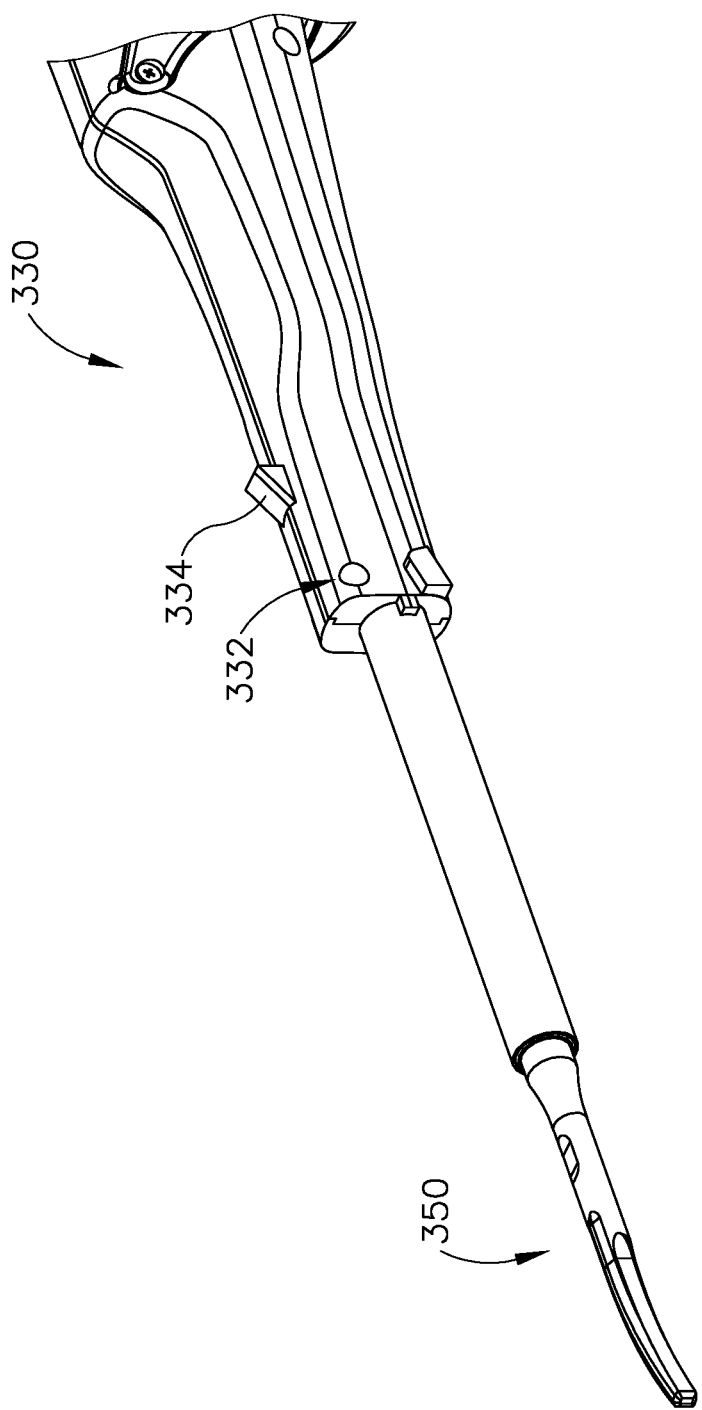
FIG. 20 depicts a perspective view of a shaft assembly and ultrasonic blade of the instrument of FIG. 17.

Shaft assembly (330) extends distally from handle assembly (311) and is substantially identical to shaft assembly (130) described above except for the differences described below. An ultrasonic blade (350), which is identical to ultrasonic blade (150) described above, is positioned at the distal end of shaft assembly (330). As best seen in FIG. 20, shaft assembly (330) defines an opening (332) that is configured to receive pin (338) to thereby provide a pivotable coupling between clamp arm actuator (320) and shaft assembly (330). As also shown in FIG. 20, shaft assembly (330) includes a ramped latch protrusion (334), which is configured to engage clamp arm assembly (400) as will be described in greater detail below.

Figure 21:
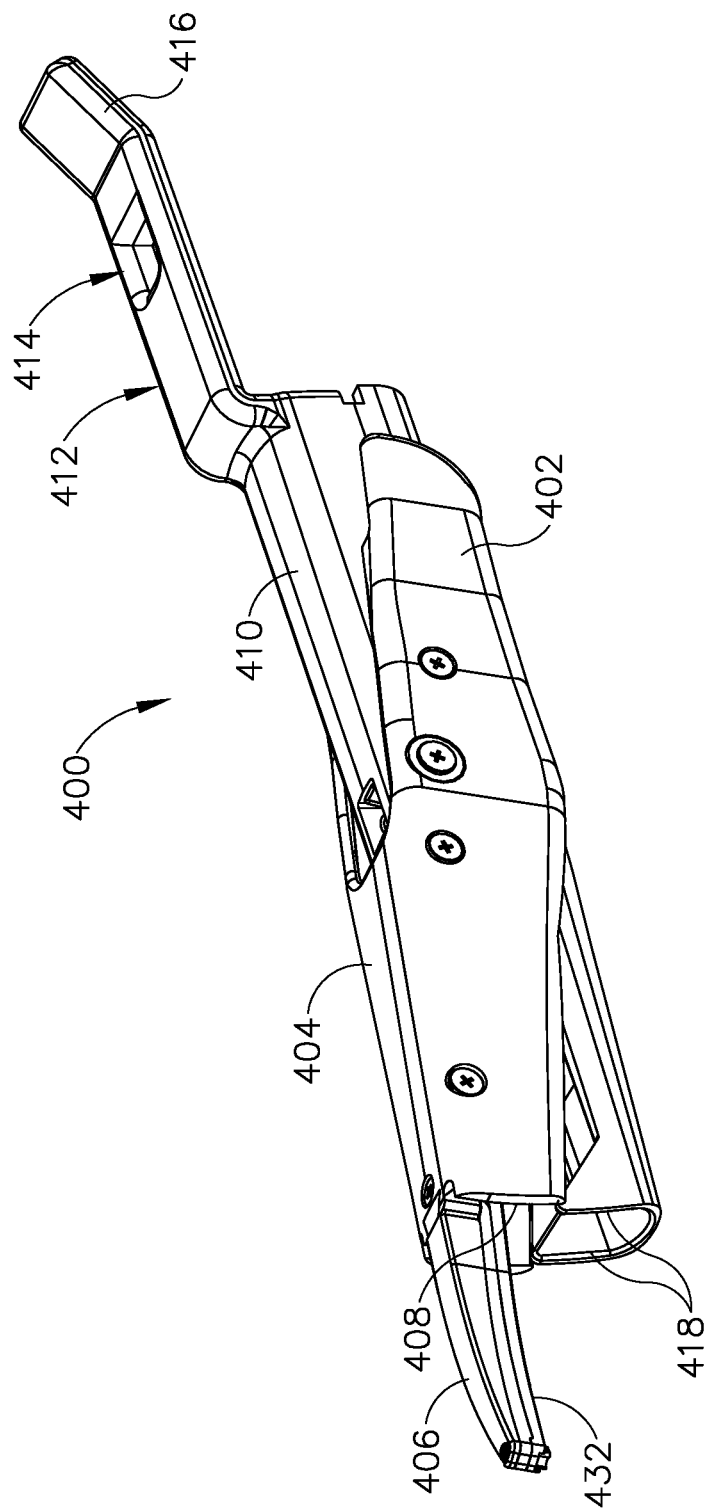
FIG. 21 depicts a perspective view of a removable clamp arm assembly of the instrument of FIG. 17.
Figure 22:
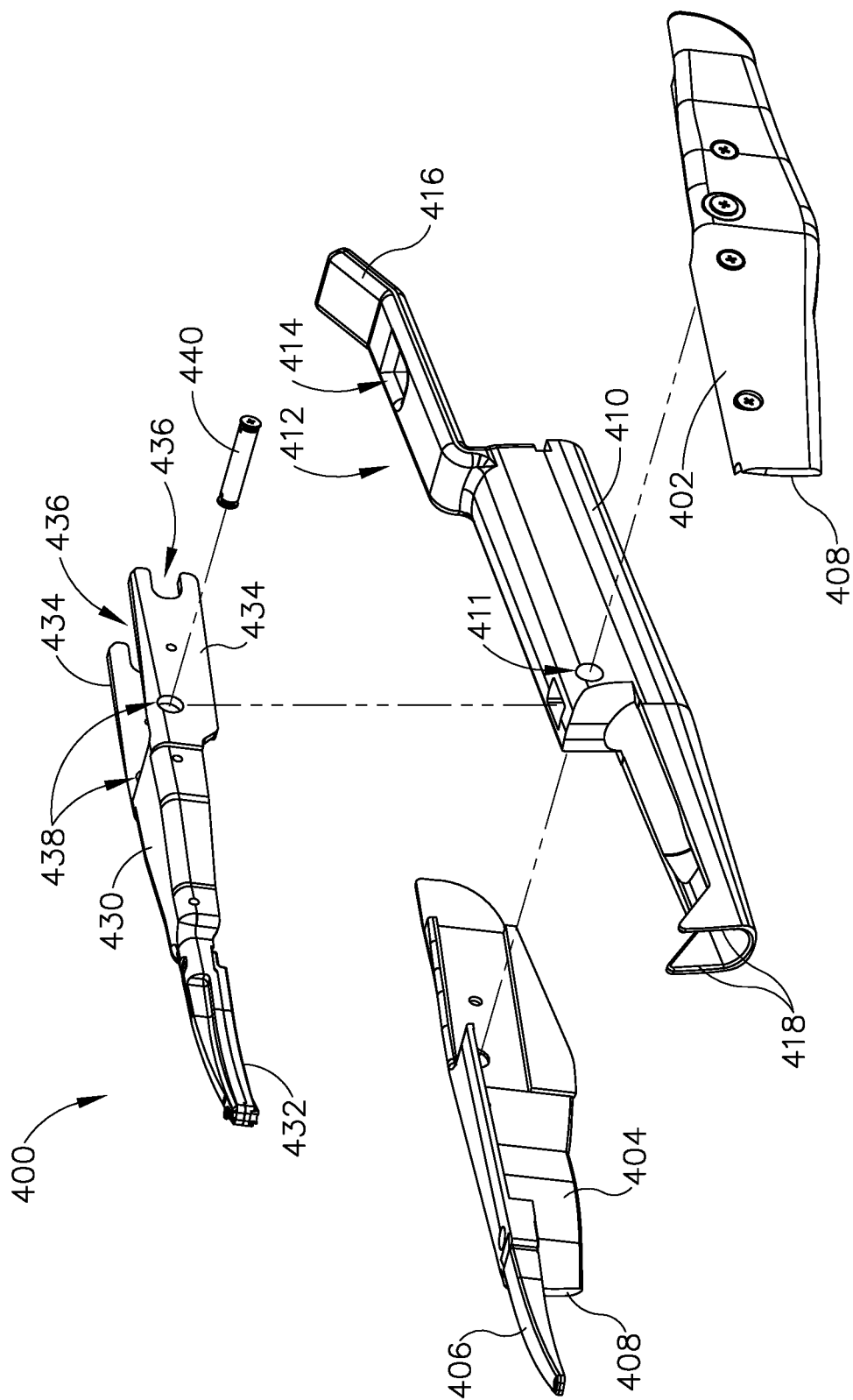
FIG. 22 depicts an exploded perspective view of the clamp arm assembly of FIG. 21.

As shown in FIGS. 21-22, clamp arm assembly (400) of the present example comprises a pair of shrouds (402, 404) partially encompassing a clamp arm body (430), which is pivotally coupled with a stationary body (410). Each shroud includes a distally presented tissue stop edge (408). Stationary body (410) also includes a pair of distally presented tissue stop edges (418). Edges (408, 418) are configured to cooperate to consistently and restrict proximal positioning of tissue like tissue stops (223) and distal face (235) described above. Shroud (404) of the present example also includes a distally projecting shield member (406).

Stationary body (410) of the present example further includes a pin opening (411) and a proximally projecting latch member (412). Latch member (412) defines a latch opening (414) and a ramp (416). Latch member (412) is configured to cooperate with latch protrusion (334) of shaft assembly (330) to selectively secure clamp arm assembly (400) to shaft assembly (330). In particular, when clamp arm assembly (400) is initially provided separately from shaft assembly (330), an operator may align clamp arm assembly (400) with shaft assembly (330) along a common axis, and then insert blade (350) and the remaining distal portion of shaft assembly (330) into clamp arm assembly (400). Ramp (416) will eventually engage latch protrusion (334), which will provide a camming action that causes latch member (412) to deflect away from the longitudinal axis. As the operator continues to insert shaft assembly (330) through clamp arm assembly (400), latch protrusion (334) eventually reaches latch opening (414), at which point latch member (412) resiliently returns to a straight, non-deflected state. At this stage, latch protrusion (334) is disposed in latch opening (414) and thereby secures clamp arm assembly (400) to shaft assembly (330). When the operator wishes to remove clamp arm assembly (400) from shaft assembly (330), the operator may simply engage ramp (416) and thereby urge latch member (412) to a deflected state where latch member (412) can clear latch protrusion (334); then pull clamp arm assembly (400) away from shaft assembly (330). Other suitable structures and techniques that may be used to secure clamp arm assembly (400) to shaft assembly (330), and to remove clamp arm assembly (400) from shaft assembly (330), will be apparent to those of ordinary skill in the art in view of the teachings herein.

Clamp arm body (430) of the present example comprises a clamp pad (432) and a pair of proximal projections (434). Clamp pad (432) is positioned and configured to compress tissue against ultrasonic blade (350) when clamp arm assembly (400) is secured to shaft assembly (330). Shield member (406) of shroud (404) is configured to extend over the exterior of the distal end of clamp arm body (430), without covering clamp pad (432). Shield member (406) thus enables clamp pad (432) to contact tissue directly. Projections (438) each comprise a respective proximally presented recess (436) and a pair of pin openings (438). A pin (440) is positioned in pin openings (411, 438) to thereby pivotally couple clamp arm body (430) with stationary body (410). Shrouds (402, 404) are fixedly secured to clamp arm body (430) such that shrouds (402, 404) pivot with clamp arm body (430) relative to stationary body (410).

Figure 23:
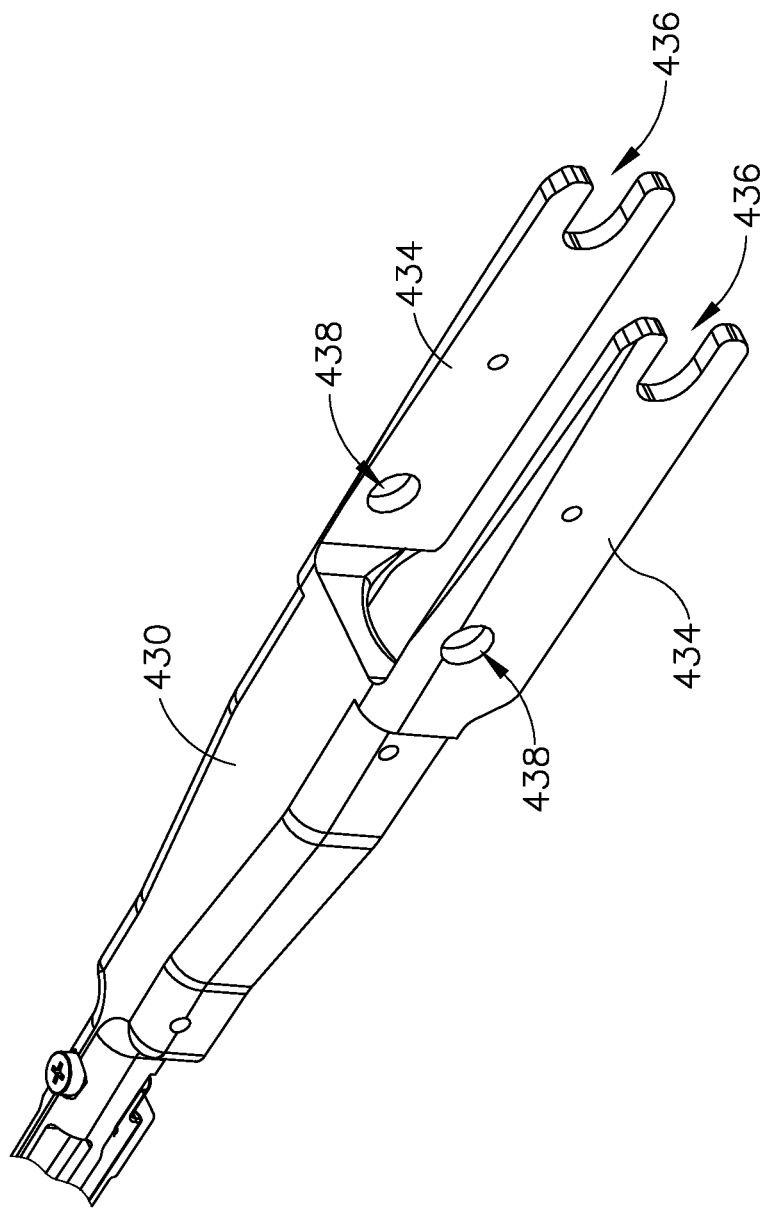
FIG. 23 depicts a partial perspective view of a proximal end of a clamp arm body of the clamp arm assembly of FIG. 22.
Figure 24:
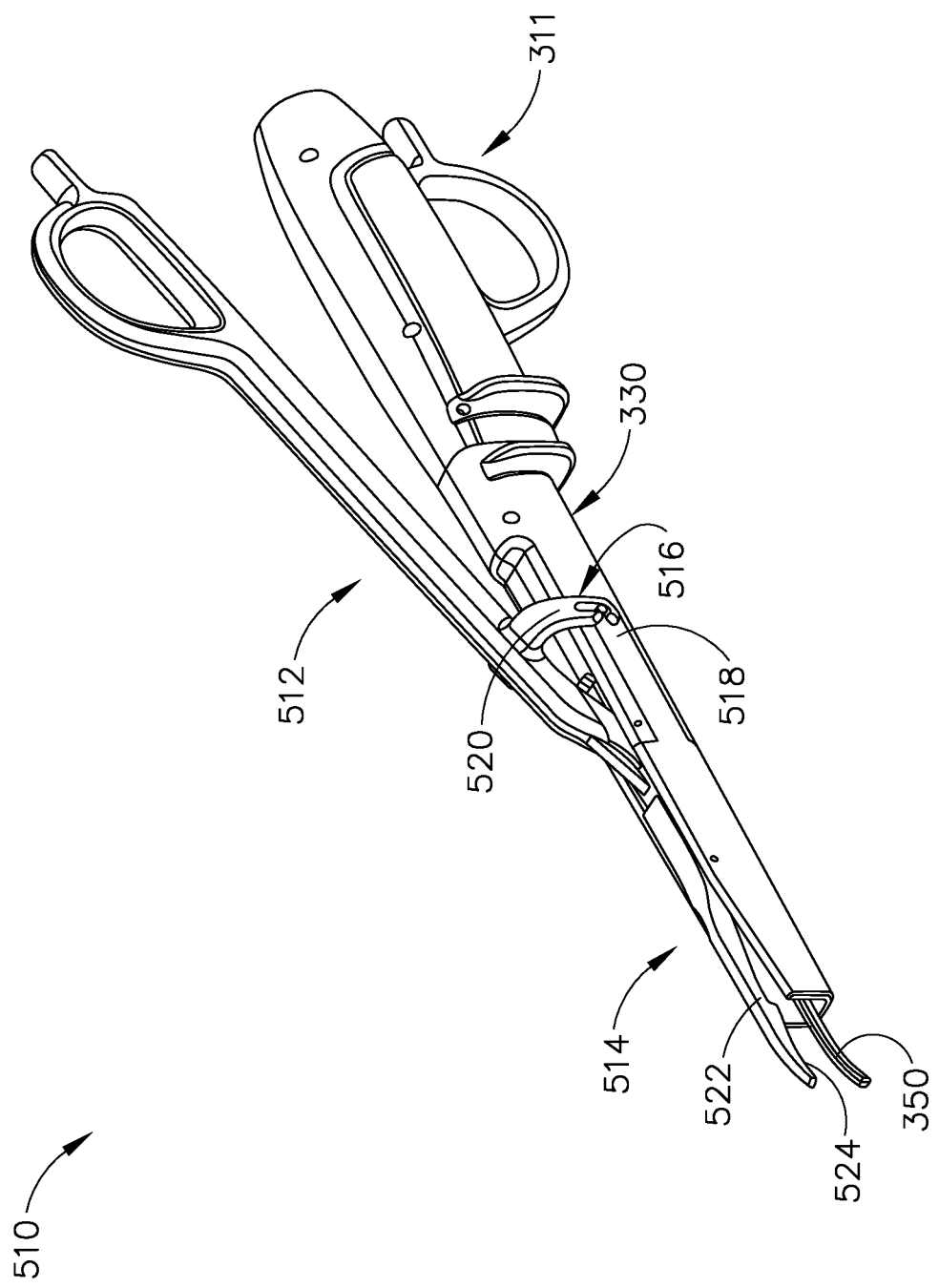
FIG. 24 depicts a perspective view of a third exemplary surgical instrument in an open configuration having a first modular alignment release coupling.
Figure 25:
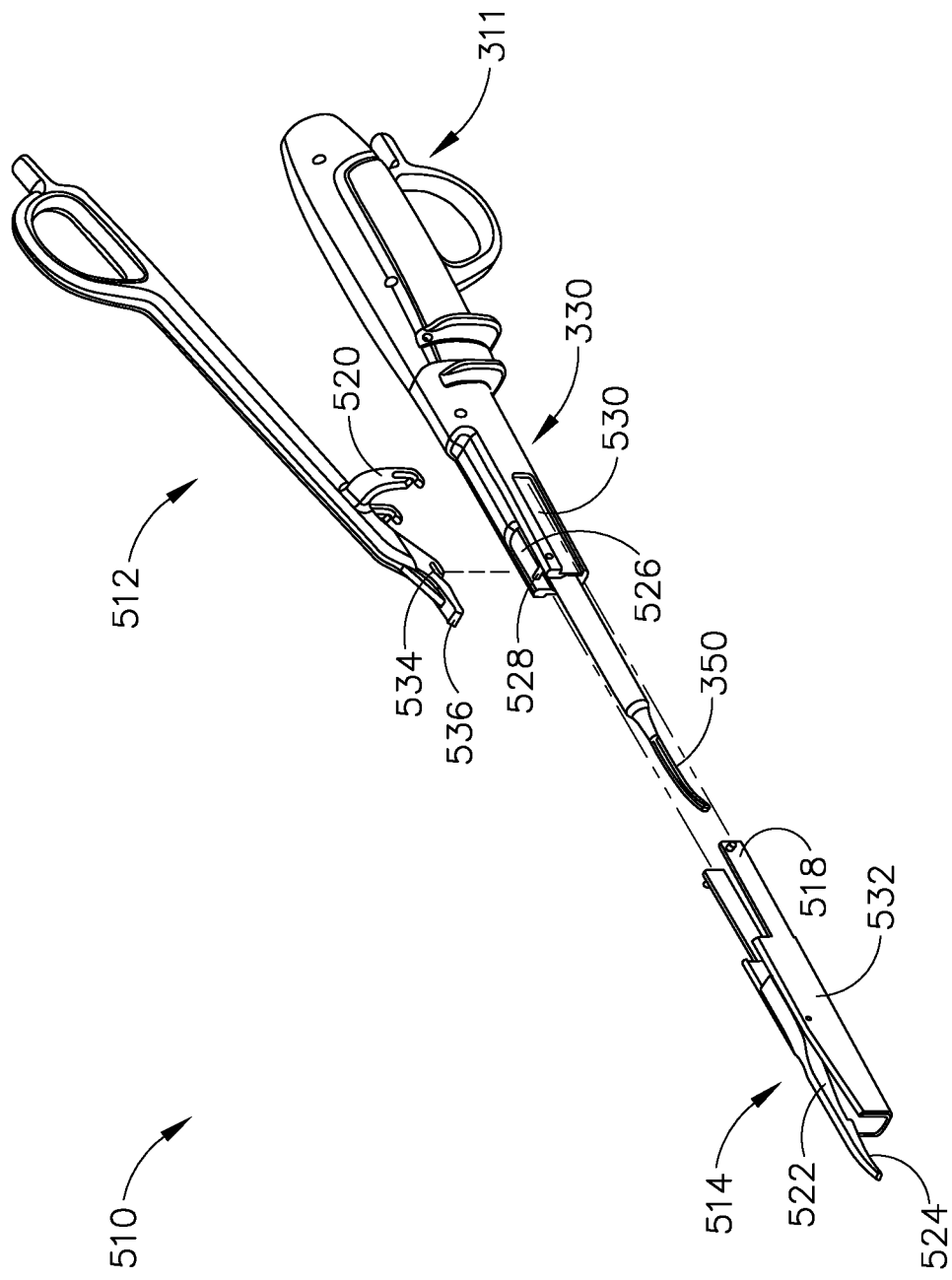
FIG. 25 depicts a partially exploded perspective view of the surgical instrument of FIG. 24.

As shown in FIG. 23, recesses (436) have a generally U-shaped configuration. Recesses (436) are configured to receive camming protrusions (328) of clamp arm actuator (320). In other words, when shaft assembly (330) is inserted into clamp arm assembly (400) as described above, camming protrusions (328) will enter recesses (436) when latch member (412) reaches the point at which latch member (412) secures clamp arm assembly (400) to shaft assembly (330). When the operator removes clamp arm assembly (400) from shaft assembly (330), camming protrusions (328) may freely exit recesses (436), as clamp arm actuator (320) remains secured to shaft assembly (330). As best seen in FIG. 17, shrouds (402, 404) are configured to cover the interfaces between recesses (436) and camming protrusions (328). It should be understood that the relationship between recesses (436) and camming protrusions (328) is substantially identical to the relationship between camming protrusion (216) and camming recess (226) described above. Thus, recesses (436) and camming protrusions (328) provide a pivoting coupling between clamp arm body (430) and clamp arm actuator (320).

As noted above, clamp arm actuator (320) is pivotally coupled with shaft assembly (330) via pin (338); and clamp arm body (430) is pivotally coupled with stationary body (410) via pin (440); while stationary body (410) is fixedly secured to shaft assembly (330). The pivoting interface between recesses (436) and camming protrusions (328) is longitudinally positioned between the longitudinal positions of pins (338, 440). It should therefore be understood that clamp arm actuator (320) and clamp arm body (430) cooperate to provide a compound lever assembly. When an operator pivots thumb ring (324) toward handle assembly (311), the compound lever action provides corresponding pivotal movement of clamp pad (432) toward ultrasonic blade (350).

In the present example, a resilient beam (313) is secured to clamp arm actuator (320) and slidably bears against shaft assembly (330), such that resilient beam (313) resiliently urges clamp arm actuator (320) away from handle assembly (311). Thus, when an operator relaxes their grip on thumb ring (324), resilient beam (313) will urge thumb ring (324) away from handle assembly (311), thereby urging clamp pad (432) away from ultrasonic blade (350). Of course, any other suitable components and arrangements may be used to provide a resilient bias to clamp arm actuator (320). Alternatively, such resilient bias may simply be omitted.

III. Alternative Exemplary Ultrasonic Surgical Instruments and Various Replaceable End Effector Features Surgical instruments (10, 301) described above have a variety of coupling mechanisms including associated connections for respective modular assemblies and other removably connected features. While such coupling mechanisms may be useful in many circumstances before, during, or after a surgical procedure, in one example, removing a replaceable portion of surgical instrument from a remainder of surgical instrument (10, 301) allows for replacement of the replaceable portion and reuse of the remainder of surgical instrument (10, 301). One such replaceable portion is clamp pad (222, 432), which tends to wear with use, and may be replaced by the operator as desired. However, additional replacement portions for end effector (12) include, but are not limited to, clamp arm assemblies (210, 400), and electrode assemblies, such as electrodes (not shown) discussed briefly above.

The operator disconnects removable portions of end effector (12) for replacement by manipulating modular couplings (516, 556, 566), directly or indirectly, as described below in greater detail. While the following modular couplings (516, 556, 566) are shown in distinct positions between reusable and replaceable features for removable connection, any of the following modular couplings (516, 556, 566), it will be appreciated that modular couplings (516, 556, 566) may be incorporated into any surgical instrument described herein, exchanged, or moved so as to make one or more portions of a surgical instrument removable from a remainder of the surgical instrument. To this end, other suitable kinds of clamp arm assemblies that may be used to provide different kinds of modular assemblies will be apparent to those of ordinary skill in the art in view of the teachings herein.

Like reference numerals described above indicate like features below. In addition, the following will provide descriptions of removal for modular couplings (516, 556, 566), but, unless otherwise noted, replacement of a replaceable portion, such as a replacement clamp arm assembly, is performed in reverse movement and steps for reassembly thereof. The following thus applied to both removal and replacement of various replaceable end effector features and is not intended to be limited to only removal thereof.

A. Third Exemplary Ultrasonic Surgical Instrument with a Variety of Modular Alignment Release Couplings FIGS. 24-30F illustrate a third exemplary surgical instrument (510) having handle assembly (311), shaft assembly (330), a clamp arm actuator (512), a clamp arm assembly (514), and a first modular alignment release coupling (516). With respect to FIGS. 24-25, clamp arm assembly (514) is removably connected to clamp arm actuator (512) with modular alignment release coupling (516), which includes a clamp body connection (518) extending from clamp arm assembly (514) and a clamp actuator connection (520) extending from clamp arm actuator (512). Clamp arm assembly (514) includes a clamp body (522) and a clamp pad (524). Clamp pad (524) is connected to clamp body (522) such that clamp pad (524) faces ultrasonic blade (350) for receiving and clamping tissue therebetween. Selective movement of clamp arm actuator (512) relative to handle assembly (311) from an opened configuration to a closed configuration respectively moves clamp arm assembly (514) from an opened position configured to receive tissue to a closed position configured to clamp the tissue. In the present example, selective movement of clamp arm actuator (512) to a release configuration aligns clamp actuator connection (520) relative to the clamp body connection (518) to disconnect clamp arm assembly (514) from clamp arm actuator (512) for removal and replacement of clamp arm assembly (514). While not shown with respect to surgical instrument (510), clamp arm assembly (514) may further include one or more electrodes configured to deliver RF energy to tissue for affecting the tissue, such as coagulating vessels in use.

Figure 26:
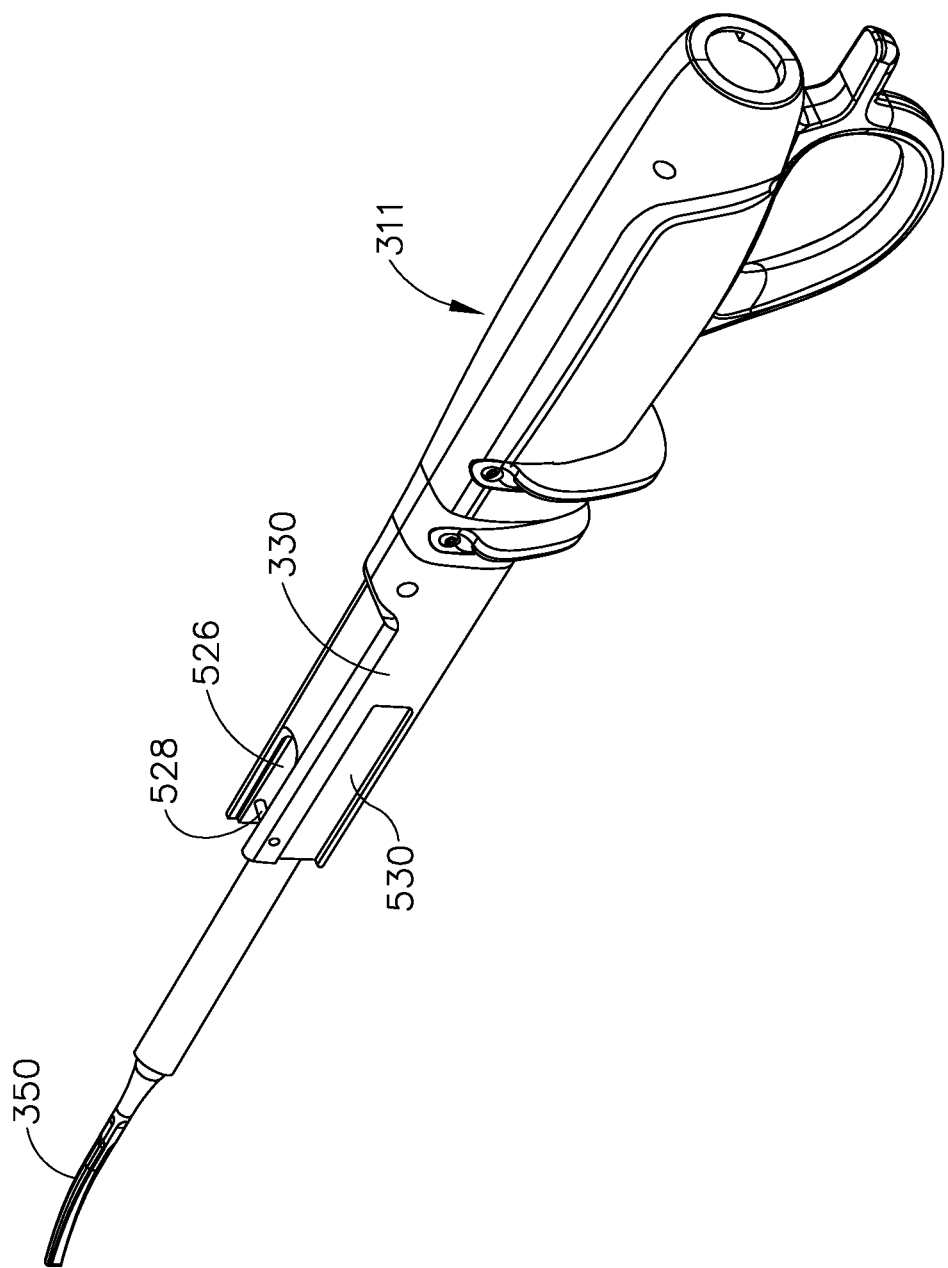
FIG. 26 depicts a perspective view of a handle assembly of the surgical instrument of FIG. 24.
Figure 27:
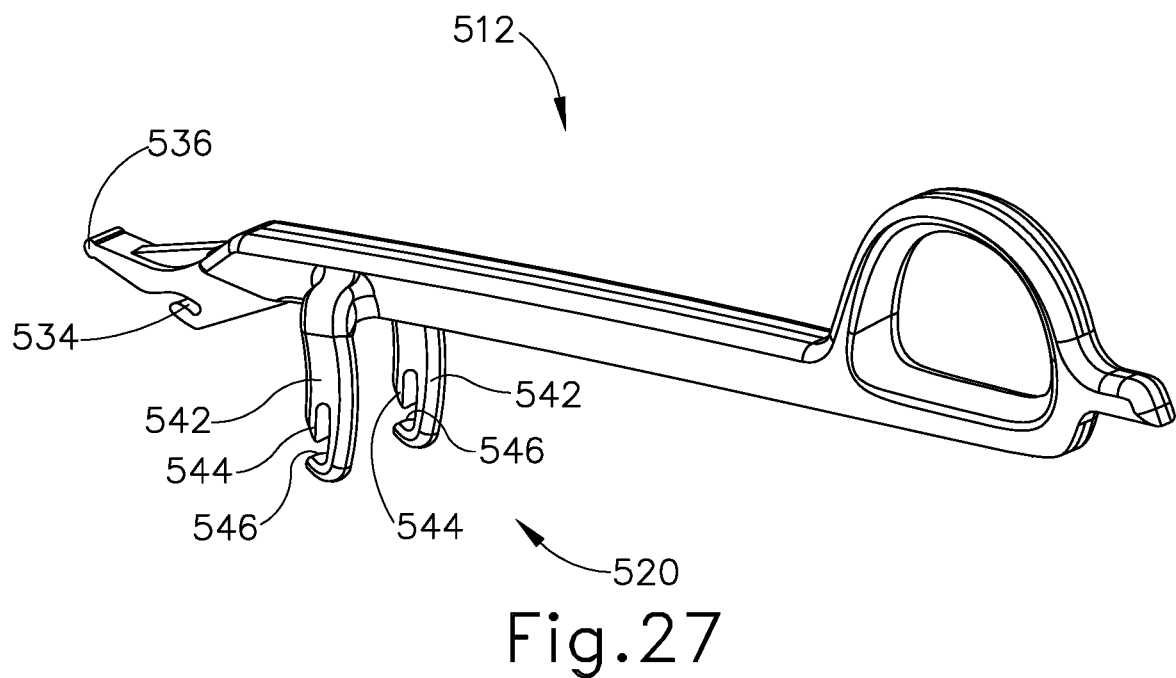
FIG. 27 depicts a perspective view of a clamp arm actuator of the surgical instrument of FIG. 24.
Figure 28:
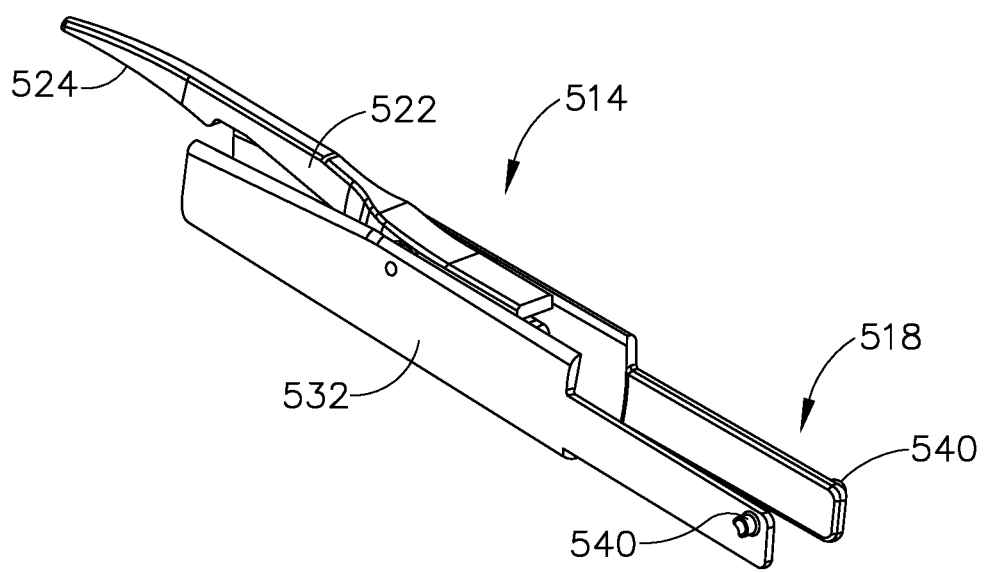
FIG. 28 depicts a perspective view of a clamp arm assembly of the surgical instrument of FIG. 24.
Figure 29A:
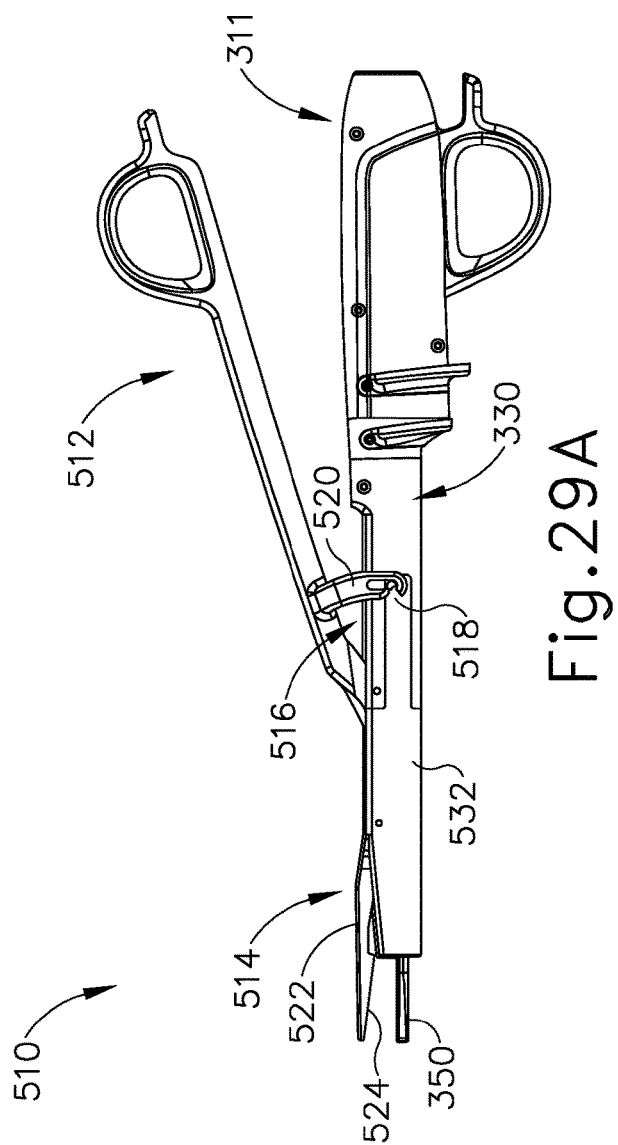
FIG. 29A depicts a side view of the surgical instrument of FIG. 24 in the open configuration.
Figure 29B:
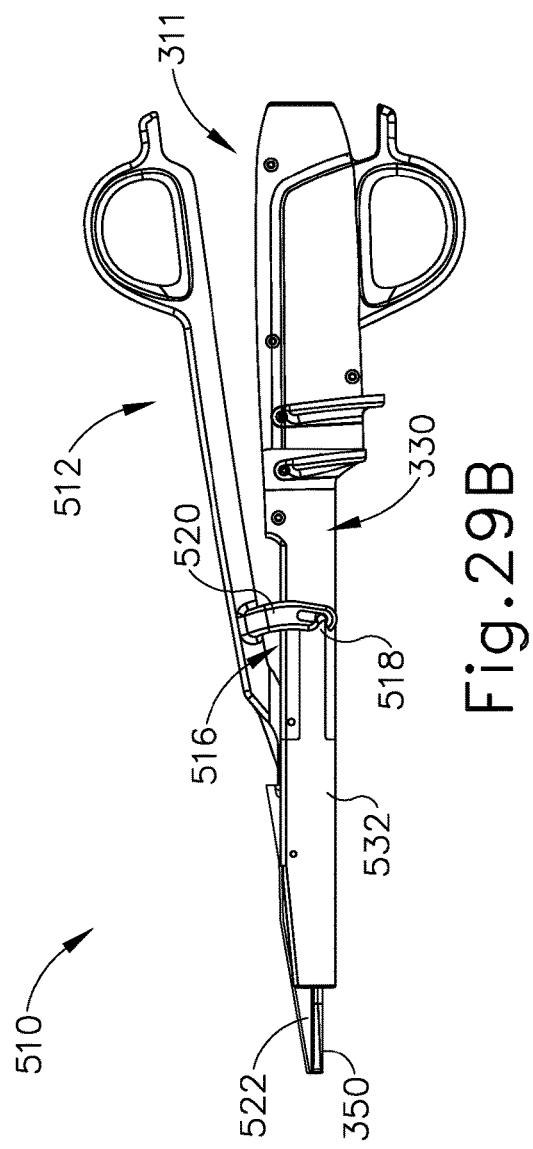
FIG. 29B depicts the side view of the surgical instrument similar to FIG. 29A, but showing the surgical instrument in a closed configuration.

FIG. 26 illustrates handle assembly (311) and shaft assembly (330) configured to receive each of clamp arm actuator (512) and clamp arm assembly (514) for use. Shaft assembly (330) has an upper elongate body groove (526) with a pin (528) extending laterally therethrough as well as a pair of side elongate body grooves (530). Upper elongate body groove (526) and side elongate body grooves (530) are configured to respectively receive a distal portion of clamp arm actuator (512) and a proximal portion of a distal outer sheath (532) shown in FIG. 27 and FIG. 28. More particularly, clamp arm actuator (512) has a distal pin slot (534) that removably receive pin (528) for pivotal movement thereabout and a distal nose (536) configured to movably engage a U-shaped channel (538) (see FIG. 30A) of clamp arm assembly (514) for directing movement therealong from the opened to the closed configurations. In the present example, movement of clamp arm actuator (512) about pin (528) and engagement with clamp arm assembly (514) is positioned above the longitudinal axis through shaft assembly (330).

With respect to FIGS. 27-29B, clamp body connection (518) includes a pair of opposing lateral tabs (540) extending laterally from the proximal portion of distal outer sheath (532), whereas clamp actuator connection (520) includes a pair of elongate hooks (542) extending downward toward lateral tabs (540). Elongate hooks (542) respectively receive lateral tabs (540) and capture lateral tabs (540) for movement from the opened to the closed configurations to thereby removably connect clamp arm assembly (514) to clamp arm actuator (512). More particularly, each elongate hook (542) has an inner abutment (544) configured to inhibit movement of lateral tab (540) to releasably capture lateral tab (540) respectively in elongate hook (542). However, at least one of elongate hook (542), inner abutment (544), or lateral tab (540) is configured to deflect under a release force to direct clamp arm actuator (512) and clamp arm assembly (514) collectively beyond the opened configuration to the release configuration such that lateral tabs (540) align with an opening (546) in each elongate hook (542) for removal.

In use, FIGS. 30A-30B illustrate clamp arm actuator (512) and clamp arm assembly (514) collectively in opened and closed configurations. With respect to FIG. 30C, the operator applies the release force for deflection to urge lateral tab (540) to a bottom of elongate hook (542) to the release configuration such that openings (546) longitudinally align with lateral tabs (540). The operator then distally translates clamp arm assembly (514) relative to shaft assembly (330) to disengage u-shaped channel (538) from distal nose (536) in FIG. 30D. Furthermore, clamp arm actuator (512) is removable from upper elongate body groove (526) with upward and proximal movement relative to shaft assembly (330) as shown in FIGS. 30E-30F.

FIGS. 31-32B illustrate a second modular alignment release coupling (556) similar to first modular alignment release coupling (516), but having a clamp arm actuator (558) without elongate hooks (542) (see FIG. 30A) for installation with less manipulation by the operator. In other respects, clamp arm actuator (558) and clamp arm assembly (514) are configured for manipulation from the closed configuration to the release configuration for removal of clamp arm assembly (514).

Figure 33:
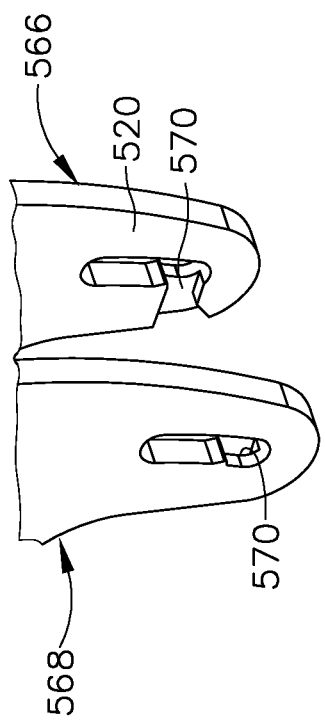
FIG. 33 depicts an enlarged side view of a third modular alignment release coupling with the clamp arm actuator for the surgical instrument of FIG. 24.
Figure 35:
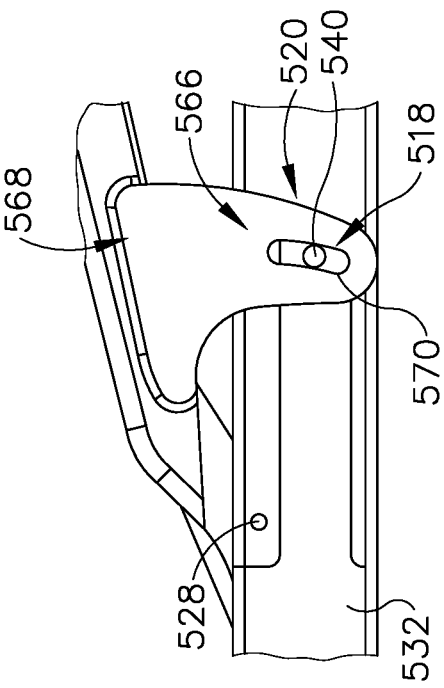
FIG. 35 depicts an enlarged side view of the modular alignment release coupling of FIG. 33 with the clamp arm actuator and the end effector for the surgical instrument of FIG. 24 in an open configuration.
Figure 34:
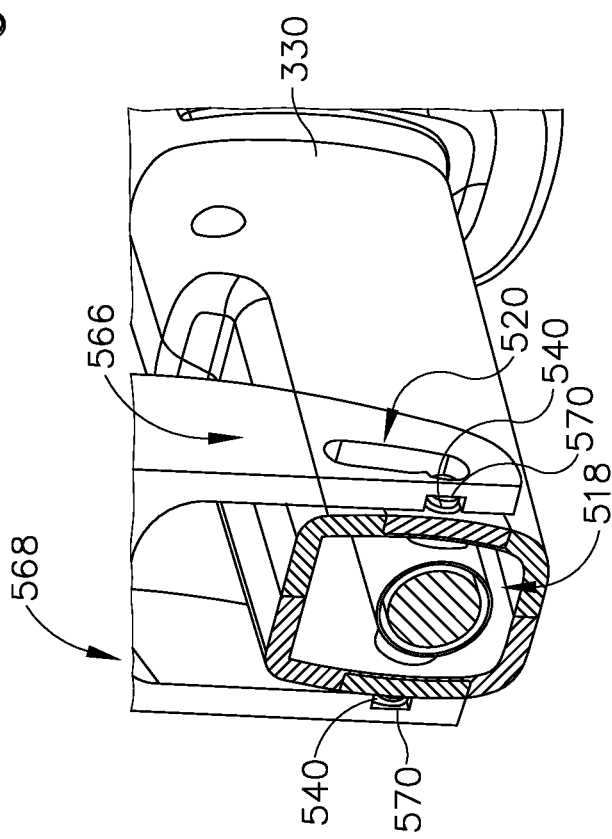
FIG. 34 depicts a sectional perspective view of the surgical instrument of FIG. 33 in a release configuration.

FIGS. 33-35 illustrate a third modular alignment release coupling (566) similar to first modular alignment release coupling (516), but having a clamp arm actuator (568) with slots (570) rather than elongate hooks (542) (see FIG. 30A) to further inhibit inadvertent removal of clamp arm assembly (514). To this end, the operator applies a force to bypass inner abutments (544) and align tabs (540) with slots (570) for removal as discussed above.

B. Fourth Exemplary Ultrasonic Surgical Instrument with Pivot Pin Linkage with Link FIGS. 36-38 illustrate a fourth exemplary surgical instrument (9100), similar to instrument (10), with like elements having like numbering. As shown in FIG. 16B, in some versions of end effector (12), camming protrusion (216) extends distally from elongated arm (212) to directly connect to arm (224). As shown in FIGS. 36-38, in some versions of instrument (9100), rather than protrusion (216), instrument (9100) may include an actuation arm (9102) connected to a clamp arm (9104) using a link (9106) disposed therebetween. Link (9106) extends from a first end (9108) to a second end (9110). First end (9108) is pinned or otherwise rotatably attached to actuation arm (9102), which is configured to pivot about pivot coupling (218). Second end (9110) of link (9106) is pinned or otherwise rotatably attached to clamp arm (9104), which pivots about pivot coupling (228).

Link (9106) is movable between a first position (FIG. 37) and a second position (FIG. 38). To move link (9106) from the first position to the second position, grip ring (214) is actuated in the direction of Arrow (9100A), actuation arm (9102) pivots about pivot coupling (218), lifting first end (9108) of link (9106). In response, the lifting of first end (9108) of link (9106) moves second end (9110) of link (9106). Inasmuch as second end (9110) of link (9106) is connected to clamp arm (9104), clamp arm (9104) is lifted and pivoted about pivot coupling (228). To move link (9106) from the second position to the first position, grip ring (214) is actuated in the direction of Arrow (9100B).

As depicted in FIG. 37, actuation arm (9102) and clamp arm (9104) are indirectly connected, rather than directly connected as shown in FIG. 16B. The indirection connection provides a positive, smooth connection between actuation arm (9102) and clamp arm (9104), which translates to a smooth transfer of power from grip ring (214) into the clamping of the tissue. The indirect connection between actuation arm (9102) and clamp arm (9104) also prevents the disengagement of the coupling, as link (9106) is secured to both actuation arm (9102) and clamp arm (9104). By indirectly connecting actuation arm (9102) and clamp arm (9104) backlash and slop within the clamping mechanism are minimized. Further, link (9106) provides for fine tuning the mechanical advantage by changing the overall length of link (9106).

C. Fifth Exemplary Ultrasonic Surgical Instrument with Pivot Pin Linkage with Slot As shown between FIGS. 1A-1B and 16A-16B, when an operator rotates elongated arm (212) about pivot coupling (218) toward distal outer sheath (230), camming protrusion (216) rotates away from distal outer sheath (230) about pivot coupling (218). The tight tolerance between elongated arm (212) and pivot coupling (218) restricts the movement of elongated arm (212) solely to rotation about the axis of pivot coupling (218).

Figure 39:
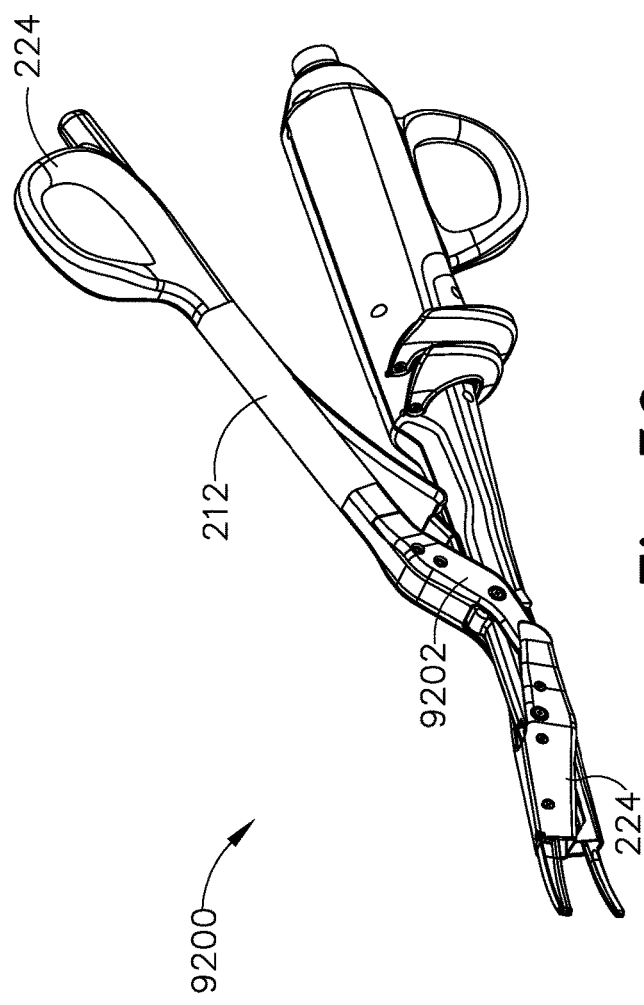
FIG. 39 depicts a perspective view of a fifth exemplary surgical instrument, similar to the surgical instrument of FIG. 1A.
Figure 41:
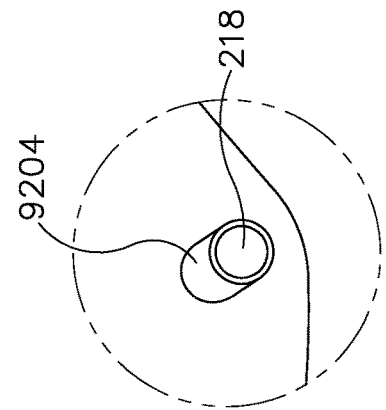
FIG. 41 depicts an enlarged view of the actuation arm and an exemplary pivot coupling of FIG. 40.
Figure 40:
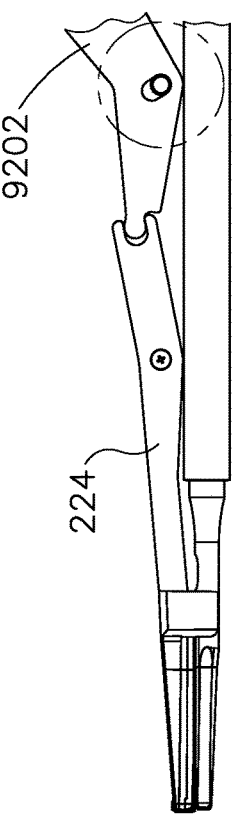
FIG. 40 depicts a side elevational view of an exemplary arm of the surgical instrument of FIG. 39 connected with an exemplary actuation arm of the surgical instrument of FIG. 39.

FIGS. 39-41 illustrate a fifth exemplary surgical instrument (9200), similar to instrument (10), with like elements having like numbering. In some versions of instrument (9200), instrument (9200) provides an actuation arm (9202), which defines a slot (9204) for receiving pivot coupling (218). Slot (9204) allows for translation of actuation arm (9202) in addition to rotation about the axis of pivot coupling (218). Thus, slot (9204) provides for a smooth mechanical linkage between actuation arm (9202) and arm (224).

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

A surgical instrument, comprising: (a) a first modular assembly comprising: (i) a body, (ii) an ultrasonic waveguide configured to couple with an ultrasonic transducer, (iii) an ultrasonic blade connected to a distal end of the ultrasonic waveguide, and (iv) a coupling member configured to movably couple with the body; and (b) a second modular assembly comprising: (i) a clamp arm assembly comprising a first pivot coupling, (ii) a clamp pad assembly comprising a second pivot coupling, and (iii) a distal outer sheath configured to selectively couple to the body of the first modular assembly via the coupling member, wherein the distal outer sheath comprises an interior surface configured to house a portion of the ultrasonic waveguide, wherein the interior surface of the distal outer sheath is configured to house the first pivot coupling and the second pivot coupling.

EXAMPLE 2

The surgical instrument of Example 1, wherein the distal outer sheath comprises a U-shaped body.

EXAMPLE 3

The surgical instrument of any one or more of Examples 1 through 2, wherein the body comprises a recess, wherein the distal outer sheath comprises a proximal protrusion configured to be inserted into the recess.

EXAMPLE 4

The surgical instrument of Example 3, wherein the proximal protrusion comprises a lateral protrusion, wherein the coupling member is configured to mate with the lateral protrusion to couple the distal outer sheath with the body of the first modular assembly.

EXAMPLE 5

The surgical instrument of Example 4, wherein the coupling member comprises a resilient arm defining a locking assembly, wherein the locking assembly is configured to couple with the lateral protrusion.

EXAMPLE 6

The surgical instrument of any one or more of Examples 1 through 5, wherein the coupling member is pivotally coupled with the body.

EXAMPLE 7

The surgical instrument of any one or more of Examples 1 through 6, wherein the clamp arm assembly comprises a camming protrusion.

EXAMPLE 8

The surgical instrument of Example 7, wherein the clamp pad assembly comprises a camming recess, wherein the camming protrusion and the camming recess are configured to mate with each other.

EXAMPLE 9

The surgical instrument of Example 8, wherein the camming recess and the camming protrusion are located between the first pivot coupling and the second pivot coupling.

EXAMPLE 10

The surgical instrument of any one or more of Examples 1 through 9, wherein the clamp pad assembly comprises a tissue stop.

EXAMPLE 11

The surgical instrument of any one or more of Examples 1 through 10, wherein the clamp pad assembly comprises a resilient member configured to bias the clamp pad in an open configuration.

EXAMPLE 12

The surgical instrument of any one or more of Examples 1 through 11, wherein the clamp arm assembly comprises a thumb ring grip.

EXAMPLE 13

The surgical instrument of any one or more of Examples 1 through 12, wherein the body comprises a finger ring grip.

EXAMPLE 14

The surgical instrument of any one or more of Examples 1 through 13, wherein the first modular assembly further comprises a tube extending from the body.

EXAMPLE 15

The surgical instrument of Example 14, wherein the waveguide is housed within the tube.

EXAMPLE 16

The surgical instrument of Example 15, further comprising a seal located between the waveguide and the tube.

EXAMPLE 17

The surgical instrument of any one or more of Examples 1 through 16, wherein the ultrasonic blade extends distally from the tube.

EXAMPLE 18

The surgical instrument of any one or more of Examples 1 through 17, further comprising an ultrasonic transducer at least partially housed within the body, wherein the ultrasonic waveguide is coupled with the ultrasonic transducer.

EXAMPLE 19

A surgical instrument, comprising: (a) a first modular assembly comprising: (i) a body, (ii) an ultrasonic waveguide, and (iii) an ultrasonic blade connected to a distal end of the ultrasonic waveguide; and (b) a second modular assembly comprising: (i) a clamp arm assembly comprising a first pivot coupling, (ii) a clamp pad assembly comprising a second pivot coupling, and (iii) a distal outer sheath configured to secure the second modular assembly to the body of the first modular assembly, wherein the distal outer sheath comprises an interior surface configured to house a portion of the ultrasonic waveguide, wherein the interior surface of the distal outer sheath is configured to house the first pivot coupling and the second pivot coupling.

EXAMPLE 20

A surgical instrument, comprising: (a) a first modular assembly comprising: (i) a body, (ii) an ultrasonic waveguide, and (iii) an ultrasonic blade connected to a distal end of the ultrasonic waveguide; and (b) a second modular assembly comprising: (i) a clamp arm assembly comprising a first pivot coupling, (ii) a clamp pad assembly comprising a second pivot coupling, wherein a proximal end of the clamp pad assembly is pivotably coupled with a distal end of the clamp arm assembly via a third pivot coupling, wherein the third pivot coupling is longitudinally positioned between the first pivot coupling and the second pivot coupling, and (iii) a distal outer sheath configured to secure the second modular assembly to the body of the first modular assembly, wherein the distal outer sheath comprises an interior surface configured to house a portion of the ultrasonic waveguide, wherein the interior surface of the distal outer sheath is configured to house the first pivot coupling and the second pivot coupling.

EXAMPLE 21

A surgical instrument, comprising: (a) an end effector, including: (i) an ultrasonic blade including a first electrode, and (ii) a clamp arm configured to move relative to the ultrasonic blade; and (b) an elongated arm for actuating the clamp arm, wherein the clamp arm and the elongated arm are indirectly connected.

EXAMPLE 22

The surgical instrument of Example 21, further comprising a link having a first end and a second end, wherein the first end of the link is coupled to the clamp arm, wherein the second end of the link is coupled to the elongated arm.

EXAMPLE 23

A surgical instrument, comprising: (a) an end effector, including: (i) an ultrasonic blade including a first electrode, and (ii) a clamp arm configured to move relative to the ultrasonic blade; and (b) an elongated arm for actuating the clamp arm, wherein the elongated arm is movable about a pivot coupling extending through a slot defined by the elongated arm.

V. Miscellaneous

While various examples herein describe two or more modular components being releasably coupled together, it should be understood that some variations may eliminate such modularity and releasable couplings. For instance, some versions of instrument (10) may provide first modular assembly (100) and second modular assembly (200) as a single combined unit that does not permit second modular assembly (200) to be removed form first modular assembly (100). In some such versions, coupling member (300) would either me omitted (with some other feature being used to provide permanent coupling between first modular assembly (100) and second modular assembly (200)); or coupling member (300) may be modified such that coupling member (300) may not be manipulated to decouple second modular assembly (200) from first modular assembly (100). Similarly, some versions of instrument (301) may prevent clamp arm assembly (400) from being removed from shaft assembly (330). For instance, latch member (412) may be omitted and clamp arm assembly (400) may be permanently coupled with shaft assembly (330).

It should be understood that the various teachings herein may be readily combined with the various teachings of U.S. Pub. No. 2017/0105754, entitled "Surgical Instrument with Dual Mode End Effector and Side-Loaded Clamp Arm Assembly," published on Apr. 20, 2017, the disclosure of which is incorporated by reference herein. Various suitable ways in which the teachings herein may be combined with the teachings of U.S. Pub. No. 2017/0105754 will be apparent to those of ordinary skill in the art.

It should be understood that the various teachings herein may be readily combined with the various teachings of U.S.

Pub. No. 2017/0105755, entitled "Surgical Instrument with Dual Mode End Effector and Compound Lever with Detents," published on Apr. 20, 2017, issued as U.S. Pat. No. 11,020,200 on Jun. 1, 2021, the disclosure of which is incorporated by reference herein. Various suitable ways in which the teachings herein may be combined with the teachings of U.S. Pub. No. 2017/0105755, issued as U.S. Pat. No. 11,020,200 on Jun. 1, 2021, will be apparent to those of ordinary skill in the art.

It should be understood that the various teachings herein may be readily combined with the various teachings of U.S. Pub. No. 2017/0105788, entitled "Surgical Instrument with Dual Mode End Effector and Modular Clamp Arm Assembly," published on Apr. 20, 2017, issued as U.S. Pat. No. 10,893,914 on Jan. 19, 2021, the disclosure of which is incorporated by reference herein. Various suitable ways in which the teachings herein may be combined with the teachings of U.S. Pub. No. 2017/0105788, issued as U.S. Pat. No. 10,893,914 on Jan. 19, 2021, will be apparent to those of ordinary skill in the art.

The various instruments described above may be used in a variety of kinds of surgical procedures. By way of example only, the instruments described above may be used to perform liver resection, colorectal surgical procedures, gynecological surgical procedures, and/or various other kinds of surgical procedures. Various other kinds of procedures and ways in which the instruments described above may be used will be apparent to those of ordinary skill in the art in view of the teachings herein.

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

In addition to the foregoing, the teachings herein may be readily combined with the teachings of U.S. patent application Ser. No. 15/798,703, entitled "Surgical Instruments with Removable End Effector Components," filed on Oct. 31, 2017, published as U.S. Pub. No. 2018/132887 on May 17, 2018, the disclosure of which is incorporated by reference herein. Various suitable ways in which the teachings herein may be combined with the teachings of U.S. patent application Ser. No. 15/798,703, filed on Oct. 31, 2017, published U.S. Pub. No. 2018/0132887 on May 17, 2018, will be apparent to those of ordinary skill in the art in view of the teachings herein.

In addition to the foregoing, the teachings herein may be readily combined with the teachings of U.S. patent application Ser. No. 15/798,720, entitled "Surgical Instrument with Selectively Actuated Gap-Setting Features for End Effector," filed on Oct. 31, 2017, published as U.S. Pub. No. 2018/0132888 on May 17, 2018, the disclosure of which is incorporated by reference herein. Various suitable ways in which the teachings herein may be combined with the teachings of U.S. patent application Ser. No. 15/798,720 filed on Oct. 31, 2017, published as U.S. Pub. No. 2018/0132888 on May 17, 2018, will be apparent to those of ordinary skill in the art in view of the teachings herein.

In addition to the foregoing, the teachings herein may be readily combined with the teachings of U.S. patent application Ser. No. 15/798,835, entitled "Surgical Instrument with Spot Coagulation Control Algorithm," filed on Oct. 31, 2017, published as U.S. Pub. No. 2018/0132926 on May 17, 2018, the disclosure of which is incorporated by reference herein. Various suitable ways in which the teachings herein may be combined with the teachings of U.S. patent application Ser. No. 15/798,835 filed on Oct. 31, 2017, published as U.S. Pub. No. 2018/0132926 on May 17, 2018, will be apparent to those of ordinary skill in the art in view of the teachings herein.

In addition to the foregoing, the teachings herein may be readily combined with the teachings of U.S. patent application Ser. No. 15/798,902, entitled "Surgical Instrument with Removable Portion to Facilitate Cleaning," filed on Oct. 31, 2017, issued as U.S. Pat. No. 10,736,648 on Aug. 11, 2020, the disclosure of which is incorporated by reference herein. Various suitable ways in which the teachings herein may be combined with the teachings of U.S. patent application Ser. No. 15/798,902 filed on Oct. 31, 2017, issued as U.S. Pat. No. 10,736,648 on Aug. 11, 2020, will be apparent to those of ordinary skill in the art in view of the teachings herein.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument, comprising:
   (a) a first modular assembly comprising:
      (i) a body,
      (ii) an ultrasonic waveguide configured to couple with an ultrasonic transducer,
      (iii) an ultrasonic blade connected to a distal end of the ultrasonic waveguide, and
      (iv) a coupling member configured to movably couple with the body; and
   (b) a second modular assembly comprising:
      (i) a clamp arm assembly comprising a first pivot coupling,
      (ii) a clamp pad assembly comprising an arm having a second pivot coupling positioned thereon, and
      (iii) a distal outer sheath extending in a longitudinal direction and configured to selectively couple to the body of the first modular assembly via the coupling member, wherein the distal outer sheath comprises an interior surface defining a pathway configured to house a portion of the ultrasonic waveguide, wherein the pathway of the distal outer sheath is configured to at least partially receive the arm of the clamp pad assembly and house the first pivot coupling and the second pivot coupling inward of the interior surface, wherein each of the first and second pivot couplings are positioned transversely above the ultrasonic waveguide with the distal outer sheath housing the portion of the ultrasonic waveguide therein.

2. The surgical instrument of claim 1, wherein the distal outer sheath comprises a U-shaped body.

3. The surgical instrument of claim 1, wherein the body comprises a recess, wherein the distal outer sheath comprises a proximal protrusion configured to be inserted into the recess.

4. The surgical instrument of claim 3, wherein the proximal protrusion comprises a lateral protrusion, wherein the coupling member is configured to mate with the lateral protrusion to couple the distal outer sheath with the body of the first modular assembly.

5. The surgical instrument of claim 4, wherein the coupling member comprises a resilient arm defining a locking assembly, wherein the locking assembly is configured to couple with the lateral protrusion.

6. The surgical instrument of claim 1, wherein the coupling member is pivotally coupled with the body.

7. The surgical instrument of claim 1, wherein the clamp arm assembly comprises a camming protrusion.

8. The surgical instrument of claim 7, wherein the clamp pad assembly comprises a camming recess, wherein the camming protrusion and the camming recess are configured to mate with each other.

9. The surgical instrument of claim 8, wherein the camming recess and the camming protrusion are located between the first pivot coupling and the second pivot coupling.

10. The surgical instrument of claim 1, wherein the clamp pad assembly comprises a tissue stop.

11. The surgical instrument of claim 1, wherein the clamp pad assembly comprises a resilient member configured to bias the clamp pad assembly in an open configuration.

12. The surgical instrument of claim 1, wherein the clamp arm assembly comprises a thumb ring grip.

13. The surgical instrument of claim 1, wherein the body comprises a finger ring grip.

14. The surgical instrument of claim 1, wherein the first modular assembly further comprises a tube extending from the body.

15. The surgical instrument of claim 14, wherein the waveguide is housed within the tube.

16. The surgical instrument of claim 15, further comprising a seal located between the waveguide and the tube.

17. The surgical instrument of claim 14, wherein the ultrasonic blade extends distally from the tube.

18. The surgical instrument of claim 1, further comprising an ultrasonic transducer at least partially housed within the body, wherein the ultrasonic waveguide is coupled with the ultrasonic transducer.

19. A surgical instrument, comprising:
   (a) a first modular assembly comprising:
      (i) a body,
      (ii) an ultrasonic waveguide, and
      (iii) an ultrasonic blade connected to a distal end of the ultrasonic waveguide; and
   (b) a second modular assembly comprising:
      (i) a clamp arm assembly comprising an arm having a first pivot coupling positioned thereon,
      (ii) a clamp pad assembly comprising a second pivot coupling, and
      (iii) a distal outer sheath extending in a longitudinal direction and configured to secure the second modular assembly to the body of the first modular assembly, wherein the distal outer sheath comprises an interior surface defining a pathway configured to house a portion of the ultrasonic waveguide, wherein the pathway of the distal outer sheath is configured to at least partially receive the arm of the clamp arm assembly and house the first pivot coupling and the second pivot coupling inward of the interior surface, wherein each of the first and second pivot couplings are positioned transversely above the ultrasonic waveguide with the distal outer sheath housing the portion of the ultrasonic waveguide therein.

20. A surgical instrument, comprising:
(a) a first modular assembly comprising:
   (i) a body,
   (ii) an ultrasonic waveguide, and
   (iii) an ultrasonic blade connected to a distal end of the ultrasonic waveguide; and
(b) a second modular assembly comprising:
   (i) a clamp arm assembly comprising a first arm having a first pivot coupling positioned thereon,
   (ii) a clamp pad assembly comprising a second arm having a second pivot coupling positioned thereon, wherein a proximal end of the second arm is pivotably coupled with a distal end of the first arm via a third pivot coupling, wherein the third pivot coupling is longitudinally positioned between the first pivot coupling and the second pivot coupling, and
   (iii) a distal outer sheath extending in a longitudinal direction and configured to secure the second modular assembly to the body of the first modular assembly, wherein the distal outer sheath comprises an opening and an interior surface defining a pathway configured to house a portion of the ultrasonic waveguide, wherein the opening transversely extends into the pathway such that the pathway of the distal outer sheath is configured to at least partially receive each of the first and second arms through the opening and house the first pivot coupling and the second pivot coupling inward of the interior surface.

* * * * *